US009150827B2

(12) United States Patent
Wendisch et al.

(10) Patent No.: US 9,150,827 B2
(45) Date of Patent: Oct. 6, 2015

(54) METHOD FOR THE FERMENTATIVE PRODUCTION OF L-AMINO ACIDS WITH THE AID OF CORYNEFORM BACTERIA CAPABLE OF USING GLYCERIN AS THE ONLY CARBON SOURCE

(75) Inventors: Volker F. Wendisch, Juelich (DE); Doris Rittmann, Juelich (DE); Hermann Sahm, Juelich (DE); Caroline Kreutzer, Oerlinghausen (DE)

(73) Assignee: EVONIK DEGUSSA GmbH, Essen (DE)

( * ) Notice: Subject to any disclaimer, the term of this patent is extended or adjusted under 35 U.S.C. 154(b) by 898 days.

(21) Appl. No.: 11/816,539

(22) PCT Filed: Sep. 27, 2006

(86) PCT No.: PCT/EP2006/066813
§ 371 (c)(1),
(2), (4) Date: Feb. 1, 2008

(87) PCT Pub. No.: WO2007/039532
PCT Pub. Date: Apr. 12, 2007

(65) Prior Publication Data
US 2008/0293100 A1    Nov. 27, 2008

(30) Foreign Application Priority Data
Oct. 5, 2005  (DE) .................. 10 2005 047 596

(51) Int. Cl.
*C12P 13/04* (2006.01)
*C12P 13/22* (2006.01)
*C12P 13/08* (2006.01)
*C12N 1/20* (2006.01)
*C12N 9/04* (2006.01)
*C12N 9/12* (2006.01)

(52) U.S. Cl.
CPC . *C12N 1/20* (2013.01); *C12P 13/04* (2013.01); *C12P 13/08* (2013.01); *C12P 13/227* (2013.01)

(58) Field of Classification Search
None
See application file for complete search history.

(56) References Cited

U.S. PATENT DOCUMENTS

| 6,200,785 | B1 | 3/2001 | Kreutzer et al. |
| 6,355,454 | B1 | 3/2002 | Marx et al. |
| 6,596,516 | B2 | 7/2003 | Ziegler et al. |
| 6,746,855 | B2 | 6/2004 | Kreutzer et al. |
| 6,861,246 | B2 | 3/2005 | Kreutzer et al. |
| 6,884,614 | B1 * | 4/2005 | Pompejus et al. ......... 435/252.3 |
| 7,094,584 | B2 | 8/2006 | Kreutzer et al. |
| 7,307,160 | B1 | 12/2007 | Ohtaki et al. |
| 7,435,584 | B2 | 10/2008 | Kruetzer et al. |
| 2002/0086371 | A1 | 7/2002 | Kreutzer et al. |
| 2002/0137150 | A1 | 9/2002 | Ohtaki et al. |
| 2002/0192674 | A1 | 12/2002 | Hermann et al. |
| 2003/0199045 | A1 | 10/2003 | Burke et al. |
| 2005/0079588 | A1 | 4/2005 | Sindelar et al. |
| 2005/0112733 | A1 | 5/2005 | Burke et al. |
| 2007/0134760 | A1 | 6/2007 | Olsen et al. |
| 2010/0124777 | A1 | 5/2010 | Ohtaki et al. |
| 2010/0151521 | A1 | 6/2010 | Olsen et al. |

FOREIGN PATENT DOCUMENTS

| DE | 103 44 739 | | 4/2005 |
| EP | 1 174 508 | A2 | 1/2002 |
| WO | 02 02777 | | 1/2002 |
| WO | WO 02/061093 | A1 | 8/2002 |
| WO | 2005 042750 | | 5/2005 |
| WO | 2005 121349 | | 12/2005 |
| WO | 2007/013695 | A1 * | 2/2007 |

OTHER PUBLICATIONS

Sweet et al. "Glycerol Facilitator of *Escherichia coli*: Cloning of glpF and Identification of the glpF Product", J. Bacteriol. 172:424-430, 1990.*
Maurel et al. "Functional Characterization of the *Escherichia coli* Glycerol Facilitator, GlpF, in Xenopus Oocytes", J. Biol. Chem. 269:11869-11872, 1994.*
Pettigrew et al., J. Biol. Chem. 263:135-139, 1988.*
Schweizer et al., Microbiol. 143:1287-1297, 1997.*
Lin, E., Ann. Rev. Microbiol. 30:535-578, 1976.*
Austin et al., J. Bacteriol. 173:101-107, 1991.*
Ohnishi et al., FEMS Microbiol. Lett. 242:265-274, 2005.*
Becker et al., Appl. Environ. Microbiol. 71:8587-8596, 2005.*
Rittman et al., Arch. Microbiol. 180:285-292, 2003.*
GenPept Accession No. P08859, May 2005, 12 pages.*
GenPept Accession No. AAA23886, Apr. 1993, 1 page.*
GenPept Accession No. P13035, Sep. 2005, 2 pages.*
Nakayama et al., M. Friedman (ed.), "Nutritional Improvement of Food and Feed Proteins", Plenum Press, New York 1978, pp. 649-661.*
Deanda et al., Appl. Environ. Microbiol. 62:4465-4470, 1996.*
U.S. Appl. No. 09/353,608, filed Jul. 14, 1999, Kreutzer, et al.
U.S. Appl. No. 12/249,092, filed Jun. 19, 2006, Kreutzer, et al.
U.S. Appl. No. 09/531,269, filed Mar. 20, 2000, Burke, et al.
U.S. Appl. No. 12/517,923, filed Jun. 5, 2009, Verseck, et al.
Yamada, et al., "Mechanism of D-Alanine Production by *Corynebacterium fascians*", Applied and Environmental Microbiology, vol. 32, No. 1, pp. 1-6, XP001053451, 1976.

(Continued)

*Primary Examiner* — David J Steadman
(74) *Attorney, Agent, or Firm* — Oblon, McClelland, Maier & Neustadt, L.L.P.

(57) ABSTRACT

A method for producing an L-amino acid comprising: a) cultivating in a medium containing glycerol a recombinant coryneform bacteria which produces the desired L-amino acid and which expresses at least one heterologous polynucleotide of glycerol metabolism, such as glpA, glpB, glpC, glpD, glpE, glpF, glpG, glpK, glpQ, gipT, glpX, gldA, dhaK, dhaL, dhaM, dhaR, fsa, and/or talC, and b) isolating the desired L-amino acid. Preferably, the pathways producing the desired L-amino acid in the coryneform bacteria are amplified.

19 Claims, No Drawings

(56) References Cited

OTHER PUBLICATIONS

Blattner, et al., "The Complete Genome Sequence of *Escherichia coli* K-12", Science, vol. 277, pp. 1453-1462, XP002069950, 1997.

Search Report issued Jun. 15, 2011 in Europe Application No. 11152912.9 (With English Translation of Category of Cited Documents).

Jörn Kalinowski, et al., "The complete *Corynebacterium glutamicum* ATCC 13032 genome sequence and its impact on the production of L-aspartate-derived amino acids and vitamins", Journal of Biotechnology, vol. 104, 2003, pp. 5-25.

Bernhard J. Eikmanns, "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase", Journal of Bacteriology, vol. 174, No. 19, Oct. 1992, pp. 6076-6086.

\* cited by examiner

SEQUENCE LISTING

```
<160> NUMBER OF SEQ ID NOS: 40

<210> SEQ ID NO 1
<211> LENGTH: 1629
<212> TYPE: DNA
<213> ORGANISM: Escherichia coli
<220> FEATURE:
<221> NAME/KEY: CDS
<222> LOCATION: (1)..(1629)
<223> OTHER INFORMATION: glpA coding region

<400> SEQUENCE: 1 atg aaa act cgc gac tcg caa tca agt gac gtg att atc att ggc ggc        48
Met Lys Thr Arg Asp Ser Gln Ser Ser Asp Val Ile Ile Ile Gly Gly
1               5                   10                  15 ggc gca acg gga gcc ggg att gcc cgc gac tgt gcc ctg cgc ggg ctg        96
Gly Ala Thr Gly Ala Gly Ile Ala Arg Asp Cys Ala Leu Arg Gly Leu
                20                  25                  30 cgc gtg att ttg gtt gag cgc cac gac atc gca acc ggt gcc acc ggg       144
Arg Val Ile Leu Val Glu Arg His Asp Ile Ala Thr Gly Ala Thr Gly
            35                  40                  45 cgt aac cac ggc ctg ctg cac agc ggt gcg cgc tat gcg gta acc gat       192
Arg Asn His Gly Leu Leu His Ser Gly Ala Arg Tyr Ala Val Thr Asp
        50                  55                  60 gcg gaa tcg gcc cgc gaa tgc att agt gaa aac cag atc ctg aaa cgc       240
Ala Glu Ser Ala Arg Glu Cys Ile Ser Glu Asn Gln Ile Leu Lys Arg
65                  70                  75                  80 att gca cgt cac tgc gtt gaa cca acc aac ggc ctg ttt atc acc ctg       288
Ile Ala Arg His Cys Val Glu Pro Thr Asn Gly Leu Phe Ile Thr Leu
                85                  90                  95 ccg gaa gat gac ctc tcc ttc cag gcc act ttt att cgc gcc tgc gaa       336
Pro Glu Asp Asp Leu Ser Phe Gln Ala Thr Phe Ile Arg Ala Cys Glu
                100                 105                 110 gaa gca ggg atc agc gca gaa gct ata gac ccg cag caa gcg cgc att       384
Glu Ala Gly Ile Ser Ala Glu Ala Ile Asp Pro Gln Gln Ala Arg Ile
            115                 120                 125 atc gaa cct gcc gtt aac ccg gca ctg att ggc gcg gtg aaa gtt ccg       432
Ile Glu Pro Ala Val Asn Pro Ala Leu Ile Gly Ala Val Lys Val Pro
        130                 135                 140 gat ggc acc gtt gat cca ttt cgt ctg acc gca gca aac atg ctg gat       480
Asp Gly Thr Val Asp Pro Phe Arg Leu Thr Ala Ala Asn Met Leu Asp
145                 150                 155                 160
```

-continued

| | |
|---|---|
| gcc aaa gaa cac ggt gcc gtt atc ctt acc gct cat gaa gtc acg ggg<br>Ala Lys Glu His Gly Ala Val Ile Leu Thr Ala His Glu Val Thr Gly<br>165 170 175 | 528 |
| ctg att cgt gaa ggc gcg acg gtg tgc ggt gtt cgt gta cgt aac cat<br>Leu Ile Arg Glu Gly Ala Thr Val Cys Gly Val Arg Val Arg Asn His<br>180 185 190 | 576 |
| ctc acc ggc gaa act cag gcc ctt cat gca cct gtc gtg gtt aat gcc<br>Leu Thr Gly Glu Thr Gln Ala Leu His Ala Pro Val Val Val Asn Ala<br>195 200 205 | 624 |
| gct ggg atc tgg ggg caa cac att gcc gaa tat gcc gat ctg cgc att<br>Ala Gly Ile Trp Gly Gln His Ile Ala Glu Tyr Ala Asp Leu Arg Ile<br>210 215 220 | 672 |
| cgc atg ttc ccg gcg aaa gga tcg ctg ctg atc atg gat cac cgc att<br>Arg Met Phe Pro Ala Lys Gly Ser Leu Leu Ile Met Asp His Arg Ile<br>225 230 235 240 | 720 |
| aac cag cat gtg atc aac cgc tgc cgt aaa cct tcc gac gcc gat att<br>Asn Gln His Val Ile Asn Arg Cys Arg Lys Pro Ser Asp Ala Asp Ile<br>245 250 255 | 768 |
| ctg gtg cct ggc gat acc att tcg ctg att ggt acc acc tct tta cgt<br>Leu Val Pro Gly Asp Thr Ile Ser Leu Ile Gly Thr Thr Ser Leu Arg<br>260 265 270 | 816 |
| att gat tac aac gag att gac gat aat cga gtg acg gca gaa gag gtt<br>Ile Asp Tyr Asn Glu Ile Asp Asp Asn Arg Val Thr Ala Glu Glu Val<br>275 280 285 | 864 |
| gat att ctg ctg cgt gaa ggg gaa aaa ctg gcc ccc gtg atg gcg aaa<br>Asp Ile Leu Leu Arg Glu Gly Glu Lys Leu Ala Pro Val Met Ala Lys<br>290 295 300 | 912 |
| acg cgc att ttg cgg gcc tat tct ggc gtg cgc ccg ctg gtt gcc agc<br>Thr Arg Ile Leu Arg Ala Tyr Ser Gly Val Arg Pro Leu Val Ala Ser<br>305 310 315 320 | 960 |
| gat gac gac ccg agc gga cgt aac gtc agc cgt ggc atc gtg ctg ctc<br>Asp Asp Asp Pro Ser Gly Arg Asn Val Ser Arg Gly Ile Val Leu Leu<br>325 330 335 | 1008 |
| gac cat gct gaa cgc gat ggt ctg gac gga ttt atc acc atc acc ggt<br>Asp His Ala Glu Arg Asp Gly Leu Asp Gly Phe Ile Thr Ile Thr Gly<br>340 345 350 | 1056 |
| ggc aaa ctg atg acc tat cgg ctg atg gct gaa tgg gct acc gac gcg<br>Gly Lys Leu Met Thr Tyr Arg Leu Met Ala Glu Trp Ala Thr Asp Ala<br>355 360 365 | 1104 |
| gta tgc cgc aaa ctg ggc aac acg cgc ccc tgt acg act gcc gat ctg<br>Val Cys Arg Lys Leu Gly Asn Thr Arg Pro Cys Thr Thr Ala Asp Leu<br>370 375 380 | 1152 |
| gca ctg cct ggt tca caa gaa ccc gct gaa gtt acc ttg cgt aaa gtc<br>Ala Leu Pro Gly Ser Gln Glu Pro Ala Glu Val Thr Leu Arg Lys Val<br>385 390 395 400 | 1200 |
| atc tcc ctg cct gcc ccg ctg cgc ggt tct gcg gtt tat cgt cat ggc<br>Ile Ser Leu Pro Ala Pro Leu Arg Gly Ser Ala Val Tyr Arg His Gly<br>405 410 415 | 1248 |
| gat cgc acg cct gcc tgg ctg agc gaa ggc cgt ctg cac cgt agc ctg<br>Asp Arg Thr Pro Ala Trp Leu Ser Glu Gly Arg Leu His Arg Ser Leu<br>420 425 430 | 1296 |
| gta tgt gag tgc gaa gcg gta act gcg ggt gaa gtg cag tac gcg gta<br>Val Cys Glu Cys Glu Ala Val Thr Ala Gly Glu Val Gln Tyr Ala Val<br>435 440 445 | 1344 |
| gaa aat tta aac gtt aat agc ctg ctg gat tta cgc cgt cgt acc cgt<br>Glu Asn Leu Asn Val Asn Ser Leu Leu Asp Leu Arg Arg Arg Thr Arg<br>450 455 460 | 1392 |
| gtg ggg atg ggc acc tgc cag ggc gaa ctc tgc gcc tgc cgc gct gcc<br>Val Gly Met Gly Thr Cys Gln Gly Glu Leu Cys Ala Cys Arg Ala Ala | 1440 |

```
                        465                 470                 475                 480
gga ctg ctg caa cgt ttt aac gtc acg acg tcc gcg caa tct atc gag      1488
Gly Leu Leu Gln Arg Phe Asn Val Thr Thr Ser Ala Gln Ser Ile Glu
                    485                 490                 495 caa ctt tcc acc ttc ctt aac gaa cgc tgg aaa ggc gtg caa ccc atc      1536
Gln Leu Ser Thr Phe Leu Asn Glu Arg Trp Lys Gly Val Gln Pro Ile
            500                 505                 510 gcc tgg gga gat gca ctg cgc gaa agc gaa ttt acc cgc tgg gtt tat      1584
Ala Trp Gly Asp Ala Leu Arg Glu Ser Glu Phe Thr Arg Trp Val Tyr
        515                 520                 525 cag gga ttg tgt ggt ctg gag aag gag cag aaa gat gcg ctt tga          1629
Gln Gly Leu Cys Gly Leu Glu Lys Glu Gln Lys Asp Ala Leu
    530                 535                 540
```

<210> SEQ ID NO 2
<211> LENGTH: 542
<212> TYPE: PRT
<213> ORGANISM: Escherichia coli

<400> SEQUENCE: 2

```
Met Lys Thr Arg Asp Ser Gln Ser Ser Asp Val Ile Ile Gly Gly
1               5                   10                  15

Gly Ala Thr Gly Ala Gly Ile Ala Arg Asp Cys Ala Leu Arg Gly Leu
                20                  25                  30

Arg Val Ile Leu Val Glu Arg His Asp Ile Ala Thr Gly Ala Thr Gly
            35                  40                  45

Arg Asn His Gly Leu Leu His Ser Gly Ala Arg Tyr Ala Val Thr Asp
        50                  55                  60

Ala Glu Ser Ala Arg Glu Cys Ile Ser Glu Asn Gln Ile Leu Lys Arg
65                  70                  75                  80

Ile Ala Arg His Cys Val Glu Pro Thr Asn Gly Leu Phe Ile Thr Leu
                85                  90                  95

Pro Glu Asp Asp Leu Ser Phe Gln Ala Thr Phe Ile Arg Ala Cys Glu
            100                 105                 110

Glu Ala Gly Ile Ser Ala Glu Ala Ile Asp Pro Gln Gln Ala Arg Ile
        115                 120                 125

Ile Glu Pro Ala Val Asn Pro Ala Leu Ile Gly Ala Val Lys Val Pro
    130                 135                 140

Asp Gly Thr Val Asp Pro Phe Arg Leu Thr Ala Ala Asn Met Leu Asp
145                 150                 155                 160

Ala Lys Glu His Gly Ala Val Ile Leu Thr Ala His Glu Val Thr Gly
                165                 170                 175

Leu Ile Arg Glu Gly Ala Thr Val Cys Gly Val Arg Val Arg Asn His
            180                 185                 190

Leu Thr Gly Glu Thr Gln Ala Leu His Ala Pro Val Val Asn Ala
        195                 200                 205

Ala Gly Ile Trp Gly Gln His Ile Ala Glu Tyr Ala Asp Leu Arg Ile
    210                 215                 220

Arg Met Phe Pro Ala Lys Gly Ser Leu Leu Ile Met Asp His Arg Ile
225                 230                 235                 240

Asn Gln His Val Ile Asn Arg Cys Arg Lys Pro Ser Asp Ala Asp Ile
                245                 250                 255

Leu Val Pro Gly Asp Thr Ile Ser Leu Ile Gly Thr Thr Ser Leu Arg
            260                 265                 270

Ile Asp Tyr Asn Glu Ile Asp Asp Asn Arg Val Thr Ala Glu Glu Val
        275                 280                 285
```

Asp Ile Leu Leu Arg Glu Gly Glu Lys Leu Ala Pro Val Met Ala Lys
290                 295                 300

Thr Arg Ile Leu Arg Ala Tyr Ser Gly Val Arg Pro Leu Val Ala Ser
305                 310                 315                 320

Asp Asp Asp Pro Ser Gly Arg Asn Val Ser Arg Gly Ile Val Leu Leu
            325                 330                 335

Asp His Ala Glu Arg Asp Gly Leu Asp Gly Phe Ile Thr Ile Thr Gly
            340                 345                 350

Gly Lys Leu Met Thr Tyr Arg Leu Met Ala Glu Trp Ala Thr Asp Ala
        355                 360                 365

Val Cys Arg Lys Leu Gly Asn Thr Arg Pro Cys Thr Thr Ala Asp Leu
370                 375                 380

Ala Leu Pro Gly Ser Gln Glu Pro Ala Glu Val Thr Leu Arg Lys Val
385                 390                 395                 400

Ile Ser Leu Pro Ala Pro Leu Arg Gly Ser Ala Val Tyr Arg His Gly
                405                 410                 415

Asp Arg Thr Pro Ala Trp Leu Ser Glu Gly Arg Leu His Arg Ser Leu
            420                 425                 430

Val Cys Glu Cys Glu Ala Val Thr Ala Gly Val Gln Tyr Ala Val
        435                 440                 445

Glu Asn Leu Asn Val Asn Ser Leu Leu Asp Leu Arg Arg Arg Thr Arg
450                 455                 460

Val Gly Met Gly Thr Cys Gln Gly Glu Leu Cys Ala Cys Arg Ala Ala
465                 470                 475                 480

Gly Leu Leu Gln Arg Phe Asn Val Thr Thr Ser Ala Gln Ser Ile Glu
                485                 490                 495

Gln Leu Ser Thr Phe Leu Asn Glu Arg Trp Lys Gly Val Gln Pro Ile
            500                 505                 510

Ala Trp Gly Asp Ala Leu Arg Glu Ser Glu Phe Thr Arg Trp Val Tyr
        515                 520                 525

Gln Gly Leu Cys Gly Leu Glu Lys Glu Gln Lys Asp Ala Leu
    530                 535                 540

<210> SEQ ID NO 3
<211> LENGTH: 1260
<212> TYPE: DNA
<213> ORGANISM: Escherichia coli
<220> FEATURE:
<221> NAME/KEY: CDS
<222> LOCATION: (1)..(1260)
<223> OTHER INFORMATION: glpB coding region

<400> SEQUENCE: 3

```
atg cgc ttt gat act gtc att atg ggc ggc ggc ctc gcc gga tta ctc      48
Met Arg Phe Asp Thr Val Ile Met Gly Gly Gly Leu Ala Gly Leu Leu
1               5                   10                  15 tgt ggc ctg caa ctg caa aaa cac ggc ctg cgc tgt gcc att gtc act      96
Cys Gly Leu Gln Leu Gln Lys His Gly Leu Arg Cys Ala Ile Val Thr
            20                  25                  30 cgt ggt caa agc gca ctg cat ttc tca tcc gga tcg ctg gat ttg ctg     144
Arg Gly Gln Ser Ala Leu His Phe Ser Ser Gly Ser Leu Asp Leu Leu
        35                  40                  45 agc cat ctg cca gat ggt caa ccg gtg aca gac att cac agt gga ctg     192
Ser His Leu Pro Asp Gly Gln Pro Val Thr Asp Ile His Ser Gly Leu
    50                  55                  60 gaa tct ttg cgt cag cag gca cca gcc cat cct tac tcc ctt ctc gag     240
Glu Ser Leu Arg Gln Gln Ala Pro Ala His Pro Tyr Ser Leu Leu Glu
```

```
                 65                  70                  75                  80
cca caa cgc gtg ctc gat ctc gct tgc cag gcg cag gca tta atc gct       288
Pro Gln Arg Val Leu Asp Leu Ala Cys Gln Ala Gln Ala Leu Ile Ala
                     85                  90                  95 gaa agc ggt gcg caa ttg cag ggc agc gta gaa ctt gct cac cag cgg       336
Glu Ser Gly Ala Gln Leu Gln Gly Ser Val Glu Leu Ala His Gln Arg
                100                 105                 110 gtt acg ccg ctc ggc act ctg cgc tct acc tgg cta agt tcg cca gaa       384
Val Thr Pro Leu Gly Thr Leu Arg Ser Thr Trp Leu Ser Ser Pro Glu
            115                 120                 125 gtc ccc gtc tgg ccg ctg ccc gcg aag aaa ata tgt gta gtg gga att       432
Val Pro Val Trp Pro Leu Pro Ala Lys Lys Ile Cys Val Val Gly Ile
        130                 135                 140 agc ggc ctg atg gat ttt cag gcg cac ctt gcg gca gct tcg ttg cgt       480
Ser Gly Leu Met Asp Phe Gln Ala His Leu Ala Ala Ala Ser Leu Arg
145                 150                 155                 160 gaa ctc ggc ctt gcc gtt gaa acc gca gaa ata gag ctg ccg gaa ctg       528
Glu Leu Gly Leu Ala Val Glu Thr Ala Glu Ile Glu Leu Pro Glu Leu
                165                 170                 175 gat gtg ctg cgc aat aac gcc acc gaa ttt cgc gcg gtg aat atc gcc       576
Asp Val Leu Arg Asn Asn Ala Thr Glu Phe Arg Ala Val Asn Ile Ala
                180                 185                 190 cgt ttc ctt gat aat gaa gaa aac tgg ccg ctg tta ctt gat gcg ctt       624
Arg Phe Leu Asp Asn Glu Glu Asn Trp Pro Leu Leu Leu Asp Ala Leu
            195                 200                 205 att cct gtc gcc aat acc tgc gaa atg atc ctg atg ccc gcc tgc ttc       672
Ile Pro Val Ala Asn Thr Cys Glu Met Ile Leu Met Pro Ala Cys Phe
        210                 215                 220 ggt ctg gcc gat gac aaa ctg tgg cgt tgg ttg aat gaa aaa cta cct       720
Gly Leu Ala Asp Asp Lys Leu Trp Arg Trp Leu Asn Glu Lys Leu Pro
225                 230                 235                 240 tgt tca ctg atg ctt ttg cca acg ctg ccg cct tcc gtg ctg ggc att       768
Cys Ser Leu Met Leu Leu Pro Thr Leu Pro Pro Ser Val Leu Gly Ile
                245                 250                 255 cgt ctg caa aac cag tta cag cgc cag ttt gtg cgc cag ggt ggc gtg       816
Arg Leu Gln Asn Gln Leu Gln Arg Gln Phe Val Arg Gln Gly Gly Val
                260                 265                 270 tgg atg ccg ggc gat gaa gtg aaa aaa gtg acc tgt aaa aat ggc gta       864
Trp Met Pro Gly Asp Glu Val Lys Lys Val Thr Cys Lys Asn Gly Val
            275                 280                 285 gtg aac gaa atc tgg acc cgc aat cac gcc gat att ccg cta cgt cca       912
Val Asn Glu Ile Trp Thr Arg Asn His Ala Asp Ile Pro Leu Arg Pro
        290                 295                 300 cgt ttc gcg gtt ctc gcc agc ggc agt ttc ttt agt ggc gga ctg gta       960
Arg Phe Ala Val Leu Ala Ser Gly Ser Phe Phe Ser Gly Gly Leu Val
305                 310                 315                 320 gcg gaa cgt aac ggc att cga gag ccg att ctc ggc ctt gat gtg cta      1008
Ala Glu Arg Asn Gly Ile Arg Glu Pro Ile Leu Gly Leu Asp Val Leu
                325                 330                 335 caa acc gcc acg cgg ggt gaa tgg tat aag gga gat ttt ttt gcg ccg      1056
Gln Thr Ala Thr Arg Gly Glu Trp Tyr Lys Gly Asp Phe Phe Ala Pro
                340                 345                 350 caa ccg tgg cag cag ttc ggt gta acc act gat gag acg cta cgc ccg      1104
Gln Pro Trp Gln Gln Phe Gly Val Thr Thr Asp Glu Thr Leu Arg Pro
            355                 360                 365 tca cag gca ggg caa acc att gaa aac ctg ttt gcc atc ggt tcg gtg      1152
Ser Gln Ala Gly Gln Thr Ile Glu Asn Leu Phe Ala Ile Gly Ser Val
        370                 375                 380 ctg ggc gga ttt gat ccc atc gcc cag gga tgc ggc ggc ggt gtt tgt      1200
```

-continued

```
Leu Gly Gly Phe Asp Pro Ile Ala Gln Gly Cys Gly Gly Val Cys
385                 390                 395                 400 gcc gtc agt gct tta cat gcc gct caa cag att gcc caa cgc gca gga    1248
Ala Val Ser Ala Leu His Ala Ala Gln Gln Ile Ala Gln Arg Ala Gly
            405                 410                 415 ggc caa caa tga                                                    1260
Gly Gln Gln <210> SEQ ID NO 4
<211> LENGTH: 419
<212> TYPE: PRT
<213> ORGANISM: Escherichia coli

<400> SEQUENCE: 4

Met Arg Phe Asp Thr Val Ile Met Gly Gly Gly Leu Ala Gly Leu Leu
1               5                   10                  15

Cys Gly Leu Gln Leu Gln Lys His Gly Leu Arg Cys Ala Ile Val Thr
            20                  25                  30

Arg Gly Gln Ser Ala Leu His Phe Ser Ser Gly Ser Leu Asp Leu Leu
        35                  40                  45

Ser His Leu Pro Asp Gly Gln Pro Val Thr Asp Ile His Ser Gly Leu
    50                  55                  60

Glu Ser Leu Arg Gln Gln Ala Pro Ala His Pro Tyr Ser Leu Leu Glu
65                  70                  75                  80

Pro Gln Arg Val Leu Asp Leu Ala Cys Gln Ala Gln Ala Leu Ile Ala
                85                  90                  95

Glu Ser Gly Ala Gln Leu Gln Gly Ser Val Glu Leu Ala His Gln Arg
            100                 105                 110

Val Thr Pro Leu Gly Thr Leu Arg Ser Thr Trp Leu Ser Ser Pro Glu
        115                 120                 125

Val Pro Val Trp Pro Leu Pro Ala Lys Lys Ile Cys Val Val Gly Ile
    130                 135                 140

Ser Gly Leu Met Asp Phe Gln Ala His Leu Ala Ala Ala Ser Leu Arg
145                 150                 155                 160

Glu Leu Gly Leu Ala Val Glu Thr Ala Glu Ile Glu Leu Pro Glu Leu
                165                 170                 175

Asp Val Leu Arg Asn Asn Ala Thr Glu Phe Arg Ala Val Asn Ile Ala
            180                 185                 190

Arg Phe Leu Asp Asn Glu Glu Asn Trp Pro Leu Leu Leu Asp Ala Leu
        195                 200                 205

Ile Pro Val Ala Asn Thr Cys Glu Met Ile Leu Met Pro Ala Cys Phe
    210                 215                 220

Gly Leu Ala Asp Asp Lys Leu Trp Arg Trp Leu Asn Glu Lys Leu Pro
225                 230                 235                 240

Cys Ser Leu Met Leu Leu Pro Thr Leu Pro Pro Ser Val Leu Gly Ile
                245                 250                 255

Arg Leu Gln Asn Gln Leu Gln Arg Gln Phe Val Arg Gln Gly Gly Val
            260                 265                 270

Trp Met Pro Gly Asp Glu Val Lys Lys Val Thr Cys Lys Asn Gly Val
        275                 280                 285

Val Asn Glu Ile Trp Thr Arg Asn His Ala Asp Ile Pro Leu Arg Pro
    290                 295                 300

Arg Phe Ala Val Leu Ala Ser Gly Ser Phe Phe Ser Gly Gly Leu Val
305                 310                 315                 320

Ala Glu Arg Asn Gly Ile Arg Glu Pro Ile Leu Gly Leu Asp Val Leu
```

```
                          325                 330                 335
Gln Thr Ala Thr Arg Gly Glu Trp Tyr Lys Gly Asp Phe Phe Ala Pro
            340                 345                 350

Gln Pro Trp Gln Gln Phe Gly Val Thr Thr Asp Glu Thr Leu Arg Pro
            355                 360                 365

Ser Gln Ala Gly Gln Thr Ile Glu Asn Leu Phe Ala Ile Gly Ser Val
            370                 375                 380

Leu Gly Gly Phe Asp Pro Ile Ala Gln Gly Cys Gly Gly Val Cys
385                 390                 395                 400

Ala Val Ser Ala Leu His Ala Ala Gln Gln Ile Ala Gln Arg Ala Gly
                405                 410                 415

Gly Gln Gln

<210> SEQ ID NO 5
<211> LENGTH: 1191
<212> TYPE: DNA
<213> ORGANISM: Escherichia coli
<220> FEATURE:
<221> NAME/KEY: CDS
<222> LOCATION: (1)..(1191)
<223> OTHER INFORMATION: glpC coding region

<400> SEQUENCE: 5 atg aat gac acc agc ttc gaa aac tgc att aag tgc acc gtc tgc acc       48
Met Asn Asp Thr Ser Phe Glu Asn Cys Ile Lys Cys Thr Val Cys Thr
1               5                  10                  15 acc gcc tgc ccg gtg agc cgg gtg aat ccc ggt tat cca ggg cca aaa       96
Thr Ala Cys Pro Val Ser Arg Val Asn Pro Gly Tyr Pro Gly Pro Lys
                20                  25                  30 caa gcc ggg ccg gat ggc gag cgt ctg cgt ttg aaa gat ggc gca ctg      144
Gln Ala Gly Pro Asp Gly Glu Arg Leu Arg Leu Lys Asp Gly Ala Leu
            35                  40                  45 tat gac gag gcg ctg aaa tat tgc atc aac tgc aaa cgt tgt gaa gtc      192
Tyr Asp Glu Ala Leu Lys Tyr Cys Ile Asn Cys Lys Arg Cys Glu Val
        50                  55                  60 gcc tgc ccg tcc gat gtg aag att ggc gat att atc cag cgc gcg cgg      240
Ala Cys Pro Ser Asp Val Lys Ile Gly Asp Ile Ile Gln Arg Ala Arg
65                  70                  75                  80 gcg aaa tat gac acc acg cgc ccg tcg ctg cgt aat ttt gtg ttg agt      288
Ala Lys Tyr Asp Thr Thr Arg Pro Ser Leu Arg Asn Phe Val Leu Ser
                85                  90                  95 cat acc gac ctg atg ggt agc gtt tcc acg ccg ttc gca cca atc gtc      336
His Thr Asp Leu Met Gly Ser Val Ser Thr Pro Phe Ala Pro Ile Val
            100                 105                 110 aac acc gct acc tcg ctg aaa ccg gtg cgg cag ctg ctt gat gcg gcg      384
Asn Thr Ala Thr Ser Leu Lys Pro Val Arg Gln Leu Leu Asp Ala Ala
        115                 120                 125 tta aaa atc gat cat cgc cgc acg cta ccg aaa tac tcc ttc ggc acg      432
Leu Lys Ile Asp His Arg Arg Thr Leu Pro Lys Tyr Ser Phe Gly Thr
    130                 135                 140 ttc cgt cgc tgg tat cgc agc gtg gcg gct cag caa gca caa tat aaa      480
Phe Arg Arg Trp Tyr Arg Ser Val Ala Ala Gln Gln Ala Gln Tyr Lys
145                 150                 155                 160 gac cag gtc gct ttc ttt cac ggc tgc ttc gtt aac tac aac cat ccg      528
Asp Gln Val Ala Phe Phe His Gly Cys Phe Val Asn Tyr Asn His Pro
                165                 170                 175 cag tta ggt aaa gat tta att aaa gtg ctc aac gca atg ggt acc ggt      576
Gln Leu Gly Lys Asp Leu Ile Lys Val Leu Asn Ala Met Gly Thr Gly
            180                 185                 190
```

```
gta caa ctg ctc agc aaa gaa aaa tgc tgc ggc gta ccg cta atc gcc     624
Val Gln Leu Leu Ser Lys Glu Lys Cys Cys Gly Val Pro Leu Ile Ala
        195                 200                 205 aac ggc ttt acc gat aaa gca cgc aaa cag gca att acg aat gta gag     672
Asn Gly Phe Thr Asp Lys Ala Arg Lys Gln Ala Ile Thr Asn Val Glu
210                 215                 220 tcg atc cgc gaa gct gtg gga gta aaa ggc att ccg gtg att gcc acc     720
Ser Ile Arg Glu Ala Val Gly Val Lys Gly Ile Pro Val Ile Ala Thr
225                 230                 235                 240 tcc tca acc tgt aca ttt gcc ctg cgc gac gaa tac ccg gaa gtg ctg     768
Ser Ser Thr Cys Thr Phe Ala Leu Arg Asp Glu Tyr Pro Glu Val Leu
                245                 250                 255 aat gtc gac aac aaa ggc ttg cgc gat cat atc gaa ctg gca acc cgc     816
Asn Val Asp Asn Lys Gly Leu Arg Asp His Ile Glu Leu Ala Thr Arg
            260                 265                 270 tgg ctg tgg cgc aag ctg gac gaa ggc aaa acg tta ccg ctg aaa ccg     864
Trp Leu Trp Arg Lys Leu Asp Glu Gly Lys Thr Leu Pro Leu Lys Pro
        275                 280                 285 ctg ccg ctg aaa gtg gtt tat cac act ccg tgc cat atg gaa aaa atg     912
Leu Pro Leu Lys Val Val Tyr His Thr Pro Cys His Met Glu Lys Met
    290                 295                 300 ggc tgg acg ctc tac acc ctg gag ctg ttg cgt aac atc ccg ggg ctt     960
Gly Trp Thr Leu Tyr Thr Leu Glu Leu Leu Arg Asn Ile Pro Gly Leu
305                 310                 315                 320 gag tta acg gtg ctg gat tcc cag tgc tgc ggt att gcg ggt act tac    1008
Glu Leu Thr Val Leu Asp Ser Gln Cys Cys Gly Ile Ala Gly Thr Tyr
                325                 330                 335 ggt ttc aaa aaa gag aac tac ccc acc tca caa gcc atc ggc gca cca    1056
Gly Phe Lys Lys Glu Asn Tyr Pro Thr Ser Gln Ala Ile Gly Ala Pro
            340                 345                 350 ctg ttc cgc cag ata gaa gaa agc ggc gca gat ctg gtg gtc acc gac    1104
Leu Phe Arg Gln Ile Glu Glu Ser Gly Ala Asp Leu Val Val Thr Asp
        355                 360                 365 tgc gaa acc tgt aaa tgg cag att gag atg tcc aca agt ctt cgc tgc    1152
Cys Glu Thr Cys Lys Trp Gln Ile Glu Met Ser Thr Ser Leu Arg Cys
    370                 375                 380 gaa cat ccg att acg cta ctg gcc cag gcg ctg gct taa                1191
Glu His Pro Ile Thr Leu Leu Ala Gln Ala Leu Ala
385                 390                 395
```

<210> SEQ ID NO 6
<211> LENGTH: 396
<212> TYPE: PRT
<213> ORGANISM: Escherichia coli

<400> SEQUENCE: 6

```
Met Asn Asp Thr Ser Phe Glu Asn Cys Ile Lys Cys Thr Val Cys Thr
1               5                   10                  15

Thr Ala Cys Pro Val Ser Arg Val Asn Pro Gly Tyr Pro Gly Pro Lys
            20                  25                  30

Gln Ala Gly Pro Asp Gly Glu Arg Leu Arg Leu Lys Asp Gly Ala Leu
        35                  40                  45

Tyr Asp Glu Ala Leu Lys Tyr Cys Ile Asn Cys Lys Arg Cys Glu Val
    50                  55                  60

Ala Cys Pro Ser Asp Val Lys Ile Gly Asp Ile Gln Arg Ala Arg
65                  70                  75                  80

Ala Lys Tyr Asp Thr Thr Arg Pro Ser Leu Arg Asn Phe Val Leu Ser
                85                  90                  95

His Thr Asp Leu Met Gly Ser Val Ser Thr Pro Phe Ala Pro Ile Val
```

```
                100               105               110
Asn Thr Ala Thr Ser Leu Lys Pro Val Arg Gln Leu Leu Asp Ala Ala
            115                 120                 125

Leu Lys Ile Asp His Arg Arg Thr Leu Pro Lys Tyr Ser Phe Gly Thr
        130                 135                 140

Phe Arg Arg Trp Tyr Arg Ser Val Ala Ala Gln Ala Gln Tyr Lys
145                 150                 155                 160

Asp Gln Val Ala Phe His Gly Cys Phe Val Asn Tyr Asn His Pro
                165                 170                 175

Gln Leu Gly Lys Asp Leu Ile Lys Val Leu Asn Ala Met Gly Thr Gly
            180                 185                 190

Val Gln Leu Leu Ser Lys Glu Lys Cys Cys Gly Val Pro Leu Ile Ala
        195                 200                 205

Asn Gly Phe Thr Asp Lys Ala Arg Lys Gln Ala Ile Thr Asn Val Glu
    210                 215                 220

Ser Ile Arg Glu Ala Val Gly Val Lys Gly Ile Pro Val Ile Ala Thr
225                 230                 235                 240

Ser Ser Thr Cys Thr Phe Ala Leu Arg Asp Glu Tyr Pro Glu Val Leu
                245                 250                 255

Asn Val Asp Asn Lys Gly Leu Arg Asp His Ile Glu Leu Ala Thr Arg
            260                 265                 270

Trp Leu Trp Arg Lys Leu Asp Glu Gly Lys Thr Leu Pro Leu Lys Pro
        275                 280                 285

Leu Pro Leu Lys Val Val Tyr His Thr Pro Cys His Met Glu Lys Met
    290                 295                 300

Gly Trp Thr Leu Tyr Thr Leu Glu Leu Leu Arg Asn Ile Pro Gly Leu
305                 310                 315                 320

Glu Leu Thr Val Leu Asp Ser Gln Cys Cys Gly Ile Ala Gly Thr Tyr
                325                 330                 335

Gly Phe Lys Lys Glu Asn Tyr Pro Thr Ser Gln Ala Ile Gly Ala Pro
            340                 345                 350

Leu Phe Arg Gln Ile Glu Glu Ser Gly Ala Asp Leu Val Val Thr Asp
        355                 360                 365

Cys Glu Thr Cys Lys Trp Gln Ile Glu Met Ser Thr Ser Leu Arg Cys
    370                 375                 380

Glu His Pro Ile Thr Leu Leu Ala Gln Ala Leu Ala
385                 390                 395

<210> SEQ ID NO 7
<211> LENGTH: 1506
<212> TYPE: DNA
<213> ORGANISM: Escherichia coli
<220> FEATURE:
<221> NAME/KEY: CDS
<222> LOCATION: (1)..(1506)
<223> OTHER INFORMATION: glpD coding region

<400> SEQUENCE: 7 atg gaa acc aaa gat ctg att gtg ata ggg ggc ggc atc aat ggt gct      48
Met Glu Thr Lys Asp Leu Ile Val Ile Gly Gly Gly Ile Asn Gly Ala
1               5                   10                  15 ggt atc gcg gca gac gcc gct gga cgc ggt tta tcc gtg ctg atg ctg      96
Gly Ile Ala Ala Asp Ala Ala Gly Arg Gly Leu Ser Val Leu Met Leu
            20                  25                  30 gag gcg cag gat ctc gct tgc gcg acc tct tcc gcc agt tca aaa ctc     144
Glu Ala Gln Asp Leu Ala Cys Ala Thr Ser Ser Ala Ser Ser Lys Leu
        35                  40                  45
```

-continued

| | | |
|---|---|---|
| att cac ggt ggc ctg cgc tac ctt gag cac tat gaa ttc cgc ctg gtc<br>Ile His Gly Gly Leu Arg Tyr Leu Glu His Tyr Glu Phe Arg Leu Val<br>50            55                  60 | | 192 |
| agc gag gcg ctg gct gaa cgt gaa gtg ctg ctg aaa atg gcc ccg cat<br>Ser Glu Ala Leu Ala Glu Arg Glu Val Leu Leu Lys Met Ala Pro His<br>65              70                  75                  80 | | 240 |
| atc gcc ttc ccg atg cgt ttt cgc ctg cca cat cgt ccg cat ctg cgc<br>Ile Ala Phe Pro Met Arg Phe Arg Leu Pro His Arg Pro His Leu Arg<br>85                  90                  95 | | 288 |
| ccg gcg tgg atg att cgc att ggt ctg ttt atg tac gat cat ctg ggt<br>Pro Ala Trp Met Ile Arg Ile Gly Leu Phe Met Tyr Asp His Leu Gly<br>100                105                  110 | | 336 |
| aaa cgc acc agc ttg ccg gga tca act ggt ttg cgt ttt ggc gca aat<br>Lys Arg Thr Ser Leu Pro Gly Ser Thr Gly Leu Arg Phe Gly Ala Asn<br>115                120                  125 | | 384 |
| tca gtg tta aaa ccg gaa att aag cgc gga ttc gaa tat tct gac tgt<br>Ser Val Leu Lys Pro Glu Ile Lys Arg Gly Phe Glu Tyr Ser Asp Cys<br>130                135                  140 | | 432 |
| tgg gta gac gac gcc cgt ctg gta ctc gcc aac gcc cag atg gtg gtg<br>Trp Val Asp Asp Ala Arg Leu Val Leu Ala Asn Ala Gln Met Val Val<br>145            150                  155                  160 | | 480 |
| cgt aaa ggc ggc gaa gtg ctt act cgg act cgc gcc acc tct gct cgc<br>Arg Lys Gly Gly Glu Val Leu Thr Arg Thr Arg Ala Thr Ser Ala Arg<br>165                170                  175 | | 528 |
| cgc gaa aac ggc ctg tgg att gtg gaa gcg gaa gat atc gat acc ggc<br>Arg Glu Asn Gly Leu Trp Ile Val Glu Ala Glu Asp Ile Asp Thr Gly<br>180                185                  190 | | 576 |
| aaa aaa tat agc tgg caa gcg cgc ggc ttg gtt aac gcc acc ggc ccg<br>Lys Lys Tyr Ser Trp Gln Ala Arg Gly Leu Val Asn Ala Thr Gly Pro<br>195                200                  205 | | 624 |
| tgg gtg aaa cag ttc ttc gac gac ggg atg cat ctg cct tcg cct tat<br>Trp Val Lys Gln Phe Phe Asp Asp Gly Met His Leu Pro Ser Pro Tyr<br>210                215                  220 | | 672 |
| ggc att cgc ctg atc aaa ggc agc cat att gtg gtg ccg cgc gtg cat<br>Gly Ile Arg Leu Ile Lys Gly Ser His Ile Val Val Pro Arg Val His<br>225            230                  235                  240 | | 720 |
| acc cag aag caa gcc tac att ctg caa aac gaa gat aaa cgt att gtg<br>Thr Gln Lys Gln Ala Tyr Ile Leu Gln Asn Glu Asp Lys Arg Ile Val<br>245                250                  255 | | 768 |
| ttc gtg atc ccg tgg atg gac gag ttt tcc atc atc ggc act acc gat<br>Phe Val Ile Pro Trp Met Asp Glu Phe Ser Ile Ile Gly Thr Thr Asp<br>260                265                  270 | | 816 |
| gtc gag tac aaa ggc gat ccg aaa gcg gtg aag att gaa gag agt gaa<br>Val Glu Tyr Lys Gly Asp Pro Lys Ala Val Lys Ile Glu Glu Ser Glu<br>275                280                  285 | | 864 |
| atc aat tac ctg ctg aat gtg tat aac acg cac ttt aaa aag cag tta<br>Ile Asn Tyr Leu Leu Asn Val Tyr Asn Thr His Phe Lys Lys Gln Leu<br>290                295                  300 | | 912 |
| agc cgt gac gat atc gtc tgg acc tac tcc ggt gtg cgt ccg ctg tgt<br>Ser Arg Asp Asp Ile Val Trp Thr Tyr Ser Gly Val Arg Pro Leu Cys<br>305            310                  315                  320 | | 960 |
| gat gat gag tcc gac tcg ccg cag gct att acc cgt gat tac acc ctt<br>Asp Asp Glu Ser Asp Ser Pro Gln Ala Ile Thr Arg Asp Tyr Thr Leu<br>325                330                  335 | | 1008 |
| gat att cat gat gaa aat ggc aaa gca ccg ctg ctg tcg gta ttc ggc<br>Asp Ile His Asp Glu Asn Gly Lys Ala Pro Leu Leu Ser Val Phe Gly<br>340                345                  350 | | 1056 |
| ggt aag ctg acc acc tac cga aaa ctg gcg gaa cat gcg ctg gaa aaa<br>Gly Lys Leu Thr Thr Tyr Arg Lys Leu Ala Glu His Ala Leu Glu Lys | | 1104 |

```
                  355                 360                 365
cta acg ccg tat tat cag ggt att ggc ccg gca tgg acg aaa gag agt    1152
Leu Thr Pro Tyr Tyr Gln Gly Ile Gly Pro Ala Trp Thr Lys Glu Ser
    370                 375                 380 gtg cta ccg ggt ggc gcc att gaa ggc gac cgc gac gat tat gcc gct    1200
Val Leu Pro Gly Gly Ala Ile Glu Gly Asp Arg Asp Asp Tyr Ala Ala
385                 390                 395                 400 cgc ctg cgc cgc cgc tat ccg ttc ctg act gaa tcg ctg gcg cgt cat    1248
Arg Leu Arg Arg Arg Tyr Pro Phe Leu Thr Glu Ser Leu Ala Arg His
                405                 410                 415 tac gct cgc act tac ggc agc aac agc gag ctg ctc ggc aat gcg        1296
Tyr Ala Arg Thr Tyr Gly Ser Asn Ser Glu Leu Leu Leu Gly Asn Ala
            420                 425                 430 gga acg gta agc gat ctc ggg gaa gat ttc ggt cat gag ttc tac gaa    1344
Gly Thr Val Ser Asp Leu Gly Glu Asp Phe Gly His Glu Phe Tyr Glu
        435                 440                 445 gcg gag ctg aaa tac ctg gtg gat cac gaa tgg gtc cgc cgc gcc gac    1392
Ala Glu Leu Lys Tyr Leu Val Asp His Glu Trp Val Arg Arg Ala Asp
    450                 455                 460 gac gcc ctg tgg cgt cgc aca aaa caa ggc atg tgg cta aat gcg gat    1440
Asp Ala Leu Trp Arg Arg Thr Lys Gln Gly Met Trp Leu Asn Ala Asp
465                 470                 475                 480 caa caa tct cgt gtg agt cag tgg ctg gtg gag tat acg cag cag agg    1488
Gln Gln Ser Arg Val Ser Gln Trp Leu Val Glu Tyr Thr Gln Gln Arg
                485                 490                 495 tta tcg ctg gcg tcg taa                                            1506
Leu Ser Leu Ala Ser
            500

<210> SEQ ID NO 8
<211> LENGTH: 501
<212> TYPE: PRT
<213> ORGANISM: Escherichia coli

<400> SEQUENCE: 8

Met Glu Thr Lys Asp Leu Ile Val Ile Gly Gly Gly Ile Asn Gly Ala
1               5                   10                  15

Gly Ile Ala Ala Asp Ala Ala Gly Arg Gly Leu Ser Val Leu Met Leu
            20                  25                  30

Glu Ala Gln Asp Leu Ala Cys Ala Thr Ser Ser Ala Ser Ser Lys Leu
        35                  40                  45

Ile His Gly Gly Leu Arg Tyr Leu Glu His Tyr Glu Phe Arg Leu Val
    50                  55                  60

Ser Glu Ala Leu Ala Glu Arg Glu Val Leu Leu Lys Met Ala Pro His
65                  70                  75                  80

Ile Ala Phe Pro Met Arg Phe Arg Leu Pro His Arg Pro His Leu Arg
                85                  90                  95

Pro Ala Trp Met Ile Arg Ile Gly Leu Phe Met Tyr Asp His Leu Gly
            100                 105                 110

Lys Arg Thr Ser Leu Pro Gly Ser Thr Gly Leu Arg Phe Gly Ala Asn
        115                 120                 125

Ser Val Leu Lys Pro Glu Ile Lys Arg Gly Phe Glu Tyr Ser Asp Cys
    130                 135                 140

Trp Val Asp Asp Ala Arg Leu Val Leu Ala Asn Ala Gln Met Val Val
145                 150                 155                 160

Arg Lys Gly Gly Glu Val Leu Thr Arg Thr Arg Ala Thr Ser Ala Arg
                165                 170                 175
```

```
Arg Glu Asn Gly Leu Trp Ile Val Glu Ala Glu Asp Ile Asp Thr Gly
            180                 185                 190
Lys Lys Tyr Ser Trp Gln Ala Arg Gly Leu Val Asn Ala Thr Gly Pro
        195                 200                 205
Trp Val Lys Gln Phe Phe Asp Asp Gly Met His Leu Pro Ser Pro Tyr
    210                 215                 220
Gly Ile Arg Leu Ile Lys Gly Ser His Ile Val Val Pro Arg Val His
225                 230                 235                 240
Thr Gln Lys Gln Ala Tyr Ile Leu Gln Asn Glu Asp Lys Arg Ile Val
                245                 250                 255
Phe Val Ile Pro Trp Met Asp Glu Phe Ser Ile Ile Gly Thr Thr Asp
            260                 265                 270
Val Glu Tyr Lys Gly Asp Pro Lys Ala Val Lys Ile Glu Glu Ser Glu
        275                 280                 285
Ile Asn Tyr Leu Leu Asn Val Tyr Asn Thr His Phe Lys Lys Gln Leu
    290                 295                 300
Ser Arg Asp Asp Ile Val Trp Thr Tyr Ser Gly Val Arg Pro Leu Cys
305                 310                 315                 320
Asp Asp Glu Ser Asp Ser Pro Gln Ala Ile Thr Arg Asp Tyr Thr Leu
                325                 330                 335
Asp Ile His Asp Glu Asn Gly Lys Ala Pro Leu Leu Ser Val Phe Gly
            340                 345                 350
Gly Lys Leu Thr Thr Tyr Arg Lys Leu Ala Glu His Ala Leu Glu Lys
        355                 360                 365
Leu Thr Pro Tyr Gln Gly Ile Gly Pro Ala Trp Thr Lys Glu Ser
    370                 375                 380
Val Leu Pro Gly Gly Ala Ile Glu Gly Asp Arg Asp Asp Tyr Ala Ala
385                 390                 395                 400
Arg Leu Arg Arg Arg Tyr Pro Phe Leu Thr Glu Ser Leu Ala Arg His
                405                 410                 415
Tyr Ala Arg Thr Tyr Gly Ser Asn Ser Glu Leu Leu Gly Asn Ala
            420                 425                 430
Gly Thr Val Ser Asp Leu Gly Glu Asp Phe Gly His Glu Phe Tyr Glu
        435                 440                 445
Ala Glu Leu Lys Tyr Leu Val Asp His Glu Trp Val Arg Arg Ala Asp
    450                 455                 460
Asp Ala Leu Trp Arg Arg Thr Lys Gln Gly Met Trp Leu Asn Ala Asp
465                 470                 475                 480
Gln Gln Ser Arg Val Ser Gln Trp Leu Val Glu Tyr Thr Gln Gln Arg
                485                 490                 495
Leu Ser Leu Ala Ser
            500

<210> SEQ ID NO 9
<211> LENGTH: 327
<212> TYPE: DNA
<213> ORGANISM: Escherichia coli
<220> FEATURE:
<221> NAME/KEY: CDS
<222> LOCATION: (1)..(327)
<223> OTHER INFORMATION: glpE coding region

<400> SEQUENCE: 9 atg gat cag ttc gaa tgt att aac gtt gcc gac gcg cac cag aag ttg      48
Met Asp Gln Phe Glu Cys Ile Asn Val Ala Asp Ala His Gln Lys Leu
1               5                   10                  15
```

```
cag gaa aaa gag gcg gtg ctg gtc gat att cgc gat cca cag agt ttc    96
Gln Glu Lys Glu Ala Val Leu Val Asp Ile Arg Asp Pro Gln Ser Phe
             20                  25                  30 gca atg gga cat gcg gtg cag gct ttc cat tta acc aac gac acg ctg   144
Ala Met Gly His Ala Val Gln Ala Phe His Leu Thr Asn Asp Thr Leu
         35                  40                  45 ggc gct ttt atg cgt gat aac gac ttt gac act ccg gtg atg gtg atg   192
Gly Ala Phe Met Arg Asp Asn Asp Phe Asp Thr Pro Val Met Val Met
     50                  55                  60 tgt tat cac ggc aat agc agc aaa ggc gcg gcg cag tat ctg ctg caa   240
Cys Tyr His Gly Asn Ser Ser Lys Gly Ala Ala Gln Tyr Leu Leu Gln
 65                  70                  75                  80 cag ggc tac gat gtg gtc tat agc att gac ggc ggc ttt gaa gcc tgg   288
Gln Gly Tyr Asp Val Val Tyr Ser Ile Asp Gly Gly Phe Glu Ala Trp
                 85                  90                  95 caa cgt cag ttt ccc gca gag gtg gcg tac ggc gcg taa               327
Gln Arg Gln Phe Pro Ala Glu Val Ala Tyr Gly Ala
            100                 105

<210> SEQ ID NO 10
<211> LENGTH: 108
<212> TYPE: PRT
<213> ORGANISM: Escherichia coli

<400> SEQUENCE: 10

Met Asp Gln Phe Glu Cys Ile Asn Val Ala Asp Ala His Gln Lys Leu
  1               5                  10                  15

Gln Glu Lys Glu Ala Val Leu Val Asp Ile Arg Asp Pro Gln Ser Phe
             20                  25                  30

Ala Met Gly His Ala Val Gln Ala Phe His Leu Thr Asn Asp Thr Leu
         35                  40                  45

Gly Ala Phe Met Arg Asp Asn Asp Phe Asp Thr Pro Val Met Val Met
     50                  55                  60

Cys Tyr His Gly Asn Ser Ser Lys Gly Ala Ala Gln Tyr Leu Leu Gln
 65                  70                  75                  80

Gln Gly Tyr Asp Val Val Tyr Ser Ile Asp Gly Gly Phe Glu Ala Trp
                 85                  90                  95

Gln Arg Gln Phe Pro Ala Glu Val Ala Tyr Gly Ala
            100                 105

<210> SEQ ID NO 11
<211> LENGTH: 846
<212> TYPE: DNA
<213> ORGANISM: Escherichia coli
<220> FEATURE:
<221> NAME/KEY: CDS
<222> LOCATION: (1)..(846)
<223> OTHER INFORMATION: glpF coding region

<400> SEQUENCE: 11 atg agt caa aca tca acc ttg aaa ggc cag tgc att gct gaa ttc ctc    48
Met Ser Gln Thr Ser Thr Leu Lys Gly Gln Cys Ile Ala Glu Phe Leu
  1               5                  10                  15 ggt acc ggg ttg ttg att ttc ttc ggt gtg ggt tgc gtt gca gca cta    96
Gly Thr Gly Leu Leu Ile Phe Phe Gly Val Gly Cys Val Ala Ala Leu
             20                  25                  30 aaa gtc gct ggt gcg tct ttt ggt cag tgg gaa atc agt gtc att tgg   144
Lys Val Ala Gly Ala Ser Phe Gly Gln Trp Glu Ile Ser Val Ile Trp
         35                  40                  45 gga ctg ggg gtg gca atg gcc atc tac ctg acc gca ggg gtt tcc ggc   192
Gly Leu Gly Val Ala Met Ala Ile Tyr Leu Thr Ala Gly Val Ser Gly
```

```
            50                  55                  60
gcg cat ctt aat ccc gct gtt acc att gca ttg tgg ctg ttt gcc tgt    240
Ala His Leu Asn Pro Ala Val Thr Ile Ala Leu Trp Leu Phe Ala Cys
 65                  70                  75                  80 ttc gac aag cgc aaa gtt att cct ttt atc gtt tca caa gtt gcc ggc    288
Phe Asp Lys Arg Lys Val Ile Pro Phe Ile Val Ser Gln Val Ala Gly
                 85                  90                  95 gct ttc tgt gct gcg gct tta gtt tac ggg ctt tac tac aat tta ttt    336
Ala Phe Cys Ala Ala Ala Leu Val Tyr Gly Leu Tyr Tyr Asn Leu Phe
            100                 105                 110 ttc gac ttc gag cag act cat cac att gtt cgc ggc agc gtt gaa agt    384
Phe Asp Phe Glu Gln Thr His His Ile Val Arg Gly Ser Val Glu Ser
        115                 120                 125 gtt gat ctg gct ggc act ttc tct act tac cct aat cct cat atc aat    432
Val Asp Leu Ala Gly Thr Phe Ser Thr Tyr Pro Asn Pro His Ile Asn
130                 135                 140 ttt gtg cag gct ttc gca gtt gag atg gtg att acc gct att ctg atg    480
Phe Val Gln Ala Phe Ala Val Glu Met Val Ile Thr Ala Ile Leu Met
145                 150                 155                 160 ggg ctg atc ctg gcg tta acg gac gat ggc aac ggt gta cca cgc ggc    528
Gly Leu Ile Leu Ala Leu Thr Asp Asp Gly Asn Gly Val Pro Arg Gly
                165                 170                 175 cct ttg gct ccc ttg ctg att ggt cta ctg att gcg tca att ggc gca    576
Pro Leu Ala Pro Leu Leu Ile Gly Leu Leu Ile Ala Val Ile Gly Ala
            180                 185                 190 tct atg ggc cca ttg aca ggt ttt gcc atg aac cca gcg cgt gac ttc    624
Ser Met Gly Pro Leu Thr Gly Phe Ala Met Asn Pro Ala Arg Asp Phe
        195                 200                 205 ggt ccg aaa gtc ttt gcc tgg ctg gcg ggc tgg ggc aat gtc gcc ttt    672
Gly Pro Lys Val Phe Ala Trp Leu Ala Gly Trp Gly Asn Val Ala Phe
210                 215                 220 acc ggc ggc aga gac att cct tac ttc ctg gtg ccg ctt ttc ggc cct    720
Thr Gly Gly Arg Asp Ile Pro Tyr Phe Leu Val Pro Leu Phe Gly Pro
225                 230                 235                 240 atc gtt ggc gcg att gta ggt gca ttt gcc tac cgc aaa ctg att ggt    768
Ile Val Gly Ala Ile Val Gly Ala Phe Ala Tyr Arg Lys Leu Ile Gly
                245                 250                 255 cgc cat ttg cct tgc gat atc tgt gtt gtg gaa gaa aag gaa acc aca    816
Arg His Leu Pro Cys Asp Ile Cys Val Val Glu Glu Lys Glu Thr Thr
            260                 265                 270 act cct tca gaa caa aaa gct tcg ctg taa                            846
Thr Pro Ser Glu Gln Lys Ala Ser Leu
        275                 280

<210> SEQ ID NO 12
<211> LENGTH: 281
<212> TYPE: PRT
<213> ORGANISM: Escherichia coli

<400> SEQUENCE: 12

Met Ser Gln Thr Ser Thr Leu Lys Gly Gln Cys Ile Ala Glu Phe Leu
  1               5                  10                  15

Gly Thr Gly Leu Leu Ile Phe Phe Gly Val Gly Cys Val Ala Ala Leu
                 20                  25                  30

Lys Val Ala Gly Ala Ser Phe Gly Gln Trp Glu Ile Ser Val Ile Trp
             35                  40                  45

Gly Leu Gly Val Ala Met Ala Ile Tyr Leu Thr Ala Gly Val Ser Gly
         50                  55                  60

Ala His Leu Asn Pro Ala Val Thr Ile Ala Leu Trp Leu Phe Ala Cys
```

```
                65                  70                  75                  80
Phe Asp Lys Arg Lys Val Ile Pro Phe Ile Val Ser Gln Val Ala Gly
                85                  90                  95

Ala Phe Cys Ala Ala Ala Leu Val Tyr Gly Leu Tyr Tyr Asn Leu Phe
            100                 105                 110

Phe Asp Phe Glu Gln Thr His His Ile Val Arg Gly Ser Val Glu Ser
            115                 120                 125

Val Asp Leu Ala Gly Thr Phe Ser Thr Tyr Pro Asn Pro His Ile Asn
        130                 135                 140

Phe Val Gln Ala Phe Ala Val Glu Met Val Ile Thr Ala Ile Leu Met
145                 150                 155                 160

Gly Leu Ile Leu Ala Leu Thr Asp Asp Gly Asn Gly Val Pro Arg Gly
                165                 170                 175

Pro Leu Ala Pro Leu Leu Ile Gly Leu Leu Ile Ala Val Ile Gly Ala
            180                 185                 190

Ser Met Gly Pro Leu Thr Gly Phe Ala Met Asn Pro Ala Arg Asp Phe
        195                 200                 205

Gly Pro Lys Val Phe Ala Trp Leu Ala Gly Trp Gly Asn Val Ala Phe
    210                 215                 220

Thr Gly Gly Arg Asp Ile Pro Tyr Phe Leu Val Pro Leu Phe Gly Pro
225                 230                 235                 240

Ile Val Gly Ala Ile Val Gly Ala Phe Ala Tyr Arg Lys Leu Ile Gly
                245                 250                 255

Arg His Leu Pro Cys Asp Ile Cys Val Val Glu Glu Lys Glu Thr Thr
            260                 265                 270

Thr Pro Ser Glu Gln Lys Ala Ser Leu
        275                 280

<210> SEQ ID NO 13
<211> LENGTH: 831
<212> TYPE: DNA
<213> ORGANISM: Escherichia coli
<220> FEATURE:
<221> NAME/KEY: CDS
<222> LOCATION: (1)..(831)
<223> OTHER INFORMATION: glpG coding region

<400> SEQUENCE: 13 atg ttg atg att acc tct ttt gct aac ccc cgc gtg gcg cag gcg ttt        48
Met Leu Met Ile Thr Ser Phe Ala Asn Pro Arg Val Ala Gln Ala Phe
1               5                   10                  15 gtt gat tac atg gcg acg cag ggt gtt atc ctc acg att caa caa cat        96
Val Asp Tyr Met Ala Thr Gln Gly Val Ile Leu Thr Ile Gln Gln His
            20                  25                  30 aac caa agc gat gtc tgg ctg gcg gat gag tcc cag gcc gag cgc gta       144
Asn Gln Ser Asp Val Trp Leu Ala Asp Glu Ser Gln Ala Glu Arg Val
        35                  40                  45 cgg gcg gag ctg gcg cgt ttt ctc gaa aac ccg gca gat ccg cgt tat       192
Arg Ala Glu Leu Ala Arg Phe Leu Glu Asn Pro Ala Asp Pro Arg Tyr
    50                  55                  60 ctg gcg gcg agc tgg cag gca ggc cat acc ggc agt ggc ctg cat tat       240
Leu Ala Ala Ser Trp Gln Ala Gly His Thr Gly Ser Gly Leu His Tyr
65                  70                  75                  80 cgc cgt tat cct ttc ttt gcc gcc ttg cgt gaa cgc gca ggt ccg gta       288
Arg Arg Tyr Pro Phe Phe Ala Ala Leu Arg Glu Arg Ala Gly Pro Val
                85                  90                  95 acc tgg gtg atg atg atc gcc tgc gtg gtg gtg ttt att gcc atg caa       336
Thr Trp Val Met Met Ile Ala Cys Val Val Val Phe Ile Ala Met Gln
            100                 105                 110
```

-continued

```
          100                 105                 110
att ctc ggc gat cag gaa gtg atg tta tgg ctg gcc tgg cca ttc gat     384
Ile Leu Gly Asp Gln Glu Val Met Leu Trp Leu Ala Trp Pro Phe Asp
        115                 120                 125 cca aca ctg aaa ttt gag ttc tgg cgt tac ttc acc cac gcg tta atg     432
Pro Thr Leu Lys Phe Glu Phe Trp Arg Tyr Phe Thr His Ala Leu Met
130                 135                 140 cac ttc tcg ctg atg cat atc ctc ttt aac ctg ctc tgg tgg tgg tat     480
His Phe Ser Leu Met His Ile Leu Phe Asn Leu Leu Trp Trp Trp Tyr
145                 150                 155                 160 ctc ggc ggt gcg gtg gaa aaa cgc ctc ggt agc ggt aag cta att gtc     528
Leu Gly Gly Ala Val Glu Lys Arg Leu Gly Ser Gly Lys Leu Ile Val
                165                 170                 175 att acg ctt atc agc gcc ctg tta agc ggc tat gtg cag caa aaa ttc     576
Ile Thr Leu Ile Ser Ala Leu Leu Ser Gly Tyr Val Gln Gln Lys Phe
            180                 185                 190 agc ggg ccg tgg ttt ggc ggg ctt tct ggc gtg gtg tat gcg ctg atg     624
Ser Gly Pro Trp Phe Gly Gly Leu Ser Gly Val Val Tyr Ala Leu Met
        195                 200                 205 ggc tac gtc tgg cta cgt ggc gaa cgc gat ccg caa agt ggc att tac     672
Gly Tyr Val Trp Leu Arg Gly Glu Arg Asp Pro Gln Ser Gly Ile Tyr
210                 215                 220 ctg caa cgt ggg tta att atc ttt gcg ctg atc tgg att gtc gcc gga     720
Leu Gln Arg Gly Leu Ile Ile Phe Ala Leu Ile Trp Ile Val Ala Gly
225                 230                 235                 240 tgg ttt gat ttg ttt ggg atg tcg atg gcg aac gga gca cac atc gcc     768
Trp Phe Asp Leu Phe Gly Met Ser Met Ala Asn Gly Ala His Ile Ala
                245                 250                 255 ggg tta gcc gtg ggt tta gcg atg gct ttt gtt gat tcg ctc aat gcg     816
Gly Leu Ala Val Gly Leu Ala Met Ala Phe Val Asp Ser Leu Asn Ala
            260                 265                 270 cga aaa cga aaa taa                                                  831
Arg Lys Arg Lys
        275
```

<210> SEQ ID NO 14
<211> LENGTH: 276
<212> TYPE: PRT
<213> ORGANISM: Escherichia coli

<400> SEQUENCE: 14

```
Met Leu Met Ile Thr Ser Phe Ala Asn Pro Arg Val Ala Gln Ala Phe
1               5                   10                  15

Val Asp Tyr Met Ala Thr Gln Gly Val Ile Leu Thr Ile Gln Gln His
            20                  25                  30

Asn Gln Ser Asp Val Trp Leu Ala Asp Glu Ser Gln Ala Glu Arg Val
        35                  40                  45

Arg Ala Glu Leu Ala Arg Phe Leu Glu Asn Pro Ala Asp Pro Arg Tyr
    50                  55                  60

Leu Ala Ala Ser Trp Gln Ala Gly His Thr Gly Ser Gly Leu His Tyr
65                  70                  75                  80

Arg Arg Tyr Pro Phe Phe Ala Ala Leu Arg Glu Arg Ala Gly Pro Val
                85                  90                  95

Thr Trp Val Met Met Ile Ala Cys Val Val Phe Ile Ala Met Gln
            100                 105                 110

Ile Leu Gly Asp Gln Glu Val Met Leu Trp Leu Ala Trp Pro Phe Asp
        115                 120                 125

Pro Thr Leu Lys Phe Glu Phe Trp Arg Tyr Phe Thr His Ala Leu Met
```

```
                130                 135                 140
His Phe Ser Leu Met His Ile Leu Phe Asn Leu Leu Trp Trp Trp Tyr
145                 150                 155                 160

Leu Gly Gly Ala Val Glu Lys Arg Leu Gly Ser Gly Lys Leu Ile Val
                165                 170                 175

Ile Thr Leu Ile Ser Ala Leu Leu Ser Gly Tyr Val Gln Gln Lys Phe
                180                 185                 190

Ser Gly Pro Trp Phe Gly Gly Leu Ser Gly Val Val Tyr Ala Leu Met
                195                 200                 205

Gly Tyr Val Trp Leu Arg Gly Glu Arg Asp Pro Gln Ser Gly Ile Tyr
                210                 215                 220

Leu Gln Arg Gly Leu Ile Ile Phe Ala Leu Ile Trp Ile Val Ala Gly
225                 230                 235                 240

Trp Phe Asp Leu Phe Gly Met Ser Met Ala Asn Gly Ala His Ile Ala
                245                 250                 255

Gly Leu Ala Val Gly Leu Ala Met Ala Phe Val Asp Ser Leu Asn Ala
                260                 265                 270

Arg Lys Arg Lys
        275

<210> SEQ ID NO 15
<211> LENGTH: 1509
<212> TYPE: DNA
<213> ORGANISM: Escherichia coli
<220> FEATURE:
<221> NAME/KEY: CDS
<222> LOCATION: (1)..(1509)
<223> OTHER INFORMATION: glpK coding region

<400> SEQUENCE: 15 atg act gaa aaa aaa tat atc gtt gcg ctc gac cag ggc acc acc agc      48
Met Thr Glu Lys Lys Tyr Ile Val Ala Leu Asp Gln Gly Thr Thr Ser
1               5                   10                  15 tcc cgc gcg gtc gta atg gat cac gat gcc aat atc att agc gtg tcg      96
Ser Arg Ala Val Val Met Asp His Asp Ala Asn Ile Ile Ser Val Ser
            20                  25                  30 cag cgc gaa ttt gag caa atc tac cca aaa cca ggt tgg gta gaa cac     144
Gln Arg Glu Phe Glu Gln Ile Tyr Pro Lys Pro Gly Trp Val Glu His
        35                  40                  45 gac cca atg gaa atc tgg gcc acc caa agc tcc acg ctg gta gaa gtg     192
Asp Pro Met Glu Ile Trp Ala Thr Gln Ser Ser Thr Leu Val Glu Val
    50                  55                  60 ctg gcg aaa gcc gat atc agt tcc gat caa att gca gct atc ggt att     240
Leu Ala Lys Ala Asp Ile Ser Ser Asp Gln Ile Ala Ala Ile Gly Ile
65                  70                  75                  80 acg aac cag cgt gaa acc act att gtc tgg gaa aaa gaa acc ggc aag     288
Thr Asn Gln Arg Glu Thr Thr Ile Val Trp Glu Lys Glu Thr Gly Lys
                85                  90                  95 cct atc tat aac gcc att gtc tgg cag tgc cgt cgt acc gca gaa atc     336
Pro Ile Tyr Asn Ala Ile Val Trp Gln Cys Arg Arg Thr Ala Glu Ile
            100                 105                 110 tgc gag cat tta aaa cgt gac ggt tta gaa gat tat atc cgc agc aat     384
Cys Glu His Leu Lys Arg Asp Gly Leu Glu Asp Tyr Ile Arg Ser Asn
        115                 120                 125 acc ggt ctg gtg att gac ccg tac ttt tct ggc acc aaa gtg aag tgg     432
Thr Gly Leu Val Ile Asp Pro Tyr Phe Ser Gly Thr Lys Val Lys Trp
    130                 135                 140 atc ctc gac cat gtg gaa ggc tct cgc gag cgt gca cgt cgt ggt gaa     480
Ile Leu Asp His Val Glu Gly Ser Arg Glu Arg Ala Arg Arg Gly Glu
```

```
                                                                            -continued
145                    150                    155                    160
ttg ctg ttt ggt acg gtt gat acg tgg ctt atc tgg aaa atg act cag       528
Leu Leu Phe Gly Thr Val Asp Thr Trp Leu Ile Trp Lys Met Thr Gln
                165                    170                    175 ggc cgt gtc cat gtg acc gat tac acc aac gcc tct cgt acc atg ttg       576
Gly Arg Val His Val Thr Asp Tyr Thr Asn Ala Ser Arg Thr Met Leu
                180                    185                    190 ttc aac atc cat acc ctg gac tgg gac gac aaa atg ctg gaa gtg ctg       624
Phe Asn Ile His Thr Leu Asp Trp Asp Asp Lys Met Leu Glu Val Leu
                195                    200                    205 gat att ccg cgc gag atg ctg cca gaa gtg cgt cgt tct tcc gaa gta       672
Asp Ile Pro Arg Glu Met Leu Pro Glu Val Arg Arg Ser Ser Glu Val
    210                    215                    220 tac ggt cag act aac att ggc ggc aaa ggc ggc acg cgt att cca atc       720
Tyr Gly Gln Thr Asn Ile Gly Gly Lys Gly Gly Thr Arg Ile Pro Ile
225                    230                    235                    240 tcc ggg atc gcc ggt gac cag cag gcc gcg ctg ttt ggt cag ttg tgc       768
Ser Gly Ile Ala Gly Asp Gln Gln Ala Ala Leu Phe Gly Gln Leu Cys
                245                    250                    255 gtg aaa gaa ggg atg gcg aag aac acc tat ggc act ggc tgc ttt atg       816
Val Lys Glu Gly Met Ala Lys Asn Thr Tyr Gly Thr Gly Cys Phe Met
                260                    265                    270 ctg atg aac act ggc gag aaa gcg gtg aaa tca gaa aac ggc ctg ctg       864
Leu Met Asn Thr Gly Glu Lys Ala Val Lys Ser Glu Asn Gly Leu Leu
                275                    280                    285 acc acc atc gcc tgc ggc ccg act ggc gaa gtg aac tat gcg ttg gaa       912
Thr Thr Ile Ala Cys Gly Pro Thr Gly Glu Val Asn Tyr Ala Leu Glu
                290                    295                    300 ggt gcg gtg ttt atg gca ggc gca tcc att cag tgg ctg cgc gat gaa       960
Gly Ala Val Phe Met Ala Gly Ala Ser Ile Gln Trp Leu Arg Asp Glu
305                    310                    315                    320 atg aag ttg att aac gac gcc tac gat tcc gaa tat ttc gcc acc aaa      1008
Met Lys Leu Ile Asn Asp Ala Tyr Asp Ser Glu Tyr Phe Ala Thr Lys
                325                    330                    335 gtg caa aac acc aat ggt gtg tat gtg gtt ccg gca ttt acc ggg ctg      1056
Val Gln Asn Thr Asn Gly Val Tyr Val Val Pro Ala Phe Thr Gly Leu
                340                    345                    350 ggt gcg ccg tac tgg gac ccg tat gcg cgc ggg gcg att ttc ggt ctg      1104
Gly Ala Pro Tyr Trp Asp Pro Tyr Ala Arg Gly Ala Ile Phe Gly Leu
                355                    360                    365 act cgt ggg gtg aac gct aac cac att ata cgc gcg acg ctg gag tct      1152
Thr Arg Gly Val Asn Ala Asn His Ile Ile Arg Ala Thr Leu Glu Ser
    370                    375                    380 att gct tat cag acg cgt gac gtg ctg gaa gcg atg cag gcc gac tct      1200
Ile Ala Tyr Gln Thr Arg Asp Val Leu Glu Ala Met Gln Ala Asp Ser
385                    390                    395                    400 ggt atc cgt ctg cac gcc ctg cgc gtg gat ggt ggc gca gta gca aac      1248
Gly Ile Arg Leu His Ala Leu Arg Val Asp Gly Gly Ala Val Ala Asn
                405                    410                    415 aat ttc ctg atg cag ttc cag tcc gat att ctc ggc acc cgc gtt gag      1296
Asn Phe Leu Met Gln Phe Gln Ser Asp Ile Leu Gly Thr Arg Val Glu
                420                    425                    430 cgc ccg gaa gtg cgc gaa gtc acc gca ttg ggt gcg gcc tat ctc gca      1344
Arg Pro Glu Val Arg Glu Val Thr Ala Leu Gly Ala Ala Tyr Leu Ala
                435                    440                    445 ggc ctg gcg gtt ggc ttc tgg cag aac ctc gac gag ctg caa gag aaa      1392
Gly Leu Ala Val Gly Phe Trp Gln Asn Leu Asp Glu Leu Gln Glu Lys
    450                    455                    460 gcg gtg att gag cgc gag ttc cgt cca ggc atc gaa acc act gag cgt      1440
```

```
Ala Val Ile Glu Arg Glu Phe Arg Pro Gly Ile Glu Thr Thr Glu Arg
465                 470                 475                 480 aat tac cgt tac gca ggc tgg aaa aaa gcg gtt aaa cgc gcg atg gcg    1488
Asn Tyr Arg Tyr Ala Gly Trp Lys Lys Ala Val Lys Arg Ala Met Ala
                    485                 490                 495 tgg gaa gaa cac gac gaa taa                                        1509
Trp Glu Glu His Asp Glu
            500

<210> SEQ ID NO 16
<211> LENGTH: 502
<212> TYPE: PRT
<213> ORGANISM: Escherichia coli

<400> SEQUENCE: 16

Met Thr Glu Lys Lys Tyr Ile Val Ala Leu Asp Gln Gly Thr Thr Ser
1               5                   10                  15

Ser Arg Ala Val Val Met Asp His Asp Ala Asn Ile Ile Ser Val Ser
            20                  25                  30

Gln Arg Glu Phe Glu Gln Ile Tyr Pro Lys Pro Gly Trp Val Glu His
        35                  40                  45

Asp Pro Met Glu Ile Trp Ala Thr Gln Ser Ser Thr Leu Val Glu Val
    50                  55                  60

Leu Ala Lys Ala Asp Ile Ser Ser Asp Gln Ile Ala Ala Ile Gly Ile
65                  70                  75                  80

Thr Asn Gln Arg Glu Thr Thr Ile Val Trp Glu Lys Glu Thr Gly Lys
                85                  90                  95

Pro Ile Tyr Asn Ala Ile Val Trp Gln Cys Arg Arg Thr Ala Glu Ile
            100                 105                 110

Cys Glu His Leu Lys Arg Asp Gly Leu Glu Asp Tyr Ile Arg Ser Asn
        115                 120                 125

Thr Gly Leu Val Ile Asp Pro Tyr Phe Ser Gly Thr Lys Val Lys Trp
    130                 135                 140

Ile Leu Asp His Val Glu Gly Ser Arg Glu Arg Ala Arg Arg Gly Glu
145                 150                 155                 160

Leu Leu Phe Gly Thr Val Asp Thr Trp Leu Ile Trp Lys Met Thr Gln
                165                 170                 175

Gly Arg Val His Val Thr Asp Tyr Thr Asn Ala Ser Arg Thr Met Leu
            180                 185                 190

Phe Asn Ile His Thr Leu Asp Trp Asp Asp Lys Met Leu Glu Val Leu
        195                 200                 205

Asp Ile Pro Arg Glu Met Leu Pro Glu Val Arg Arg Ser Ser Glu Val
    210                 215                 220

Tyr Gly Gln Thr Asn Ile Gly Gly Lys Gly Gly Thr Arg Ile Pro Ile
225                 230                 235                 240

Ser Gly Ile Ala Gly Asp Gln Gln Ala Ala Leu Phe Gly Gln Leu Cys
                245                 250                 255

Val Lys Glu Gly Met Ala Lys Asn Thr Tyr Gly Thr Gly Cys Phe Met
            260                 265                 270

Leu Met Asn Thr Gly Glu Lys Ala Val Lys Ser Glu Asn Gly Leu Leu
        275                 280                 285

Thr Thr Ile Ala Cys Gly Pro Thr Gly Glu Val Asn Tyr Ala Leu Glu
    290                 295                 300

Gly Ala Val Phe Met Ala Gly Ala Ser Ile Gln Trp Leu Arg Asp Glu
305                 310                 315                 320
```

```
Met Lys Leu Ile Asn Asp Ala Tyr Asp Ser Glu Tyr Phe Ala Thr Lys
                325                 330                 335
Val Gln Asn Thr Asn Gly Val Tyr Val Val Pro Ala Phe Thr Gly Leu
            340                 345                 350
Gly Ala Pro Tyr Trp Asp Pro Tyr Ala Arg Gly Ala Ile Phe Gly Leu
        355                 360                 365
Thr Arg Gly Val Asn Ala Asn His Ile Ile Arg Ala Thr Leu Glu Ser
    370                 375                 380
Ile Ala Tyr Gln Thr Arg Asp Val Leu Glu Ala Met Gln Ala Asp Ser
385                 390                 395                 400
Gly Ile Arg Leu His Ala Leu Arg Val Asp Gly Gly Ala Val Ala Asn
                405                 410                 415
Asn Phe Leu Met Gln Phe Gln Ser Asp Ile Leu Gly Thr Arg Val Glu
            420                 425                 430
Arg Pro Glu Val Arg Glu Val Thr Ala Leu Gly Ala Ala Tyr Leu Ala
        435                 440                 445
Gly Leu Ala Val Gly Phe Trp Gln Asn Leu Asp Glu Leu Gln Glu Lys
    450                 455                 460
Ala Val Ile Glu Arg Glu Phe Arg Pro Gly Ile Glu Thr Thr Glu Arg
465                 470                 475                 480
Asn Tyr Arg Tyr Ala Gly Trp Lys Lys Ala Val Lys Arg Ala Met Ala
                485                 490                 495
Trp Glu Glu His Asp Glu
            500

<210> SEQ ID NO 17
<211> LENGTH: 1077
<212> TYPE: DNA
<213> ORGANISM: Escherichia coli
<220> FEATURE:
<221> NAME/KEY: CDS
<222> LOCATION: (1)..(1077)
<223> OTHER INFORMATION: glpQ coding region

<400> SEQUENCE: 17 atg aaa ttg acg ctg aaa aac ctt agc atg gcg atc atg atg agc act     48
Met Lys Leu Thr Leu Lys Asn Leu Ser Met Ala Ile Met Met Ser Thr
1               5                   10                  15 ata gtc atg gga agc agt gca atg gcg gcg gac agc aac gaa aaa ata     96
Ile Val Met Gly Ser Ser Ala Met Ala Ala Asp Ser Asn Glu Lys Ile
            20                  25                  30 gtc atc gcc cat cgc ggt gcc agt gga tat ttg ccg gag cat acg ctg    144
Val Ile Ala His Arg Gly Ala Ser Gly Tyr Leu Pro Glu His Thr Leu
        35                  40                  45 cca gca aaa gcg atg gcg tat gcg cag gga gcg gat tat ctg gaa cag    192
Pro Ala Lys Ala Met Ala Tyr Ala Gln Gly Ala Asp Tyr Leu Glu Gln
    50                  55                  60 gat ttg gtg atg acc aaa gac gac aat ctg gtt gtt ctg cat gac cat    240
Asp Leu Val Met Thr Lys Asp Asp Asn Leu Val Val Leu His Asp His
65                  70                  75                  80 tac ctc gat cgt gtt act gat gtt gcc gat cgt ttc ccg gat cgg gcg    288
Tyr Leu Asp Arg Val Thr Asp Val Ala Asp Arg Phe Pro Asp Arg Ala
                85                  90                  95 cgc aaa gac ggt cgt tac tac gcg ata gat ttc acg ctg gat gaa att    336
Arg Lys Asp Gly Arg Tyr Tyr Ala Ile Asp Phe Thr Leu Asp Glu Ile
            100                 105                 110 aag tcg ttg aaa ttt acc gaa ggt ttc gat att gaa aac ggt aaa aaa    384
Lys Ser Leu Lys Phe Thr Glu Gly Phe Asp Ile Glu Asn Gly Lys Lys
        115                 120                 125
```

```
gtg cag act tat ccg ggg cgt ttc cca atg ggt aag tcc gac ttc cgg      432
Val Gln Thr Tyr Pro Gly Arg Phe Pro Met Gly Lys Ser Asp Phe Arg
    130                 135                 140 gtg cac acc ttt gaa gaa gag att gaa ttt gtt cag ggg tta aat cac      480
Val His Thr Phe Glu Glu Glu Ile Glu Phe Val Gln Gly Leu Asn His
145                 150                 155                 160 tct acc ggg aaa aat atc ggt att tat cca gaa atc aaa gcg ccg tgg      528
Ser Thr Gly Lys Asn Ile Gly Ile Tyr Pro Glu Ile Lys Ala Pro Trp
                165                 170                 175 ttc cat cat cag gaa ggg aag gat att gcg gca aaa acg ctg gaa gtg      576
Phe His His Gln Glu Gly Lys Asp Ile Ala Ala Lys Thr Leu Glu Val
            180                 185                 190 ctg aag aaa tat ggt tac acc ggt aaa gac gat aaa gtt tat ttg caa      624
Leu Lys Lys Tyr Gly Tyr Thr Gly Lys Asp Asp Lys Val Tyr Leu Gln
        195                 200                 205 tgt ttt gat gct gat gag ctg aag cgt att aag aat gag ctg gaa ccc      672
Cys Phe Asp Ala Asp Glu Leu Lys Arg Ile Lys Asn Glu Leu Glu Pro
    210                 215                 220 aaa atg ggc atg gag ctc aat ctg gta cag ctg att gcc tat acc gac      720
Lys Met Gly Met Glu Leu Asn Leu Val Gln Leu Ile Ala Tyr Thr Asp
225                 230                 235                 240 tgg aat gaa acg cag cag aaa cag ccg gat gga agc tgg gtt aat tac      768
Trp Asn Glu Thr Gln Gln Lys Gln Pro Asp Gly Ser Trp Val Asn Tyr
                245                 250                 255 aac tac gac tgg atg ttt aag ccg ggt gcc atg aaa cag gtg gcg gaa      816
Asn Tyr Asp Trp Met Phe Lys Pro Gly Ala Met Lys Gln Val Ala Glu
            260                 265                 270 tat gca gat ggt att ggt ccg gat tac cat atg ttg att gag gag aca      864
Tyr Ala Asp Gly Ile Gly Pro Asp Tyr His Met Leu Ile Glu Glu Thr
        275                 280                 285 tcg cag ccg ggt aat atc aaa ctc act ggc atg gtg caa gat gct cag      912
Ser Gln Pro Gly Asn Ile Lys Leu Thr Gly Met Val Gln Asp Ala Gln
    290                 295                 300 cag aat aaa ctg gta gtg cat cct tat acc gtg cgg tca gat aaa ctg      960
Gln Asn Lys Leu Val Val His Pro Tyr Thr Val Arg Ser Asp Lys Leu
305                 310                 315                 320 cct gaa tac act cct gat gtg aat cag tta tat gat gct ctg tat aac     1008
Pro Glu Tyr Thr Pro Asp Val Asn Gln Leu Tyr Asp Ala Leu Tyr Asn
                325                 330                 335 aaa gcg ggt gta aat ggg ctg ttt act gat ttc cct gat aag gca gta     1056
Lys Ala Gly Val Asn Gly Leu Phe Thr Asp Phe Pro Asp Lys Ala Val
            340                 345                 350 aaa ttt ctt aat aaa gag taa                                         1077
Lys Phe Leu Asn Lys Glu
        355
```

<210> SEQ ID NO 18
<211> LENGTH: 358
<212> TYPE: PRT
<213> ORGANISM: Escherichia coli

<400> SEQUENCE: 18

```
Met Lys Leu Thr Leu Lys Asn Leu Ser Met Ala Ile Met Met Ser Thr
1               5                   10                  15

Ile Val Met Gly Ser Ser Ala Met Ala Ala Asp Ser Asn Glu Lys Ile
                20                  25                  30

Val Ile Ala His Arg Gly Ala Ser Gly Tyr Leu Pro Glu His Thr Leu
            35                  40                  45

Pro Ala Lys Ala Met Ala Tyr Ala Gln Gly Ala Asp Tyr Leu Glu Gln
```

```
                50              55              60
Asp Leu Val Met Thr Lys Asp Asn Leu Val Val Leu His Asp His
 65                  70                  75                  80

Tyr Leu Asp Arg Val Thr Asp Val Ala Asp Arg Phe Pro Asp Arg Ala
                 85                  90                  95

Arg Lys Asp Gly Arg Tyr Tyr Ala Ile Asp Phe Thr Leu Asp Glu Ile
            100                 105                 110

Lys Ser Leu Lys Phe Thr Glu Gly Phe Asp Ile Glu Asn Gly Lys Lys
        115                 120                 125

Val Gln Thr Tyr Pro Gly Arg Phe Pro Met Gly Lys Ser Asp Phe Arg
    130                 135                 140

Val His Thr Phe Glu Glu Ile Glu Phe Val Gln Gly Leu Asn His
145                 150                 155                 160

Ser Thr Gly Lys Asn Ile Gly Ile Tyr Pro Glu Ile Lys Ala Pro Trp
                165                 170                 175

Phe His His Gln Glu Gly Lys Asp Ile Ala Ala Lys Thr Leu Glu Val
            180                 185                 190

Leu Lys Lys Tyr Gly Tyr Thr Gly Lys Asp Asp Lys Val Tyr Leu Gln
        195                 200                 205

Cys Phe Asp Ala Asp Glu Leu Lys Arg Ile Lys Asn Glu Leu Glu Pro
    210                 215                 220

Lys Met Gly Met Glu Leu Asn Leu Val Gln Leu Ile Ala Tyr Thr Asp
225                 230                 235                 240

Trp Asn Glu Thr Gln Gln Lys Gln Pro Asp Gly Ser Trp Val Asn Tyr
                245                 250                 255

Asn Tyr Asp Trp Met Phe Lys Pro Gly Ala Met Lys Gln Val Ala Glu
            260                 265                 270

Tyr Ala Asp Gly Ile Gly Pro Asp Tyr His Met Leu Ile Glu Glu Thr
        275                 280                 285

Ser Gln Pro Gly Asn Ile Lys Leu Thr Gly Met Val Gln Asp Ala Gln
    290                 295                 300

Gln Asn Lys Leu Val Val His Pro Tyr Thr Val Arg Ser Asp Lys Leu
305                 310                 315                 320

Pro Glu Tyr Thr Pro Asp Val Asn Gln Leu Tyr Asp Ala Leu Tyr Asn
                325                 330                 335

Lys Ala Gly Val Asn Gly Leu Phe Thr Asp Phe Pro Asp Lys Ala Val
            340                 345                 350

Lys Phe Leu Asn Lys Glu
        355
```

<210> SEQ ID NO 19
<211> LENGTH: 1359
<212> TYPE: DNA
<213> ORGANISM: Escherichia coli
<220> FEATURE:
<221> NAME/KEY: CDS
<222> LOCATION: (1)..(1359)
<223> OTHER INFORMATION: glpT coding region

<400> SEQUENCE: 19

```
atg ttg agt att ttt aaa cca gcg cca cac aaa gcg cgc tta cct gcc      48
Met Leu Ser Ile Phe Lys Pro Ala Pro His Lys Ala Arg Leu Pro Ala
 1               5                  10                  15 gcg gag atc gat ccg act tat cgt cga ttg cgc tgg caa att ttc ctg      96
Ala Glu Ile Asp Pro Thr Tyr Arg Arg Leu Arg Trp Gln Ile Phe Leu
                20                  25                  30
```

-continued

| | | |
|---|---|---|
| ggg ata ttc ttt ggc tat gcg gct tac tat ttg gtt cgt aag aac ttt<br>Gly Ile Phe Phe Gly Tyr Ala Ala Tyr Tyr Leu Val Arg Lys Asn Phe<br>        35                       40                        45 | 144 |
| gcg ctt gct atg cct tat ctg gtt gag cag gga ttc tca cgc ggt gat<br>Ala Leu Ala Met Pro Tyr Leu Val Glu Gln Gly Phe Ser Arg Gly Asp<br>50                         55                        60 | 192 |
| tta ggt ttt gcc ctt tcg ggg atc tcg att gct tat gga ttt tcg aaa<br>Leu Gly Phe Ala Leu Ser Gly Ile Ser Ile Ala Tyr Gly Phe Ser Lys<br>65                         70                     75                        80 | 240 |
| ttc atc atg ggt tcg gta tcg gat cgc tcg aat ccg cgc gtt ttc ctg<br>Phe Ile Met Gly Ser Val Ser Asp Arg Ser Asn Pro Arg Val Phe Leu<br>                      85                       90                       95 | 288 |
| ccc gca ggt ttg att ctg gcg gcg gca gtg atg ttg ttt atg ggc ttt<br>Pro Ala Gly Leu Ile Leu Ala Ala Ala Val Met Leu Phe Met Gly Phe<br>                     100                     105                     110 | 336 |
| gtg cca tgg gcg acg tcg agc att gcg gtg atg ttt gta ctg ttg ttc<br>Val Pro Trp Ala Thr Ser Ser Ile Ala Val Met Phe Val Leu Leu Phe<br>               115                     120                     125 | 384 |
| ctc tgc ggt tgg ttc cag ggg atg ggg tgg ccg ccg tgt ggt cgt act<br>Leu Cys Gly Trp Phe Gln Gly Met Gly Trp Pro Pro Cys Gly Arg Thr<br>130                            135                     140 | 432 |
| atg gtg cac tgg tgg tcg cag aaa gaa cgt ggc ggc att gtg tca gtg<br>Met Val His Trp Trp Ser Gln Lys Glu Arg Gly Gly Ile Val Ser Val<br>145                       150                     155                     160 | 480 |
| tgg aac tgt gcg cac aac gtc ggt ggt ggt att ccg ccg ctg ctg ttc<br>Trp Asn Cys Ala His Asn Val Gly Gly Gly Ile Pro Pro Leu Leu Phe<br>                     165                     170                     175 | 528 |
| ctg ctg ggg atg gcc tgg ttc aat gac tgg cat gcg gcg ctc tat atg<br>Leu Leu Gly Met Ala Trp Phe Asn Asp Trp His Ala Ala Leu Tyr Met<br>               180                     185                     190 | 576 |
| cct gct ttc tgc gcc att ctg gtg gca tta ttc gcc ttt gcg atg atg<br>Pro Ala Phe Cys Ala Ile Leu Val Ala Leu Phe Ala Phe Ala Met Met<br>195                            200                     205 | 624 |
| cgc gat acc ccg caa tcc tgt ggc ttg ccg ccg atc gaa gag tac aaa<br>Arg Asp Thr Pro Gln Ser Cys Gly Leu Pro Pro Ile Glu Glu Tyr Lys<br>210                            215                     220 | 672 |
| aat gat tat ccg gac gac tat aac gaa aaa gcg gaa cag gag ctg acg<br>Asn Asp Tyr Pro Asp Asp Tyr Asn Glu Lys Ala Glu Gln Glu Leu Thr<br>225                       230                     235                     240 | 720 |
| gcg aag caa atc ttc atg cag tac gta ctg ccg aac aaa ctg ctg tgg<br>Ala Lys Gln Ile Phe Met Gln Tyr Val Leu Pro Asn Lys Leu Leu Trp<br>                     245                     250                     255 | 768 |
| tat atc gcc atc gcc aac gtg ttc gtt tat ctg ctg cgt tac ggc atc<br>Tyr Ile Ala Ile Ala Asn Val Phe Val Tyr Leu Leu Arg Tyr Gly Ile<br>               260                     265                     270 | 816 |
| ctc gac tgg tca ccg act tat ctg aaa gag gtt aag cat ttc gcg cta<br>Leu Asp Trp Ser Pro Thr Tyr Leu Lys Glu Val Lys His Phe Ala Leu<br>             275                     280                     285 | 864 |
| gat aaa tcc tcc tgg gcc tac ttc ctt tat gaa tat gca ggt att ccg<br>Asp Lys Ser Ser Trp Ala Tyr Phe Leu Tyr Glu Tyr Ala Gly Ile Pro<br>290                       295                     300 | 912 |
| ggc act ctg ctg tgc ggc tgg atg tcg gat aaa gtc ttc cgt ggc aac<br>Gly Thr Leu Leu Cys Gly Trp Met Ser Asp Lys Val Phe Arg Gly Asn<br>305                       310                     315                     320 | 960 |
| cgt ggg gca acc ggc gtt ttc ttt atg aca ctg gtg acc atc gcg act<br>Arg Gly Ala Thr Gly Val Phe Phe Met Thr Leu Val Thr Ile Ala Thr<br>                     325                     330                     335 | 1008 |
| atc gtt tac tgg atg aac ccg gca ggt aac cca acc gtc gat atg att<br>Ile Val Tyr Trp Met Asn Pro Ala Gly Asn Pro Thr Val Asp Met Ile<br>               340                     345                     350 | 1056 |

-continued

```
tgt atg att gtt atc ggc ttc ctg atc tac ggt cct gtg atg ctg atc      1104
Cys Met Ile Val Ile Gly Phe Leu Ile Tyr Gly Pro Val Met Leu Ile
        355                 360                 365 ggt ctg cat gcg ctg gaa ctg gca ccg aaa aaa gcg gca ggt acg gca      1152
Gly Leu His Ala Leu Glu Leu Ala Pro Lys Lys Ala Ala Gly Thr Ala
370                 375                 380 gcg ggc ttt acc ggg ctg ttt ggt tac ctg ggc ggt tcg gtg gcg gcg      1200
Ala Gly Phe Thr Gly Leu Phe Gly Tyr Leu Gly Gly Ser Val Ala Ala
385                 390                 395                 400 agc gcg att gtt ggc tac acc gtg gac ttc ttc ggc tgg gat ggc ggc      1248
Ser Ala Ile Val Gly Tyr Thr Val Asp Phe Phe Gly Trp Asp Gly Gly
            405                 410                 415 ttt atg gta atg att ggc ggc agc att ctg gcg gtt atc ttg ttg att      1296
Phe Met Val Met Ile Gly Gly Ser Ile Leu Ala Val Ile Leu Leu Ile
        420                 425                 430 gtt gtg atg att ggc gaa aaa cgt cgc cat gaa caa tta ctg caa gaa      1344
Val Val Met Ile Gly Glu Lys Arg Arg His Glu Gln Leu Leu Gln Glu
            435                 440                 445 cgc aac gga ggc taa                                                   1359
Arg Asn Gly Gly
        450
```

<210> SEQ ID NO 20
<211> LENGTH: 452
<212> TYPE: PRT
<213> ORGANISM: Escherichia coli

<400> SEQUENCE: 20

```
Met Leu Ser Ile Phe Lys Pro Ala Pro His Lys Ala Arg Leu Pro Ala
1               5                   10                  15

Ala Glu Ile Asp Pro Thr Tyr Arg Arg Leu Arg Trp Gln Ile Phe Leu
            20                  25                  30

Gly Ile Phe Phe Gly Tyr Ala Ala Tyr Tyr Leu Val Arg Lys Asn Phe
        35                  40                  45

Ala Leu Ala Met Pro Tyr Leu Val Glu Gln Gly Phe Ser Arg Gly Asp
    50                  55                  60

Leu Gly Phe Ala Leu Ser Gly Ile Ser Ile Ala Tyr Gly Phe Ser Lys
65                  70                  75                  80

Phe Ile Met Gly Ser Val Ser Asp Arg Ser Asn Pro Arg Val Phe Leu
                85                  90                  95

Pro Ala Gly Leu Ile Leu Ala Ala Val Met Leu Phe Met Gly Phe
            100                 105                 110

Val Pro Trp Ala Thr Ser Ser Ile Ala Val Met Phe Val Leu Leu Phe
        115                 120                 125

Leu Cys Gly Trp Phe Gln Gly Met Gly Trp Pro Pro Cys Gly Arg Thr
    130                 135                 140

Met Val His Trp Trp Ser Gln Lys Glu Arg Gly Gly Ile Val Ser Val
145                 150                 155                 160

Trp Asn Cys Ala His Asn Val Gly Gly Gly Ile Pro Pro Leu Leu Phe
                165                 170                 175

Leu Leu Gly Met Ala Trp Phe Asn Asp Trp His Ala Ala Leu Tyr Met
            180                 185                 190

Pro Ala Phe Cys Ala Ile Leu Val Ala Leu Phe Ala Phe Ala Met Met
        195                 200                 205

Arg Asp Thr Pro Gln Ser Cys Gly Leu Pro Pro Ile Glu Glu Tyr Lys
    210                 215                 220
```

-continued

```
Asn Asp Tyr Pro Asp Asp Tyr Asn Glu Lys Ala Glu Gln Glu Leu Thr
225                 230                 235                 240

Ala Lys Gln Ile Phe Met Gln Tyr Val Leu Pro Asn Lys Leu Leu Trp
            245                 250                 255

Tyr Ile Ala Ile Ala Asn Val Phe Val Tyr Leu Leu Arg Tyr Gly Ile
                260                 265                 270

Leu Asp Trp Ser Pro Thr Tyr Leu Lys Glu Val Lys His Phe Ala Leu
        275                 280                 285

Asp Lys Ser Ser Trp Ala Tyr Phe Leu Tyr Glu Tyr Ala Gly Ile Pro
    290                 295                 300

Gly Thr Leu Leu Cys Gly Trp Met Ser Asp Lys Val Phe Arg Gly Asn
305                 310                 315                 320

Arg Gly Ala Thr Gly Val Phe Phe Met Thr Leu Val Thr Ile Ala Thr
                325                 330                 335

Ile Val Tyr Trp Met Asn Pro Ala Gly Asn Pro Thr Val Asp Met Ile
                340                 345                 350

Cys Met Ile Val Ile Gly Phe Leu Ile Tyr Gly Pro Val Met Leu Ile
        355                 360                 365

Gly Leu His Ala Leu Glu Leu Ala Pro Lys Lys Ala Ala Gly Thr Ala
370                 375                 380

Ala Gly Phe Thr Gly Leu Phe Gly Tyr Leu Gly Gly Ser Val Ala Ala
385                 390                 395                 400

Ser Ala Ile Val Gly Tyr Thr Val Asp Phe Phe Gly Trp Asp Gly Gly
                405                 410                 415

Phe Met Val Met Ile Gly Gly Ser Ile Leu Ala Val Ile Leu Leu Ile
        420                 425                 430

Val Val Met Ile Gly Glu Lys Arg Arg His Glu Gln Leu Leu Gln Glu
        435                 440                 445

Arg Asn Gly Gly
        450
```

```
<210> SEQ ID NO 21
<211> LENGTH: 1011
<212> TYPE: DNA
<213> ORGANISM: Escherichia coli
<220> FEATURE:
<221> NAME/KEY: CDS
<222> LOCATION: (1)..(1011)
<223> OTHER INFORMATION: glpX coding region

<400> SEQUENCE: 21
```

```
atg aga cga gaa ctt gcc atc gaa ttt tcc cgc gtc acc gaa tca gcg      48
Met Arg Arg Glu Leu Ala Ile Glu Phe Ser Arg Val Thr Glu Ser Ala
1               5                   10                  15 gcg ctg gct ggc tac aaa tgg tta gga cgc ggc gat aaa aac acc gcg      96
Ala Leu Ala Gly Tyr Lys Trp Leu Gly Arg Gly Asp Lys Asn Thr Ala
                20                  25                  30 gac ggc gcg gcg gta aac gcc atg cgt att atg ctc aac cag gtc aac     144
Asp Gly Ala Ala Val Asn Ala Met Arg Ile Met Leu Asn Gln Val Asn
            35                  40                  45 att gac ggc acc atc gtc att ggt gaa ggt gaa atc gac gaa gca ccg     192
Ile Asp Gly Thr Ile Val Ile Gly Glu Gly Glu Ile Asp Glu Ala Pro
        50                  55                  60 atg ctc tac att ggt gaa aaa gtc ggt act ggt cgc ggc gac gcg gta     240
Met Leu Tyr Ile Gly Glu Lys Val Gly Thr Gly Arg Gly Asp Ala Val
65                  70                  75                  80 gat att gct gtt gat ccg att gaa ggc acg cgc atg acg gcg atg ggc     288
Asp Ile Ala Val Asp Pro Ile Glu Gly Thr Arg Met Thr Ala Met Gly
```

```
                        85                  90                  95
cag gct aac gcg ctg gcg gtg ctg gca gta ggc gat aaa ggc tgc ttc        336
Gln Ala Asn Ala Leu Ala Val Leu Ala Val Gly Asp Lys Gly Cys Phe
                100                 105                 110 ctc aat gcg ccg gat atg tat atg gag aag ctg att gtc ggg ccg gga        384
Leu Asn Ala Pro Asp Met Tyr Met Glu Lys Leu Ile Val Gly Pro Gly
            115                 120                 125 gcc aaa ggc acc att gat ctg aac ctg ccg ctg gcg gat aac ctg cgc        432
Ala Lys Gly Thr Ile Asp Leu Asn Leu Pro Leu Ala Asp Asn Leu Arg
        130                 135                 140 aat gta gcg gcg gcg ctc ggc aaa ccg ttg agc gaa ctg acg gta acg        480
Asn Val Ala Ala Ala Leu Gly Lys Pro Leu Ser Glu Leu Thr Val Thr
145                 150                 155                 160 att ctg gct aaa cca cgc cac gat gcc gtt atc gct gaa atg cag caa        528
Ile Leu Ala Lys Pro Arg His Asp Ala Val Ile Ala Glu Met Gln Gln
                165                 170                 175 ctc ggc gta cgc gta ttt gct att ccg gac ggc gac gtt gcg gcc tca        576
Leu Gly Val Arg Val Phe Ala Ile Pro Asp Gly Asp Val Ala Ala Ser
            180                 185                 190 att ctc acc tgt atg cca gac agc gaa gtt gac gtg ctg tac ggt att        624
Ile Leu Thr Cys Met Pro Asp Ser Glu Val Asp Val Leu Tyr Gly Ile
        195                 200                 205 ggt ggc gcg ccg gaa ggc gta gtt tct gcg gcg gtg atc cgc gca tta        672
Gly Gly Ala Pro Glu Gly Val Val Ser Ala Ala Val Ile Arg Ala Leu
210                 215                 220 gat ggc gac atg aac ggt cgt ctg ctg gcg cgt cat gac gtc aaa ggc        720
Asp Gly Asp Met Asn Gly Arg Leu Leu Ala Arg His Asp Val Lys Gly
225                 230                 235                 240 gac aac gaa gag aat cgt cgc att ggc gag cag gag ctg gca cgc tgc        768
Asp Asn Glu Glu Asn Arg Arg Ile Gly Glu Gln Glu Leu Ala Arg Cys
                245                 250                 255 aaa gcg atg ggc atc gaa gcc ggt aaa gta ttg cgc ctg ggc gat atg        816
Lys Ala Met Gly Ile Glu Ala Gly Lys Val Leu Arg Leu Gly Asp Met
            260                 265                 270 gcg cgc agc gat aac gtc atc ttc tct gcc acc ggt att acc aaa ggc        864
Ala Arg Ser Asp Asn Val Ile Phe Ser Ala Thr Gly Ile Thr Lys Gly
        275                 280                 285 gat ctg ctg gaa ggc att agc cgc aaa ggc aat atc gcg act acc gaa        912
Asp Leu Leu Glu Gly Ile Ser Arg Lys Gly Asn Ile Ala Thr Thr Glu
    290                 295                 300 acg ctg ctg atc cgc ggc aag tca cgc acc att cgc cgc att cag tcc        960
Thr Leu Leu Ile Arg Gly Lys Ser Arg Thr Ile Arg Arg Ile Gln Ser
305                 310                 315                 320 atc cac tat ctg gat cgc aaa gac ccg gaa atg cag gtg cac atc ctc       1008
Ile His Tyr Leu Asp Arg Lys Asp Pro Glu Met Gln Val His Ile Leu
                325                 330                 335 tga                                                                    1011

<210> SEQ ID NO 22
<211> LENGTH: 336
<212> TYPE: PRT
<213> ORGANISM: Escherichia coli

<400> SEQUENCE: 22

Met Arg Arg Glu Leu Ala Ile Glu Phe Ser Arg Val Thr Glu Ser Ala
1               5                   10                  15

Ala Leu Ala Gly Tyr Lys Trp Leu Gly Arg Gly Asp Lys Asn Thr Ala
            20                  25                  30

Asp Gly Ala Ala Val Asn Ala Met Arg Ile Met Leu Asn Gln Val Asn
```

```
              35                  40                  45
Ile Asp Gly Thr Ile Val Ile Gly Glu Gly Glu Ile Asp Glu Ala Pro
 50                  55                  60

Met Leu Tyr Ile Gly Glu Lys Val Gly Thr Arg Gly Asp Ala Val
 65                  70                  75                  80

Asp Ile Ala Val Asp Pro Ile Glu Gly Thr Arg Met Thr Ala Met Gly
                 85                  90                  95

Gln Ala Asn Ala Leu Ala Val Leu Ala Val Gly Asp Lys Gly Cys Phe
                100                 105                 110

Leu Asn Ala Pro Asp Met Tyr Met Glu Lys Leu Ile Val Gly Pro Gly
                115                 120                 125

Ala Lys Gly Thr Ile Asp Leu Asn Leu Pro Leu Ala Asp Asn Leu Arg
                130                 135                 140

Asn Val Ala Ala Ala Leu Gly Lys Pro Leu Ser Glu Leu Thr Val Thr
145                 150                 155                 160

Ile Leu Ala Lys Pro Arg His Asp Ala Val Ile Ala Glu Met Gln Gln
                165                 170                 175

Leu Gly Val Arg Val Phe Ala Ile Pro Asp Gly Asp Val Ala Ala Ser
                180                 185                 190

Ile Leu Thr Cys Met Pro Asp Ser Glu Val Asp Val Leu Tyr Gly Ile
                195                 200                 205

Gly Gly Ala Pro Glu Gly Val Val Ser Ala Ala Val Ile Arg Ala Leu
                210                 215                 220

Asp Gly Asp Met Asn Gly Arg Leu Leu Ala Arg His Asp Val Lys Gly
225                 230                 235                 240

Asp Asn Glu Glu Asn Arg Arg Ile Gly Glu Gln Leu Ala Arg Cys
                245                 250                 255

Lys Ala Met Gly Ile Glu Ala Gly Lys Val Leu Arg Leu Gly Asp Met
                260                 265                 270

Ala Arg Ser Asp Asn Val Ile Phe Ser Ala Thr Gly Ile Thr Lys Gly
                275                 280                 285

Asp Leu Leu Glu Gly Ile Ser Arg Lys Gly Asn Ile Ala Thr Thr Glu
                290                 295                 300

Thr Leu Leu Ile Arg Gly Lys Ser Arg Thr Ile Arg Arg Ile Gln Ser
305                 310                 315                 320

Ile His Tyr Leu Asp Arg Lys Asp Pro Glu Met Gln Val His Ile Leu
                325                 330                 335

<210> SEQ ID NO 23
<211> LENGTH: 1143
<212> TYPE: DNA
<213> ORGANISM: Escherichia coli
<220> FEATURE:
<221> NAME/KEY: CDS
<222> LOCATION: (1)..(1143)
<223> OTHER INFORMATION: gldA coding region

<400> SEQUENCE: 23 atg ccg cat ttg gca cta ctc atc tct aaa gga gca att atg gac cgc    48
Met Pro His Leu Ala Leu Leu Ile Ser Lys Gly Ala Ile Met Asp Arg
1               5                   10                  15 att att caa tca ccg ggt aaa tac atc cag ggc gct gat gtg att aat    96
Ile Ile Gln Ser Pro Gly Lys Tyr Ile Gln Gly Ala Asp Val Ile Asn
                20                  25                  30 cgt ctg ggc gaa tac ctg aag ccg ctg gca gaa cgc tgg tta gtg gtg   144
Arg Leu Gly Glu Tyr Leu Lys Pro Leu Ala Glu Arg Trp Leu Val Val
            35                  40                  45
```

| | | | | | | | | | | | | | | | | |
|---|---|---|---|---|---|---|---|---|---|---|---|---|---|---|---|---|
| ggt | gac | aaa | ttt | gtt | tta | ggt | ttt | gct | caa | tcc | act | gtc | gag | aaa | agc | 192 |
| Gly | Asp | Lys | Phe | Val | Leu | Gly | Phe | Ala | Gln | Ser | Thr | Val | Glu | Lys | Ser | |
| 50 | | | | 55 | | | | | 60 | | | | | | | |

| | | | | | | | | | | | | | | | | |
|---|---|---|---|---|---|---|---|---|---|---|---|---|---|---|---|---|
| ttt | aaa | gat | gct | gga | ctg | gta | gta | gaa | att | gcg | ccg | ttt | ggc | ggt | gaa | 240 |
| Phe | Lys | Asp | Ala | Gly | Leu | Val | Val | Glu | Ile | Ala | Pro | Phe | Gly | Gly | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tgt | tcg | caa | aat | gag | atc | gac | cgt | ctg | cgt | ggc | atc | gcg | gag | act | gcg | 288 |
| Cys | Ser | Gln | Asn | Glu | Ile | Asp | Arg | Leu | Arg | Gly | Ile | Ala | Glu | Thr | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | tgt | ggc | gca | att | ctc | ggt | atc | ggt | ggc | gga | aaa | acc | ctc | gat | act | 336 |
| Gln | Cys | Gly | Ala | Ile | Leu | Gly | Ile | Gly | Gly | Gly | Lys | Thr | Leu | Asp | Thr | |
| | | 100 | | | | | 105 | | | | | 110 | | | | |

| | | | | | | | | | | | | | | | | |
|---|---|---|---|---|---|---|---|---|---|---|---|---|---|---|---|---|
| gcc | aaa | gca | ctg | gca | cat | ttc | atg | ggt | gtt | ccg | gta | gcg | atc | gca | ccg | 384 |
| Ala | Lys | Ala | Leu | Ala | His | Phe | Met | Gly | Val | Pro | Val | Ala | Ile | Ala | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| act | atc | gcc | tct | acc | gat | gca | ccg | tgc | agc | gca | ttg | tct | gtt | atc | tac | 432 |
| Thr | Ile | Ala | Ser | Thr | Asp | Ala | Pro | Cys | Ser | Ala | Leu | Ser | Val | Ile | Tyr | |
| 130 | | | | | 135 | | | | | 140 | | | | | | |

| | | | | | | | | | | | | | | | | |
|---|---|---|---|---|---|---|---|---|---|---|---|---|---|---|---|---|
| acc | gat | gag | ggt | gag | ttt | gac | cgc | tat | ctg | ctg | ttg | cca | aat | aac | ccg | 480 |
| Thr | Asp | Glu | Gly | Glu | Phe | Asp | Arg | Tyr | Leu | Leu | Leu | Pro | Asn | Asn | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aat | atg | gtc | att | gtc | gac | acc | aaa | atc | gtc | gct | ggc | gca | cct | gca | cgt | 528 |
| Asn | Met | Val | Ile | Val | Asp | Thr | Lys | Ile | Val | Ala | Gly | Ala | Pro | Ala | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| ctg | tta | gcg | gcg | ggt | atc | ggc | gat | gcg | ctg | gca | acc | tgg | ttt | gaa | gcg | 576 |
| Leu | Leu | Ala | Ala | Gly | Ile | Gly | Asp | Ala | Leu | Ala | Thr | Trp | Phe | Glu | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| cgt | gcc | tgc | tct | cgt | agc | ggc | gcg | acc | acc | atg | gcg | ggc | ggc | aag | tgc | 624 |
| Arg | Ala | Cys | Ser | Arg | Ser | Gly | Ala | Thr | Thr | Met | Ala | Gly | Gly | Lys | Cys | |
| | | 195 | | | | | 200 | | | | | 205 | | | | |

| | | | | | | | | | | | | | | | | |
|---|---|---|---|---|---|---|---|---|---|---|---|---|---|---|---|---|
| acc | cag | gct | gcg | ctg | gca | ctg | gct | gaa | ctg | tgc | tac | aac | acc | ctg | ctg | 672 |
| Thr | Gln | Ala | Ala | Leu | Ala | Leu | Ala | Glu | Leu | Cys | Tyr | Asn | Thr | Leu | Leu | |
| | | 210 | | | | | 215 | | | | | 220 | | | | |

| | | | | | | | | | | | | | | | | |
|---|---|---|---|---|---|---|---|---|---|---|---|---|---|---|---|---|
| gaa | gaa | ggc | gaa | aaa | gcg | atg | ctt | gct | gcc | gaa | cag | cat | gta | gtg | act | 720 |
| Glu | Glu | Gly | Glu | Lys | Ala | Met | Leu | Ala | Ala | Glu | Gln | His | Val | Val | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ccg | gcg | ctg | gag | cgc | gtg | att | gaa | gcg | aac | acc | tat | ttg | agc | ggt | gtt | 768 |
| Pro | Ala | Leu | Glu | Arg | Val | Ile | Glu | Ala | Asn | Thr | Tyr | Leu | Ser | Gly | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| ggt | ttt | gaa | agt | ggt | ggt | ctg | gct | gcg | gcg | cac | gca | gtg | cat | aac | ggc | 816 |
| Gly | Phe | Glu | Ser | Gly | Gly | Leu | Ala | Ala | Ala | His | Ala | Val | His | Asn | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| ctg | acc | gct | atc | ccg | gac | gcg | cat | cac | tat | tat | cac | ggt | gaa | aaa | gtg | 864 |
| Leu | Thr | Ala | Ile | Pro | Asp | Ala | His | His | Tyr | Tyr | His | Gly | Glu | Lys | Val | |
| | | | 275 | | | | | 280 | | | | | 285 | | | |

| | | | | | | | | | | | | | | | | |
|---|---|---|---|---|---|---|---|---|---|---|---|---|---|---|---|---|
| gca | ttc | ggt | acg | ctg | acg | cag | ctg | gtt | ctg | gaa | aat | gcg | ccg | gtg | gag | 912 |
| Ala | Phe | Gly | Thr | Leu | Thr | Gln | Leu | Val | Leu | Glu | Asn | Ala | Pro | Val | Glu | |
| | 290 | | | | | 295 | | | | | 300 | | | | | |

| | | | | | | | | | | | | | | | | |
|---|---|---|---|---|---|---|---|---|---|---|---|---|---|---|---|---|
| gaa | atc | gaa | acc | gta | gct | gcc | ctt | agc | cat | gcg | gta | ggt | ttg | cca | ata | 960 |
| Glu | Ile | Glu | Thr | Val | Ala | Ala | Leu | Ser | His | Ala | Val | Gly | Leu | Pro | Ile | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| act | ctc | gct | caa | ctg | gat | att | aaa | gaa | gat | gtc | ccg | gcg | aaa | atg | cga | 1008 |
| Thr | Leu | Ala | Gln | Leu | Asp | Ile | Lys | Glu | Asp | Val | Pro | Ala | Lys | Met | Arg | |
| | | | 325 | | | | | 330 | | | | | 335 | | | |

| | | | | | | | | | | | | | | | | |
|---|---|---|---|---|---|---|---|---|---|---|---|---|---|---|---|---|
| att | gtg | gca | gaa | gcg | gca | tgt | gca | gaa | ggt | gaa | acc | att | cac | aac | atg | 1056 |
| Ile | Val | Ala | Glu | Ala | Ala | Cys | Ala | Glu | Gly | Glu | Thr | Ile | His | Asn | Met | |
| | | | 340 | | | | | 345 | | | | | 350 | | | |

| | | | | | | | | | | | | | | | | |
|---|---|---|---|---|---|---|---|---|---|---|---|---|---|---|---|---|
| cct | ggc | ggc | gcg | acg | cca | gat | cag | gtt | tac | gcc | gct | ctg | ctg | gta | gcc | 1104 |
| Pro | Gly | Gly | Ala | Thr | Pro | Asp | Gln | Val | Tyr | Ala | Ala | Leu | Leu | Val | Ala | |

```
                   355                 360                 365
         gac cag tac ggt cag cgt ttc ctg caa gag tgg gaa taa                 1143
         Asp Gln Tyr Gly Gln Arg Phe Leu Gln Glu Trp Glu
             370                 375                 380

<210> SEQ ID NO 24
<211> LENGTH: 380
<212> TYPE: PRT
<213> ORGANISM: Escherichia coli

<400> SEQUENCE: 24
```

Met Pro His Leu Ala Leu Leu Ile Ser Lys Gly Ala Ile Met Asp Arg
1               5                   10                  15

Ile Ile Gln Ser Pro Gly Lys Tyr Ile Gln Gly Ala Asp Val Ile Asn
            20                  25                  30

Arg Leu Gly Glu Tyr Leu Lys Pro Leu Ala Glu Arg Trp Leu Val Val
        35                  40                  45

Gly Asp Lys Phe Val Leu Gly Phe Ala Gln Ser Thr Val Glu Lys Ser
    50                  55                  60

Phe Lys Asp Ala Gly Leu Val Val Glu Ile Ala Pro Phe Gly Gly Glu
65                  70                  75                  80

Cys Ser Gln Asn Glu Ile Asp Arg Leu Arg Gly Ile Ala Glu Thr Ala
                85                  90                  95

Gln Cys Gly Ala Ile Leu Gly Ile Gly Gly Gly Lys Thr Leu Asp Thr
            100                 105                 110

Ala Lys Ala Leu Ala His Phe Met Gly Val Pro Val Ala Ile Ala Pro
        115                 120                 125

Thr Ile Ala Ser Thr Asp Ala Pro Cys Ser Ala Leu Ser Val Ile Tyr
130                 135                 140

Thr Asp Glu Gly Glu Phe Asp Arg Tyr Leu Leu Leu Pro Asn Asn Pro
145                 150                 155                 160

Asn Met Val Ile Val Asp Thr Lys Ile Val Ala Gly Ala Pro Ala Arg
                165                 170                 175

Leu Leu Ala Ala Gly Ile Gly Asp Ala Leu Ala Thr Trp Phe Glu Ala
            180                 185                 190

Arg Ala Cys Ser Arg Ser Gly Ala Thr Thr Met Ala Gly Gly Lys Cys
        195                 200                 205

Thr Gln Ala Ala Leu Ala Leu Ala Glu Leu Cys Tyr Asn Thr Leu Leu
210                 215                 220

Glu Glu Gly Glu Lys Ala Met Leu Ala Ala Glu Gln His Val Val Thr
225                 230                 235                 240

Pro Ala Leu Glu Arg Val Ile Glu Ala Asn Thr Tyr Leu Ser Gly Val
                245                 250                 255

Gly Phe Glu Ser Gly Gly Leu Ala Ala Ala His Ala Val His Asn Gly
            260                 265                 270

Leu Thr Ala Ile Pro Asp Ala His His Tyr Tyr His Gly Glu Lys Val
        275                 280                 285

Ala Phe Gly Thr Leu Thr Gln Leu Val Leu Glu Asn Ala Pro Val Glu
    290                 295                 300

Glu Ile Glu Thr Val Ala Ala Leu Ser His Ala Val Gly Leu Pro Ile
305                 310                 315                 320

Thr Leu Ala Gln Leu Asp Ile Lys Glu Asp Val Pro Ala Lys Met Arg
                325                 330                 335

Ile Val Ala Glu Ala Ala Cys Ala Glu Gly Glu Thr Ile His Asn Met
            340                 345                 350

```
Pro Gly Gly Ala Thr Pro Asp Gln Val Tyr Ala Ala Leu Leu Val Ala
        355                 360                 365

Asp Gln Tyr Gly Gln Arg Phe Leu Gln Glu Trp Glu
    370                 375                 380

<210> SEQ ID NO 25
<211> LENGTH: 1101
<212> TYPE: DNA
<213> ORGANISM: Escherichia coli
<220> FEATURE:
<221> NAME/KEY: CDS
<222> LOCATION: (1)..(1101)
<223> OTHER INFORMATION: dhaK coding region

<400> SEQUENCE: 25 atg ccc tac cgt aat tgc tgg agc aaa ata atg aaa aaa ttg atc aat      48
Met Pro Tyr Arg Asn Cys Trp Ser Lys Ile Met Lys Lys Leu Ile Asn
 1               5                  10                  15 gat gtg caa gac gta ctg gac gaa caa ctg gca gga ctg gcg aaa gcg      96
Asp Val Gln Asp Val Leu Asp Glu Gln Leu Ala Gly Leu Ala Lys Ala
             20                  25                  30 cat cca tcg ctg aca ctg cat cag gat ccg gtg tat gtc acc cga gct     144
His Pro Ser Leu Thr Leu His Gln Asp Pro Val Tyr Val Thr Arg Ala
         35                  40                  45 gat gcc cct gtt gca gga aaa gtc gcc ctg ctg tcg ggt ggc ggc agc     192
Asp Ala Pro Val Ala Gly Lys Val Ala Leu Leu Ser Gly Gly Gly Ser
     50                  55                  60 gga cac gag ccg atg cac tgt ggt tat atc ggt cag ggg atg ctt tcg     240
Gly His Glu Pro Met His Cys Gly Tyr Ile Gly Gln Gly Met Leu Ser
65                  70                  75                  80 ggg gcc tgt ccg ggc gaa att ttc acc tca ccg acg ccc gat aaa atc     288
Gly Ala Cys Pro Gly Glu Ile Phe Thr Ser Pro Thr Pro Asp Lys Ile
                 85                  90                  95 ttt gaa tgc gcc atg caa gtt gat ggc ggc gaa ggt gta ctg ttg att     336
Phe Glu Cys Ala Met Gln Val Asp Gly Gly Glu Gly Val Leu Leu Ile
            100                 105                 110 atc aaa aat tac acc ggc gat att ctt aac ttt gaa aca gcg acc gag     384
Ile Lys Asn Tyr Thr Gly Asp Ile Leu Asn Phe Glu Thr Ala Thr Glu
        115                 120                 125 tta ctg cac gat agc ggc gta aaa gtg acc act gtg gtc att gat gac     432
Leu Leu His Asp Ser Gly Val Lys Val Thr Thr Val Val Ile Asp Asp
    130                 135                 140 gac gtt gcg gta aaa gac agt ctt tat act gcc ggg cga cgc ggc gtt     480
Asp Val Ala Val Lys Asp Ser Leu Tyr Thr Ala Gly Arg Arg Gly Val
145                 150                 155                 160 gcc aac acc gta tta att gaa aaa ctc gta ggc gca gcg gag cgt         528
Ala Asn Thr Val Leu Ile Glu Lys Leu Val Gly Ala Ala Glu Arg
                165                 170                 175 ggc gac tca ctg gac gcc tgt gcg gaa ctg ggg cgt aag ctg aat aat     576
Gly Asp Ser Leu Asp Ala Cys Ala Glu Leu Gly Arg Lys Leu Asn Asn
            180                 185                 190 caa ggc cac tca ata ggt atc gct ctc ggt gcc tgt acc gtt cct gcc     624
Gln Gly His Ser Ile Gly Ile Ala Leu Gly Ala Cys Thr Val Pro Ala
        195                 200                 205 gcg ggc aaa cct tct ttt acc ctg gcg gat aat gag atg gag ttt ggc     672
Ala Gly Lys Pro Ser Phe Thr Leu Ala Asp Asn Glu Met Glu Phe Gly
    210                 215                 220 gtc ggc att cat ggt gag ccg ggt att gac cgc cgc ccc ttc tct tcc     720
Val Gly Ile His Gly Glu Pro Gly Ile Asp Arg Arg Pro Phe Ser Ser
225                 230                 235                 240
```

| | |
|---|---|
| ctt gat caa acc gtc gat gaa atg ttc gac acc ctg ctg gta aat ggc<br>Leu Asp Gln Thr Val Asp Glu Met Phe Asp Thr Leu Leu Val Asn Gly<br>245 250 255 | 768 |
| tca tac cat cgc act ttg cgt ttc tgg gat tat caa caa ggc agt tgg<br>Ser Tyr His Arg Thr Leu Arg Phe Trp Asp Tyr Gln Gln Gly Ser Trp<br>260 265 270 | 816 |
| cag gaa gaa caa caa acc aaa caa ccg ctc cag tct ggc gat cgg gtg<br>Gln Glu Glu Gln Gln Thr Lys Gln Pro Leu Gln Ser Gly Asp Arg Val<br>275 280 285 | 864 |
| att gcg ctg gtt aac aat ctt ggc gca act ccg ctt tct gag ctg tac<br>Ile Ala Leu Val Asn Asn Leu Gly Ala Thr Pro Leu Ser Glu Leu Tyr<br>290 295 300 | 912 |
| ggc gtc tat aac cgc ctg acc aca cgt tgc cag caa gcg gga ttg act<br>Gly Val Tyr Asn Arg Leu Thr Thr Arg Cys Gln Gln Ala Gly Leu Thr<br>305 310 315 320 | 960 |
| atc gaa cgt aat tta att ggc gcg tac tgc acc tca ctg gat atg acc<br>Ile Glu Arg Asn Leu Ile Gly Ala Tyr Cys Thr Ser Leu Asp Met Thr<br>325 330 335 | 1008 |
| ggt ttc tca atc acc tta ctg aaa gtt gat gac gaa acg ctg gca ctc<br>Gly Phe Ser Ile Thr Leu Leu Lys Val Asp Asp Glu Thr Leu Ala Leu<br>340 345 350 | 1056 |
| tgg gac gcc ccg gtc cac acc ccg gcc ctt aac tgg ggt aaa taa<br>Trp Asp Ala Pro Val His Thr Pro Ala Leu Asn Trp Gly Lys<br>355 360 365 | 1101 |

```
<210> SEQ ID NO 26
<211> LENGTH: 366
<212> TYPE: PRT
<213> ORGANISM: Escherichia coli

<400> SEQUENCE: 26

Met Pro Tyr Arg Asn Cys Trp Ser Lys Ile Met Lys Lys Leu Ile Asn
1               5                   10                  15

Asp Val Gln Asp Val Leu Asp Glu Gln Leu Ala Gly Leu Ala Lys Ala
                20                  25                  30

His Pro Ser Leu Thr Leu His Gln Asp Pro Val Tyr Val Thr Arg Ala
            35                  40                  45

Asp Ala Pro Val Ala Gly Lys Val Ala Leu Leu Ser Gly Gly Gly Ser
        50                  55                  60

Gly His Glu Pro Met His Cys Gly Tyr Ile Gly Gln Gly Met Leu Ser
65                  70                  75                  80

Gly Ala Cys Pro Gly Glu Ile Phe Thr Ser Pro Thr Pro Asp Lys Ile
                85                  90                  95

Phe Glu Cys Ala Met Gln Val Asp Gly Gly Glu Gly Val Leu Leu Ile
                100                 105                 110

Ile Lys Asn Tyr Thr Gly Asp Ile Leu Asn Phe Glu Thr Ala Thr Glu
            115                 120                 125

Leu Leu His Asp Ser Gly Val Lys Val Thr Thr Val Ile Asp Asp
        130                 135                 140

Asp Val Ala Val Lys Asp Ser Leu Tyr Thr Ala Gly Arg Arg Gly Val
145                 150                 155                 160

Ala Asn Thr Val Leu Ile Glu Lys Leu Val Gly Ala Ala Ala Glu Arg
                165                 170                 175

Gly Asp Ser Leu Asp Ala Cys Ala Glu Leu Gly Arg Lys Leu Asn Asn
            180                 185                 190

Gln Gly His Ser Ile Gly Ile Ala Leu Gly Ala Cys Thr Val Pro Ala
        195                 200                 205
```

```
Ala Gly Lys Pro Ser Phe Thr Leu Ala Asp Asn Glu Met Glu Phe Gly
    210                 215                 220

Val Gly Ile His Gly Glu Pro Gly Ile Asp Arg Arg Pro Phe Ser Ser
225                 230                 235                 240

Leu Asp Gln Thr Val Asp Glu Met Phe Asp Thr Leu Leu Val Asn Gly
                245                 250                 255

Ser Tyr His Arg Thr Leu Arg Phe Trp Asp Tyr Gln Gln Gly Ser Trp
            260                 265                 270

Gln Glu Gln Gln Thr Lys Gln Pro Leu Gln Ser Gly Asp Arg Val
            275                 280                 285

Ile Ala Leu Val Asn Asn Leu Gly Ala Thr Pro Leu Ser Glu Leu Tyr
    290                 295                 300

Gly Val Tyr Asn Arg Leu Thr Thr Arg Cys Gln Gln Ala Gly Leu Thr
305                 310                 315                 320

Ile Glu Arg Asn Leu Ile Gly Ala Tyr Cys Thr Ser Leu Asp Met Thr
                325                 330                 335

Gly Phe Ser Ile Thr Leu Leu Lys Val Asp Asp Glu Thr Leu Ala Leu
            340                 345                 350

Trp Asp Ala Pro Val His Thr Pro Ala Leu Asn Trp Gly Lys
            355                 360                 365

<210> SEQ ID NO 27
<211> LENGTH: 633
<212> TYPE: DNA
<213> ORGANISM: Escherichia coli
<220> FEATURE:
<221> NAME/KEY: CDS
<222> LOCATION: (1)..(633)
<223> OTHER INFORMATION: dhaL coding region

<400> SEQUENCE: 27 atg tca ctg agc aga act caa att gtt aac tgg ctc act cgt tgt ggc     48
Met Ser Leu Ser Arg Thr Gln Ile Val Asn Trp Leu Thr Arg Cys Gly
1               5                   10                  15 gat att ttc agc acc gag agc gag tat ctt acc gga ctg gat cgc gaa     96
Asp Ile Phe Ser Thr Glu Ser Glu Tyr Leu Thr Gly Leu Asp Arg Glu
                20                  25                  30 att ggc gat gct gac cac ggg cta aat atg aac cga ggc ttt agc aaa    144
Ile Gly Asp Ala Asp His Gly Leu Asn Met Asn Arg Gly Phe Ser Lys
            35                  40                  45 gtg gtg gaa aaa ctc cct gct atc gca gat aaa gat atc ggt ttc att    192
Val Val Glu Lys Leu Pro Ala Ile Ala Asp Lys Asp Ile Gly Phe Ile
        50                  55                  60 ctc aag aat acc ggt atg acg ctg ctt tcc agc gtc ggt ggt gcc agt    240
Leu Lys Asn Thr Gly Met Thr Leu Leu Ser Ser Val Gly Gly Ala Ser
65                  70                  75                  80 ggt ccg ctg ttc ggt acc ttc ttt atc cgc gcc gca cag gcg acc cag    288
Gly Pro Leu Phe Gly Thr Phe Phe Ile Arg Ala Ala Gln Ala Thr Gln
                85                  90                  95 gca cgg caa agc ctg aca ctg gaa gag ctt tat cag atg ttc cgc gat    336
Ala Arg Gln Ser Leu Thr Leu Glu Glu Leu Tyr Gln Met Phe Arg Asp
            100                 105                 110 ggc gcg gac ggc gta atc agt cgc ggg aaa gcc gaa cct ggc gat aaa    384
Gly Ala Asp Gly Val Ile Ser Arg Gly Lys Ala Glu Pro Gly Asp Lys
        115                 120                 125 acc atg tgt gat gtg tgg gtg ccg gtg gtg gaa tcg tta cgt cag tcc    432
Thr Met Cys Asp Val Trp Val Pro Val Val Glu Ser Leu Arg Gln Ser
130                 135                 140 agc gag caa aat ctc tct gtt ccg gtg gcg ctc gaa gct gcc agt agc    480
Ser Glu Gln Asn Leu Ser Val Pro Val Ala Leu Glu Ala Ala Ser Ser
```

```
Ser Glu Gln Asn Leu Ser Val Pro Val Ala Leu Glu Ala Ala Ser Ser
145                 150                 155                 160 atc gcc gaa tcc gct gca caa agt acg att acg atg caa gcc cgc aaa      528
Ile Ala Glu Ser Ala Ala Gln Ser Thr Ile Thr Met Gln Ala Arg Lys
                165                 170                 175 ggc cgc gcc agt tat ctc ggt gaa cgc agt att ggt cac cag gat ccc      576
Gly Arg Ala Ser Tyr Leu Gly Glu Arg Ser Ile Gly His Gln Asp Pro
            180                 185                 190 ggc gcg acc tcg gtg atg ttt atg atg caa atg ttg gcg tta gcc gca      624
Gly Ala Thr Ser Val Met Phe Met Met Gln Met Leu Ala Leu Ala Ala
        195                 200                 205 aaa gag taa                                                          633
Lys Glu
    210

<210> SEQ ID NO 28
<211> LENGTH: 210
<212> TYPE: PRT
<213> ORGANISM: Escherichia coli

<400> SEQUENCE: 28

Met Ser Leu Ser Arg Thr Gln Ile Val Asn Trp Leu Thr Arg Cys Gly
1               5                   10                  15

Asp Ile Phe Ser Thr Glu Ser Glu Tyr Leu Thr Gly Leu Asp Arg Glu
                20                  25                  30

Ile Gly Asp Ala Asp His Gly Leu Asn Met Asn Arg Gly Phe Ser Lys
            35                  40                  45

Val Val Glu Lys Leu Pro Ala Ile Ala Asp Lys Asp Ile Gly Phe Ile
    50                  55                  60

Leu Lys Asn Thr Gly Met Thr Leu Leu Ser Ser Val Gly Gly Ala Ser
65                  70                  75                  80

Gly Pro Leu Phe Gly Thr Phe Phe Ile Arg Ala Ala Gln Ala Thr Gln
                85                  90                  95

Ala Arg Gln Ser Leu Thr Leu Glu Glu Leu Tyr Gln Met Phe Arg Asp
            100                 105                 110

Gly Ala Asp Gly Val Ile Ser Arg Gly Lys Ala Glu Pro Gly Asp Lys
        115                 120                 125

Thr Met Cys Asp Val Trp Val Pro Val Val Glu Ser Leu Arg Gln Ser
130                 135                 140

Ser Glu Gln Asn Leu Ser Val Pro Val Ala Leu Glu Ala Ala Ser Ser
145                 150                 155                 160

Ile Ala Glu Ser Ala Ala Gln Ser Thr Ile Thr Met Gln Ala Arg Lys
                165                 170                 175

Gly Arg Ala Ser Tyr Leu Gly Glu Arg Ser Ile Gly His Gln Asp Pro
            180                 185                 190

Gly Ala Thr Ser Val Met Phe Met Met Gln Met Leu Ala Leu Ala Ala
        195                 200                 205

Lys Glu
    210

<210> SEQ ID NO 29
<211> LENGTH: 1422
<212> TYPE: DNA
<213> ORGANISM: Escherichia coli
<220> FEATURE:
<221> NAME/KEY: CDS
<222> LOCATION: (1)..(1422)
<223> OTHER INFORMATION: dhaM coding region
```

-continued

<400> SEQUENCE: 29

| | | | | | | | | | | | | | | | | |
|---|---|---|---|---|---|---|---|---|---|---|---|---|---|---|---|---|
| gtg | atg | gta | aac | ctg | gtc | ata | gtt | tca | cat | agc | agc | cga | ctg | gga | gaa | 48 |
| Val | Met | Val | Asn | Leu | Val | Ile | Val | Ser | His | Ser | Ser | Arg | Leu | Gly | Glu | |
| 1 | | | | 5 | | | | | 10 | | | | | 15 | | |
| ggt | gtc | ggt | gaa | tta | gcc | cgt | cag | atg | tta | atg | agt | gat | agt | tgt | aaa | 96 |
| Gly | Val | Gly | Glu | Leu | Ala | Arg | Gln | Met | Leu | Met | Ser | Asp | Ser | Cys | Lys | |
| | | | 20 | | | | | 25 | | | | | 30 | | | |
| atc | gcc | att | gcc | gcg | gga | att | gac | gat | cca | caa | aat | ccc | att | ggt | acc | 144 |
| Ile | Ala | Ile | Ala | Ala | Gly | Ile | Asp | Asp | Pro | Gln | Asn | Pro | Ile | Gly | Thr | |
| | | 35 | | | | | 40 | | | | | 45 | | | | |
| gat | gcc | gtc | aaa | gtg | atg | gag | gcc | atc | gaa | tct | gtt | gct | gat | gcc | gac | 192 |
| Asp | Ala | Val | Lys | Val | Met | Glu | Ala | Ile | Glu | Ser | Val | Ala | Asp | Ala | Asp | |
| | 50 | | | | | 55 | | | | | 60 | | | | | |
| cat | gtg | ctg | gtc | atg | atg | gat | atg | ggt | agc | gca | tta | ttg | agt | gct | gaa | 240 |
| His | Val | Leu | Val | Met | Met | Asp | Met | Gly | Ser | Ala | Leu | Leu | Ser | Ala | Glu | |
| 65 | | | | | 70 | | | | | 75 | | | | | 80 | |
| act | gcg | ctg | gaa | ttg | ctg | gct | ccc | gag | atc | gcc | gca | aaa | gta | cgt | ttg | 288 |
| Thr | Ala | Leu | Glu | Leu | Leu | Ala | Pro | Glu | Ile | Ala | Ala | Lys | Val | Arg | Leu | |
| | | | | 85 | | | | | 90 | | | | | 95 | | |
| tgt | gct | gcg | ccg | ttg | gtc | gaa | ggt | aca | ctg | gca | gca | acg | gtc | agc | gcg | 336 |
| Cys | Ala | Ala | Pro | Leu | Val | Glu | Gly | Thr | Leu | Ala | Ala | Thr | Val | Ser | Ala | |
| | | | 100 | | | | | 105 | | | | | 110 | | | |
| gcc | tcg | ggg | gcg | gat | atc | gac | aaa | gtt | atc | ttt | gac | gcc | atg | cat | gcg | 384 |
| Ala | Ser | Gly | Ala | Asp | Ile | Asp | Lys | Val | Ile | Phe | Asp | Ala | Met | His | Ala | |
| | | 115 | | | | | 120 | | | | | 125 | | | | |
| ctg | gaa | gcc | aaa | cgt | gaa | caa | ctg | ggt | tta | ccg | tcc | tcc | gac | act | gaa | 432 |
| Leu | Glu | Ala | Lys | Arg | Glu | Gln | Leu | Gly | Leu | Pro | Ser | Ser | Asp | Thr | Glu | |
| | 130 | | | | | 135 | | | | | 140 | | | | | |
| atc | tct | gac | aca | tgt | cct | gcg | tac | gat | gaa | gaa | gcc | cgt | tct | ctg | gcg | 480 |
| Ile | Ser | Asp | Thr | Cys | Pro | Ala | Tyr | Asp | Glu | Glu | Ala | Arg | Ser | Leu | Ala | |
| 145 | | | | | 150 | | | | | 155 | | | | | 160 | |
| gtg | gtc | ata | aaa | aac | cgt | aac | ggc | ctg | cat | gta | cgt | ccg | gcc | tcc | cgg | 528 |
| Val | Val | Ile | Lys | Asn | Arg | Asn | Gly | Leu | His | Val | Arg | Pro | Ala | Ser | Arg | |
| | | | | 165 | | | | | 170 | | | | | 175 | | |
| ctg | gtt | tat | acc | tta | tcg | aca | ttt | aat | gcc | gat | atg | ttg | ctg | gaa | aaa | 576 |
| Leu | Val | Tyr | Thr | Leu | Ser | Thr | Phe | Asn | Ala | Asp | Met | Leu | Leu | Glu | Lys | |
| | | | 180 | | | | | 185 | | | | | 190 | | | |
| aac | ggc | aaa | tgc | gtc | aca | cca | gag | agt | att | aac | cag | att | gcg | tta | cta | 624 |
| Asn | Gly | Lys | Cys | Val | Thr | Pro | Glu | Ser | Ile | Asn | Gln | Ile | Ala | Leu | Leu | |
| | | 195 | | | | | 200 | | | | | 205 | | | | |
| caa | gtt | cgc | tat | aac | gat | acg | ctg | cgc | ctg | att | gcg | aaa | ggg | cca | gaa | 672 |
| Gln | Val | Arg | Tyr | Asn | Asp | Thr | Leu | Arg | Leu | Ile | Ala | Lys | Gly | Pro | Glu | |
| | 210 | | | | | 215 | | | | | 220 | | | | | |
| gct | gaa | gag | gca | ctg | atc | gct | ttc | cgt | cag | ctg | gct | gaa | gat | aac | ttt | 720 |
| Ala | Glu | Glu | Ala | Leu | Ile | Ala | Phe | Arg | Gln | Leu | Ala | Glu | Asp | Asn | Phe | |
| 225 | | | | | 230 | | | | | 235 | | | | | 240 | |
| ggt | gaa | acg | gag | gaa | gtc | gct | cca | cct | act | ctg | cgt | ccc | gtt | ccg | cct | 768 |
| Gly | Glu | Thr | Glu | Glu | Val | Ala | Pro | Pro | Thr | Leu | Arg | Pro | Val | Pro | Pro | |
| | | | | 245 | | | | | 250 | | | | | 255 | | |
| gtt | tcg | ggt | aaa | gcc | ttt | tat | tat | caa | cca | gtt | tta | tgt | acg | gta | cag | 816 |
| Val | Ser | Gly | Lys | Ala | Phe | Tyr | Tyr | Gln | Pro | Val | Leu | Cys | Thr | Val | Gln | |
| | | | 260 | | | | | 265 | | | | | 270 | | | |
| gca | aaa | tca | acc | ctg | acc | gtg | gaa | gaa | gaa | caa | gat | cga | tta | cgc | cag | 864 |
| Ala | Lys | Ser | Thr | Leu | Thr | Val | Glu | Glu | Glu | Gln | Asp | Arg | Leu | Arg | Gln | |
| | | 275 | | | | | 280 | | | | | 285 | | | | |
| gct | att | gac | ttc | acg | tta | tta | gat | ctg | atg | acg | tta | aca | gcg | aaa | gca | 912 |
| Ala | Ile | Asp | Phe | Thr | Leu | Leu | Asp | Leu | Met | Thr | Leu | Thr | Ala | Lys | Ala | |
| | 290 | | | | | 295 | | | | | 300 | | | | | |
| gaa | gcc | agc | ggg | ctt | gac | gat | att | gcc | gca | atc | ttt | tct | ggt | cac | cat | 960 |

```
Glu Ala Ser Gly Leu Asp Asp Ile Ala Ala Ile Phe Ser Gly His His
305                 310                 315                 320 aca ctg tta gat gat ccg gaa ctg ctg gcg gcg gca agc gaa ctc ctt      1008
Thr Leu Leu Asp Asp Pro Glu Leu Leu Ala Ala Ala Ser Glu Leu Leu
                325                 330                 335 cag cat gaa cat tgc acg gca gaa tat gcc tgg cag caa gtt ctt aaa      1056
Gln His Glu His Cys Thr Ala Glu Tyr Ala Trp Gln Gln Val Leu Lys
            340                 345                 350 gaa ctt agc cag caa tac cag caa ctg gat gat gaa tat cta caa gct      1104
Glu Leu Ser Gln Gln Tyr Gln Gln Leu Asp Asp Glu Tyr Leu Gln Ala
        355                 360                 365 cgc tat att gat gtg gac gat ctt ctg cat cgc acc ctg gtc cac ctg      1152
Arg Tyr Ile Asp Val Asp Asp Leu Leu His Arg Thr Leu Val His Leu
    370                 375                 380 acc caa acg aaa gaa gaa ctc ccg cag ttt aac tcg cca act att cta      1200
Thr Gln Thr Lys Glu Glu Leu Pro Gln Phe Asn Ser Pro Thr Ile Leu
385                 390                 395                 400 ctg gcg gag aac att tat cct tcc aca gta ctg caa ctg gat ccg gcg      1248
Leu Ala Glu Asn Ile Tyr Pro Ser Thr Val Leu Gln Leu Asp Pro Ala
                405                 410                 415 gtt gta aaa ggt atc tgc ctt agc gcc gga agt ccg gta tcc cac agc      1296
Val Val Lys Gly Ile Cys Leu Ser Ala Gly Ser Pro Val Ser His Ser
            420                 425                 430 gcc cta atc gcc cgt gaa ctg ggg att ggc tgg att tgc cag cag ggt      1344
Ala Leu Ile Ala Arg Glu Leu Gly Ile Gly Trp Ile Cys Gln Gln Gly
        435                 440                 445 gag aaa ctg tat gcg ata caa cca gaa gaa acg cta acg ctg gac gtt      1392
Glu Lys Leu Tyr Ala Ile Gln Pro Glu Glu Thr Leu Thr Leu Asp Val
    450                 455                 460 aaa acg caa cgt ttc aac cgt cag ggt taa                              1422
Lys Thr Gln Arg Phe Asn Arg Gln Gly
465                 470

<210> SEQ ID NO 30
<211> LENGTH: 473
<212> TYPE: PRT
<213> ORGANISM: Escherichia coli

<400> SEQUENCE: 30

Val Met Val Asn Leu Val Ile Val Ser His Ser Ser Arg Leu Gly Glu
1               5                   10                  15

Gly Val Gly Glu Leu Ala Arg Gln Met Leu Met Ser Asp Ser Cys Lys
                20                  25                  30

Ile Ala Ile Ala Ala Gly Ile Asp Asp Pro Gln Asn Pro Ile Gly Thr
            35                  40                  45

Asp Ala Val Lys Val Met Glu Ala Ile Glu Ser Val Ala Asp Ala Asp
        50                  55                  60

His Val Leu Val Met Met Asp Met Gly Ser Ala Leu Leu Ser Ala Glu
65                  70                  75                  80

Thr Ala Leu Glu Leu Leu Ala Pro Glu Ile Ala Ala Lys Val Arg Leu
                85                  90                  95

Cys Ala Ala Pro Leu Val Glu Gly Thr Leu Ala Ala Thr Val Ser Ala
            100                 105                 110

Ala Ser Gly Ala Asp Ile Asp Lys Val Ile Phe Asp Ala Met His Ala
        115                 120                 125

Leu Glu Ala Lys Arg Glu Gln Leu Gly Leu Pro Ser Ser Asp Thr Glu
    130                 135                 140

Ile Ser Asp Thr Cys Pro Ala Tyr Asp Glu Glu Ala Arg Ser Leu Ala
```

```
                        145                 150                 155                 160
    Val Val Ile Lys Asn Arg Asn Gly Leu His Val Arg Pro Ala Ser Arg
                    165                 170                 175

Leu Val Tyr Thr Leu Ser Thr Phe Asn Ala Asp Met Leu Leu Glu Lys
                180                 185                 190

Asn Gly Lys Cys Val Thr Pro Glu Ser Ile Asn Gln Ile Ala Leu Leu
            195                 200                 205

Gln Val Arg Tyr Asn Asp Thr Leu Arg Leu Ile Ala Lys Gly Pro Glu
        210                 215                 220

Ala Glu Glu Ala Leu Ile Ala Phe Arg Gln Leu Ala Glu Asp Asn Phe
    225                 230                 235                 240

Gly Glu Thr Glu Val Ala Pro Pro Thr Leu Arg Pro Val Pro Pro
                    245                 250                 255

Val Ser Gly Lys Ala Phe Tyr Tyr Gln Pro Val Leu Cys Thr Val Gln
                260                 265                 270

Ala Lys Ser Thr Leu Thr Val Glu Glu Glu Gln Asp Arg Leu Arg Gln
            275                 280                 285

Ala Ile Asp Phe Thr Leu Leu Asp Leu Met Thr Leu Thr Ala Lys Ala
        290                 295                 300

Glu Ala Ser Gly Leu Asp Asp Ile Ala Ala Ile Phe Ser Gly His His
    305                 310                 315                 320

Thr Leu Leu Asp Asp Pro Glu Leu Leu Ala Ala Ala Ser Glu Leu Leu
                    325                 330                 335

Gln His Glu His Cys Thr Ala Gly Tyr Ala Trp Gln Gln Val Leu Lys
                340                 345                 350

Glu Leu Ser Gln Gln Tyr Gln Gln Leu Asp Asp Glu Tyr Leu Gln Ala
            355                 360                 365

Arg Tyr Ile Asp Val Asp Asp Leu Leu His Arg Thr Leu Val His Leu
        370                 375                 380

Thr Gln Thr Lys Glu Glu Leu Pro Gln Phe Asn Ser Pro Thr Ile Leu
    385                 390                 395                 400

Leu Ala Glu Asn Ile Tyr Pro Ser Thr Val Leu Gln Leu Asp Pro Ala
                    405                 410                 415

Val Val Lys Gly Ile Cys Leu Ser Ala Gly Ser Pro Val Ser His Ser
                420                 425                 430

Ala Leu Ile Ala Arg Glu Leu Gly Ile Gly Trp Ile Cys Gln Gln Gly
            435                 440                 445

Glu Lys Leu Tyr Ala Ile Gln Pro Glu Glu Thr Leu Thr Leu Asp Val
        450                 455                 460

Lys Thr Gln Arg Phe Asn Arg Gln Gly
    465                 470

<210> SEQ ID NO 31
<211> LENGTH: 1929
<212> TYPE: DNA
<213> ORGANISM: Escherichia coli
<220> FEATURE:
<221> NAME/KEY: CDS
<222> LOCATION: (1)..(1929)
<223> OTHER INFORMATION: dhaR coding region

<400> SEQUENCE: 31 atg cgg gat atg agt ggc gct ttt aac aac gat ggt cgg ggc ata tct         48
Met Arg Asp Met Ser Gly Ala Phe Asn Asn Asp Gly Arg Gly Ile Ser
1               5                   10                  15 ccc tta att gca acc tcc tgg gag cga tgc aat aag ctg atg aaa cgg        96
```

```
        Pro Leu Ile Ala Thr Ser Trp Glu Arg Cys Asn Lys Leu Met Lys Arg
                         20                  25                  30 gag aca tgg aac gta cca cat cag gcc cag ggc gtg aca ttt gct tct         144
Glu Thr Trp Asn Val Pro His Gln Ala Gln Gly Val Thr Phe Ala Ser
             35                  40                  45 att tat cgg cgt aag aaa gcg atg ctg acg ctc ggg cag gct gcg ctg         192
Ile Tyr Arg Arg Lys Lys Ala Met Leu Thr Leu Gly Gln Ala Ala Leu
 50                  55                  60 gaa gat gcc tgg gaa tat atg gca ccg cga gag tgt gcg ctg ttt atc         240
Glu Asp Ala Trp Glu Tyr Met Ala Pro Arg Glu Cys Ala Leu Phe Ile
 65                  70                  75                  80 ctc gat gaa acc gcc tgc att ctc agc cgt aat ggc gat ccg caa acc         288
Leu Asp Glu Thr Ala Cys Ile Leu Ser Arg Asn Gly Asp Pro Gln Thr
                 85                  90                  95 ttg cag cag cta agt gca ctg gga ttc aat gac ggc acg tat tgc gcc         336
Leu Gln Gln Leu Ser Ala Leu Gly Phe Asn Asp Gly Thr Tyr Cys Ala
            100                 105                 110 gag gga att att ggt act tgt gcg cta tcg tta gcg gct atc tct ggt         384
Glu Gly Ile Ile Gly Thr Cys Ala Leu Ser Leu Ala Ala Ile Ser Gly
            115                 120                 125 cag gcc gtg aaa acg atg gcc gat caa cat ttc aaa cag gta ctc tgg         432
Gln Ala Val Lys Thr Met Ala Asp Gln His Phe Lys Gln Val Leu Trp
130                 135                 140 aac tgg gcc ttt tgt gca acg ccg ttg ttt gac agc aag ggc cga ttg         480
Asn Trp Ala Phe Cys Ala Thr Pro Leu Phe Asp Ser Lys Gly Arg Leu
145                 150                 155                 160 acg gga aca ata gcg ctg gcg tgt ccg gtt gag caa act acc gca gct         528
Thr Gly Thr Ile Ala Leu Ala Cys Pro Val Glu Gln Thr Thr Ala Ala
                165                 170                 175 gat ttg ccg ttg acg ttg gca atc gcc cgc gag gtc gga aat tta ctg         576
Asp Leu Pro Leu Thr Leu Ala Ile Ala Arg Glu Val Gly Asn Leu Leu
            180                 185                 190 ctg acg gac agt ttg ctc gct gaa act aac cgt cat tta aat caa ctt         624
Leu Thr Asp Ser Leu Leu Ala Glu Thr Asn Arg His Leu Asn Gln Leu
            195                 200                 205 aat gcc ctg tta gaa agt atg gat gat ggc gtg att agc tgg gac gag         672
Asn Ala Leu Leu Glu Ser Met Asp Asp Gly Val Ile Ser Trp Asp Glu
210                 215                 220 cag ggt aat ttg caa ttt att aat gcc cag gcg gcg cgg gtc ttg cgc         720
Gln Gly Asn Leu Gln Phe Ile Asn Ala Gln Ala Ala Arg Val Leu Arg
225                 230                 235                 240 ctt gac gcg acg gca agt cag gga cgg gca atc act gaa ctc tta acg         768
Leu Asp Ala Thr Ala Ser Gln Gly Arg Ala Ile Thr Glu Leu Leu Thr
                245                 250                 255 tta ccc gcc gta ttg caa caa gca ata aaa cag gca cat ccg ctc aaa         816
Leu Pro Ala Val Leu Gln Gln Ala Ile Lys Gln Ala His Pro Leu Lys
            260                 265                 270 cac gta gaa gca acc ttt gaa agc cag cac cag ttt att gat gcg gtg         864
His Val Glu Ala Thr Phe Glu Ser Gln His Gln Phe Ile Asp Ala Val
            275                 280                 285 ata acc ctt aaa ccg ata ata gaa acg cag gga acc agc ttt att ttg         912
Ile Thr Leu Lys Pro Ile Ile Glu Thr Gln Gly Thr Ser Phe Ile Leu
290                 295                 300 ttg ctc cat cct gtg gaa cag atg cgg cag ttg atg acc agt caa tta         960
Leu Leu His Pro Val Glu Gln Met Arg Gln Leu Met Thr Ser Gln Leu
305                 310                 315                 320 gga aaa gtc agc cat acc ttc gct cat atg cca cag gac gat ccg caa        1008
Gly Lys Val Ser His Thr Phe Ala His Met Pro Gln Asp Asp Pro Gln
                325                 330                 335
```

-continued

| | |
|---|---|
| acc cgc cgc ttg att cat ttt ggt cgc cag gcg gcg cgc agt agc ttt<br>Thr Arg Arg Leu Ile His Phe Gly Arg Gln Ala Ala Arg Ser Ser Phe<br>340 345 350 | 1056 |
| cct gtc ctg ctt tgt gga gaa gag ggc gtg ggc aag gca ctg cta agt<br>Pro Val Leu Leu Cys Gly Glu Glu Gly Val Gly Lys Ala Leu Leu Ser<br>355 360 365 | 1104 |
| cag gca att cat aat gaa agc gag cgt gct gca ggt cct tat atc gcc<br>Gln Ala Ile His Asn Glu Ser Glu Arg Ala Ala Gly Pro Tyr Ile Ala<br>370 375 380 | 1152 |
| gtc aat tgt gag tta tat ggt gat gct gcg ctg gcg gaa gaa ttt att<br>Val Asn Cys Glu Leu Tyr Gly Asp Ala Ala Leu Ala Glu Glu Phe Ile<br>385 390 395 400 | 1200 |
| ggt ggc gat cgc acg gac aat gaa aat ggc cgt ctg agt cgg ctg gaa<br>Gly Gly Asp Arg Thr Asp Asn Glu Asn Gly Arg Leu Ser Arg Leu Glu<br>405 410 415 | 1248 |
| ctg gca cac ggc ggc acg ctg ttt ctt gaa aag att gaa tat ctg gcg<br>Leu Ala His Gly Gly Thr Leu Phe Leu Glu Lys Ile Glu Tyr Leu Ala<br>420 425 430 | 1296 |
| gtg gag tta cag tct gct ttg ctt cag gtt atc aag cag ggg gtt atc<br>Val Glu Leu Gln Ser Ala Leu Leu Gln Val Ile Lys Gln Gly Val Ile<br>435 440 445 | 1344 |
| acg cga ctg gat gcg cgg cgt tta ata cca att gat gtc aaa gtg att<br>Thr Arg Leu Asp Ala Arg Arg Leu Ile Pro Ile Asp Val Lys Val Ile<br>450 455 460 | 1392 |
| gca aca acg acc gcg gac ctc gca atg ctg gtg gaa caa aat cgt ttt<br>Ala Thr Thr Thr Ala Asp Leu Ala Met Leu Val Glu Gln Asn Arg Phe<br>465 470 475 480 | 1440 |
| agt cgc cag ctg tat tac gcg ctg cat gca ttt gaa att acc atc ccg<br>Ser Arg Gln Leu Tyr Tyr Ala Leu His Ala Phe Glu Ile Thr Ile Pro<br>485 490 495 | 1488 |
| cct ctg cgt atg cgg cgt ggc agc att ccg gcg ctg gtg aat aac aaa<br>Pro Leu Arg Met Arg Arg Gly Ser Ile Pro Ala Leu Val Asn Asn Lys<br>500 505 510 | 1536 |
| tta cgc agt ctt gaa aaa cgc ttc tct acg cgg ctg aaa att gat gac<br>Leu Arg Ser Leu Glu Lys Arg Phe Ser Thr Arg Leu Lys Ile Asp Asp<br>515 520 525 | 1584 |
| gat gcc ctc gct cgc ctg gtt tct tgt gca tgg cca ggc aac gat ttt<br>Asp Ala Leu Ala Arg Leu Val Ser Cys Ala Trp Pro Gly Asn Asp Phe<br>530 535 540 | 1632 |
| gaa ctt tac agc gtc atc gag aat ctt gct ctg agt agt gat aac ggg<br>Glu Leu Tyr Ser Val Ile Glu Asn Leu Ala Leu Ser Ser Asp Asn Gly<br>545 550 555 560 | 1680 |
| cgc att cgc gtc agt gat ttg ccg gaa cat ctg ttt acc gag cag gcg<br>Arg Ile Arg Val Ser Asp Leu Pro Glu His Leu Phe Thr Glu Gln Ala<br>565 570 575 | 1728 |
| aca gat gat gtc agc gcc acc cgc ctt tcc acc agt ctg tca ttt gcg<br>Thr Asp Asp Val Ser Ala Thr Arg Leu Ser Thr Ser Leu Ser Phe Ala<br>580 585 590 | 1776 |
| gaa gtt gaa aaa gag gca att att aac gca gcc cag gtc aca ggc ggt<br>Glu Val Glu Lys Glu Ala Ile Ile Asn Ala Ala Gln Val Thr Gly Gly<br>595 600 605 | 1824 |
| cgc att cag gaa atg tcg gct tta ctt ggg atc ggc cgc act acg ctg<br>Arg Ile Gln Glu Met Ser Ala Leu Leu Gly Ile Gly Arg Thr Thr Leu<br>610 615 620 | 1872 |
| tgg cgg aaa atg aag caa cat ggc att gat gca ggg cag ttt aag cgc<br>Trp Arg Lys Met Lys Gln His Gly Ile Asp Ala Gly Gln Phe Lys Arg<br>625 630 635 640 | 1920 |
| cgg gta tga<br>Arg Val | 1929 |

<210> SEQ ID NO 32
<211> LENGTH: 642
<212> TYPE: PRT
<213> ORGANISM: Escherichia coli

<400> SEQUENCE: 32

```
Met Arg Asp Met Ser Gly Ala Phe Asn Asn Asp Gly Arg Gly Ile Ser
1               5                   10                  15

Pro Leu Ile Ala Thr Ser Trp Glu Arg Cys Asn Lys Leu Met Lys Arg
            20                  25                  30

Glu Thr Trp Asn Val Pro His Gln Ala Gln Gly Val Thr Phe Ala Ser
        35                  40                  45

Ile Tyr Arg Arg Lys Lys Ala Met Leu Thr Leu Gly Gln Ala Ala Leu
    50                  55                  60

Glu Asp Ala Trp Glu Tyr Met Ala Pro Arg Glu Cys Ala Leu Phe Ile
65                  70                  75                  80

Leu Asp Glu Thr Ala Cys Ile Leu Ser Arg Asn Gly Asp Pro Gln Thr
                85                  90                  95

Leu Gln Gln Leu Ser Ala Leu Gly Phe Asn Asp Gly Thr Tyr Cys Ala
            100                 105                 110

Glu Gly Ile Ile Gly Thr Cys Ala Leu Ser Leu Ala Ala Ile Ser Gly
        115                 120                 125

Gln Ala Val Lys Thr Met Ala Asp Gln His Phe Lys Gln Val Leu Trp
    130                 135                 140

Asn Trp Ala Phe Cys Ala Thr Pro Leu Phe Asp Ser Lys Gly Arg Leu
145                 150                 155                 160

Thr Gly Thr Ile Ala Leu Ala Cys Pro Val Glu Gln Thr Thr Ala Ala
                165                 170                 175

Asp Leu Pro Leu Thr Leu Ala Ile Ala Arg Glu Val Gly Asn Leu Leu
            180                 185                 190

Leu Thr Asp Ser Leu Leu Ala Glu Thr Asn Arg His Leu Asn Gln Leu
        195                 200                 205

Asn Ala Leu Leu Glu Ser Met Asp Asp Gly Val Ile Ser Trp Asp Glu
    210                 215                 220

Gln Gly Asn Leu Gln Phe Ile Asn Ala Gln Ala Arg Val Leu Arg
225                 230                 235                 240

Leu Asp Ala Thr Ala Ser Gln Gly Arg Ala Ile Thr Glu Leu Leu Thr
                245                 250                 255

Leu Pro Ala Val Leu Gln Gln Ala Ile Lys Gln Ala His Pro Leu Lys
            260                 265                 270

His Val Glu Ala Thr Phe Glu Ser Gln His Gln Phe Ile Asp Ala Val
        275                 280                 285

Ile Thr Leu Lys Pro Ile Ile Glu Thr Gln Gly Thr Ser Phe Ile Leu
    290                 295                 300

Leu Leu His Pro Val Glu Gln Met Arg Gln Leu Met Thr Ser Gln Leu
305                 310                 315                 320

Gly Lys Val Ser His Thr Phe Ala His Met Pro Gln Asp Asp Pro Gln
                325                 330                 335

Thr Arg Arg Leu Ile His Phe Gly Arg Gln Ala Ala Arg Ser Ser Phe
            340                 345                 350

Pro Val Leu Leu Cys Gly Glu Glu Gly Val Gly Lys Ala Leu Leu Ser
        355                 360                 365

Gln Ala Ile His Asn Glu Ser Glu Arg Ala Ala Gly Pro Tyr Ile Ala
    370                 375                 380
```

```
Val Asn Cys Glu Leu Tyr Gly Asp Ala Ala Leu Ala Glu Glu Phe Ile
385                 390                 395                 400

Gly Gly Asp Arg Thr Asp Asn Glu Asn Gly Arg Leu Ser Arg Leu Glu
            405                 410                 415

Leu Ala His Gly Gly Thr Leu Phe Leu Glu Lys Ile Gly Tyr Leu Ala
            420                 425                 430

Val Glu Leu Gln Ser Ala Leu Leu Gln Val Ile Lys Gln Gly Val Ile
            435                 440                 445

Thr Arg Leu Asp Ala Arg Arg Leu Ile Pro Ile Asp Val Lys Val Ile
            450                 455                 460

Ala Thr Thr Thr Ala Asp Leu Ala Met Leu Val Glu Gln Asn Arg Phe
465                 470                 475                 480

Ser Arg Gln Leu Tyr Tyr Ala Leu His Ala Phe Glu Ile Thr Ile Pro
            485                 490                 495

Pro Leu Arg Met Arg Arg Gly Ser Ile Pro Ala Leu Val Asn Asn Lys
            500                 505                 510

Leu Arg Ser Leu Glu Lys Arg Phe Ser Thr Arg Leu Lys Ile Asp Asp
            515                 520                 525

Asp Ala Leu Ala Arg Leu Val Ser Cys Ala Trp Pro Gly Asn Asp Phe
530                 535                 540

Glu Leu Tyr Ser Val Ile Glu Asn Leu Ala Leu Ser Ser Asp Asn Gly
545                 550                 555                 560

Arg Ile Arg Val Ser Asp Leu Pro Glu His Leu Phe Thr Glu Gln Ala
            565                 570                 575

Thr Asp Asp Val Ser Ala Thr Arg Leu Ser Thr Ser Leu Ser Phe Ala
            580                 585                 590

Glu Val Glu Lys Glu Ala Ile Ile Asn Ala Ala Gln Val Thr Gly Gly
            595                 600                 605

Arg Ile Gln Glu Met Ser Ala Leu Leu Gly Ile Gly Arg Thr Thr Leu
            610                 615                 620

Trp Arg Lys Met Lys Gln His Gly Ile Asp Ala Gly Gln Phe Lys Arg
625                 630                 635                 640

Arg Val

<210> SEQ ID NO 33
<211> LENGTH: 735
<212> TYPE: DNA
<213> ORGANISM: Escherichia coli
<220> FEATURE:
<221> NAME/KEY: CDS
<222> LOCATION: (1)..(735)
<223> OTHER INFORMATION: fsa coding region

<400> SEQUENCE: 33 gtg cgt caa ctg ttc aga gag ttt tcc cgt gat agt cta cat tca gac      48
Val Arg Gln Leu Phe Arg Glu Phe Ser Arg Asp Ser Leu His Ser Asp
1               5                   10                  15 aaa aag tac att ttg agg atg gtt atg gaa ctg tat ctg gat act tca      96
Lys Lys Tyr Ile Leu Arg Met Val Met Glu Leu Tyr Leu Asp Thr Ser
            20                  25                  30 gac gtt gtt gcg gtg aag gcg ctg tca cgt att ttt ccg ctg gcg ggt     144
Asp Val Val Ala Val Lys Ala Leu Ser Arg Ile Phe Pro Leu Ala Gly
        35                  40                  45 gtg acc act aac cca agc att atc gcc gcg ggt aaa aaa ccg ctg gat     192
Val Thr Thr Asn Pro Ser Ile Ile Ala Ala Gly Lys Lys Pro Leu Asp
    50                  55                  60
```

```
gtt gtg ctt ccg caa ctt cat gaa gcg atg ggc ggt cag ggg cgt ctg      240
Val Val Leu Pro Gln Leu His Glu Ala Met Gly Gly Gln Gly Arg Leu
65                  70                  75                  80 ttt gcc cag gta atg gct acc act gcc gaa ggg atg gtt aat gac gcg      288
Phe Ala Gln Val Met Ala Thr Thr Ala Glu Gly Met Val Asn Asp Ala
                85                  90                  95 ctt aag ctg cgt tct att att gcg gat atc gtg gtg aaa gtt ccg gtg      336
Leu Lys Leu Arg Ser Ile Ile Ala Asp Ile Val Val Lys Val Pro Val
            100                 105                 110 acc gcc gag ggg ctg gca gct att aag atg tta aaa gcg gaa ggg att      384
Thr Ala Glu Gly Leu Ala Ala Ile Lys Met Leu Lys Ala Glu Gly Ile
        115                 120                 125 ccg acg ctg gga acc gcg gta tat ggc gca gca caa ggg ctg ctg tcg      432
Pro Thr Leu Gly Thr Ala Val Tyr Gly Ala Ala Gln Gly Leu Leu Ser
    130                 135                 140 gcg ctg gca ggt gcg gaa tat gtt gcg cct tac gtt aat cgt att gat      480
Ala Leu Ala Gly Ala Glu Tyr Val Ala Pro Tyr Val Asn Arg Ile Asp
145                 150                 155                 160 gct cag ggc ggt agc ggc att cag act gtg acc gac tta cac cag tta      528
Ala Gln Gly Gly Ser Gly Ile Gln Thr Val Thr Asp Leu His Gln Leu
                165                 170                 175 ttg aaa atg cat gcg ccg cag gcg aaa gtg ctg gca gcg agt ttc aaa      576
Leu Lys Met His Ala Pro Gln Ala Lys Val Leu Ala Ala Ser Phe Lys
            180                 185                 190 acc ccg cgt cag gcg ctg gac tgc tta ctg gca gga tgt gaa tca att      624
Thr Pro Arg Gln Ala Leu Asp Cys Leu Leu Ala Gly Cys Glu Ser Ile
        195                 200                 205 act ctg cca ctg gat gtg gca caa cag atg att agc tat ccg gcg gtt      672
Thr Leu Pro Leu Asp Val Ala Gln Gln Met Ile Ser Tyr Pro Ala Val
    210                 215                 220 gat gcc gct gtg gcg aag ttt gag cag gac tgg cag gga gcg ttt ggc      720
Asp Ala Ala Val Ala Lys Phe Glu Gln Asp Trp Gln Gly Ala Phe Gly
225                 230                 235                 240 aga acg tcg att taa                                                  735
Arg Thr Ser Ile <210> SEQ ID NO 34
<211> LENGTH: 244
<212> TYPE: PRT
<213> ORGANISM: Escherichia coli

<400> SEQUENCE: 34

Val Arg Gln Leu Phe Arg Glu Phe Ser Arg Asp Ser Leu His Ser Asp
1               5                   10                  15

Lys Lys Tyr Ile Leu Arg Met Val Met Glu Leu Tyr Leu Asp Thr Ser
            20                  25                  30

Asp Val Val Ala Val Lys Ala Leu Ser Arg Ile Phe Pro Leu Ala Gly
        35                  40                  45

Val Thr Thr Asn Pro Ser Ile Ile Ala Ala Gly Lys Lys Pro Leu Asp
    50                  55                  60

Val Val Leu Pro Gln Leu His Glu Ala Met Gly Gly Gln Gly Arg Leu
65                  70                  75                  80

Phe Ala Gln Val Met Ala Thr Thr Ala Glu Gly Met Val Asn Asp Ala
                85                  90                  95

Leu Lys Leu Arg Ser Ile Ile Ala Asp Ile Val Val Lys Val Pro Val
            100                 105                 110

Thr Ala Glu Gly Leu Ala Ala Ile Lys Met Leu Lys Ala Glu Gly Ile
        115                 120                 125
```

```
Pro Thr Leu Gly Thr Ala Val Tyr Gly Ala Ala Gln Gly Leu Leu Ser
    130                 135                 140

Ala Leu Ala Gly Ala Glu Tyr Val Ala Pro Tyr Val Asn Arg Ile Asp
145                 150                 155                 160

Ala Gln Gly Gly Ser Gly Ile Gln Thr Val Thr Asp Leu His Gln Leu
                165                 170                 175

Leu Lys Met His Ala Pro Gln Ala Lys Val Leu Ala Ala Ser Phe Lys
            180                 185                 190

Thr Pro Arg Gln Ala Leu Asp Cys Leu Leu Ala Gly Cys Glu Ser Ile
        195                 200                 205

Thr Leu Pro Leu Asp Val Ala Gln Gln Met Ile Ser Tyr Pro Ala Val
    210                 215                 220

Asp Ala Ala Val Ala Lys Phe Glu Gln Asp Trp Gln Gly Ala Phe Gly
225                 230                 235                 240

Arg Thr Ser Ile

<210> SEQ ID NO 35
<211> LENGTH: 663
<212> TYPE: DNA
<213> ORGANISM: Escherichia coli
<220> FEATURE:
<221> NAME/KEY: CDS
<222> LOCATION: (1)..(663)
<223> OTHER INFORMATION: talC coding region

<400> SEQUENCE: 35 atg gaa ctg tat ctg gac acc gct aac gtc gca gaa gtc gaa cgt ctg      48
Met Glu Leu Tyr Leu Asp Thr Ala Asn Val Ala Glu Val Glu Arg Leu
1               5                   10                  15 gca cgc ata ttc ccc att gcc ggg gtg aca act aac ccg agc att atc      96
Ala Arg Ile Phe Pro Ile Ala Gly Val Thr Thr Asn Pro Ser Ile Ile
                20                  25                  30 gct gcc agc aag gag tcc ata tgg gaa gtg ctg ccg cgt ctg caa aaa     144
Ala Ala Ser Lys Glu Ser Ile Trp Glu Val Leu Pro Arg Leu Gln Lys
            35                  40                  45 gcg att ggt gat gag ggc att ctg ttt gct cag acc atg agc cgc gac     192
Ala Ile Gly Asp Glu Gly Ile Leu Phe Ala Gln Thr Met Ser Arg Asp
        50                  55                  60 gcg cag ggg atg gtg gaa gaa gcg aag cgc ctg cgc gac gct att ccg     240
Ala Gln Gly Met Val Glu Glu Ala Lys Arg Leu Arg Asp Ala Ile Pro
65                  70                  75                  80 ggt att gtg gtg aaa atc ccg gtg act tcc gaa ggt ctg gca gca att     288
Gly Ile Val Val Lys Ile Pro Val Thr Ser Glu Gly Leu Ala Ala Ile
                85                  90                  95 aaa ata ctg aaa aaa gag ggt att act aca ctt ggc act gct gta tat     336
Lys Ile Leu Lys Lys Glu Gly Ile Thr Thr Leu Gly Thr Ala Val Tyr
            100                 105                 110 agc gcc gca caa ggg tta tta gcc gca ctg gca ggg gca aaa tac gtt     384
Ser Ala Ala Gln Gly Leu Leu Ala Ala Leu Ala Gly Ala Lys Tyr Val
        115                 120                 125 gct ccg tat gtt aac cgc gta gat gcc cag ggc gga gac ggc att cgt     432
Ala Pro Tyr Val Asn Arg Val Asp Ala Gln Gly Gly Asp Gly Ile Arg
    130                 135                 140 acg gtt cag gag ctg caa acg ctg tta gaa atg cac gcg cca gaa agc     480
Thr Val Gln Glu Leu Gln Thr Leu Leu Glu Met His Ala Pro Glu Ser
145                 150                 155                 160 atg gtg ctg gca gcc agc ttt aaa acg ccg cgt cag gcg ctg gac tgt     528
Met Val Leu Ala Ala Ser Phe Lys Thr Pro Arg Gln Ala Leu Asp Cys
                165                 170                 175
```

```
tta ctg gca gga tgt gaa tcc atc acc ctg ccc tta gat gta gcg caa    576
Leu Leu Ala Gly Cys Glu Ser Ile Thr Leu Pro Leu Asp Val Ala Gln
        180                 185                 190 caa atg ctc aac acc cct gcg gta gag tca gct ata gag aag ttc gaa    624
Gln Met Leu Asn Thr Pro Ala Val Glu Ser Ala Ile Glu Lys Phe Glu
    195                 200                 205 cac gac tgg aat gcc gca ttt ggc act act cat ctc taa                663
His Asp Trp Asn Ala Ala Phe Gly Thr Thr His Leu
210                 215                 220
```

<210> SEQ ID NO 36
<211> LENGTH: 220
<212> TYPE: PRT
<213> ORGANISM: Escherichia coli

<400> SEQUENCE: 36

```
Met Glu Leu Tyr Leu Asp Thr Ala Asn Val Ala Glu Val Glu Arg Leu
1               5                   10                  15

Ala Arg Ile Phe Pro Ile Ala Gly Val Thr Thr Asn Pro Ser Ile Ile
            20                  25                  30

Ala Ala Ser Lys Glu Ser Ile Trp Glu Val Leu Pro Arg Leu Gln Lys
        35                  40                  45

Ala Ile Gly Asp Glu Gly Ile Leu Phe Ala Gln Thr Met Ser Arg Asp
    50                  55                  60

Ala Gln Gly Met Val Glu Glu Ala Lys Arg Leu Arg Asp Ala Ile Pro
65                  70                  75                  80

Gly Ile Val Val Lys Ile Pro Val Thr Ser Glu Gly Leu Ala Ala Ile
                85                  90                  95

Lys Ile Leu Lys Lys Glu Gly Ile Thr Thr Leu Gly Thr Ala Val Tyr
            100                 105                 110

Ser Ala Ala Gln Gly Leu Leu Ala Ala Leu Ala Gly Ala Lys Tyr Val
        115                 120                 125

Ala Pro Tyr Val Asn Arg Val Asp Ala Gln Gly Gly Asp Gly Ile Arg
    130                 135                 140

Thr Val Gln Glu Leu Gln Thr Leu Leu Glu Met His Ala Pro Glu Ser
145                 150                 155                 160

Met Val Leu Ala Ala Ser Phe Lys Thr Pro Arg Gln Ala Leu Asp Cys
                165                 170                 175

Leu Leu Ala Gly Cys Glu Ser Ile Thr Leu Pro Leu Asp Val Ala Gln
            180                 185                 190

Gln Met Leu Asn Thr Pro Ala Val Glu Ser Ala Ile Glu Lys Phe Glu
        195                 200                 205

His Asp Trp Asn Ala Ala Phe Gly Thr Thr His Leu
    210                 215                 220
```

<210> SEQ ID NO 37
<211> LENGTH: 1530
<212> TYPE: DNA
<213> ORGANISM: Corynebacterium glutamicum
<220> FEATURE:
<221> NAME/KEY: CDS
<222> LOCATION: (1)..(1530)
<223> OTHER INFORMATION: glpK coding region

<400> SEQUENCE: 37

```
atg aga atc tca aag gcc aat gcg tat gtt gca gcg att gac caa ggc    48
Met Arg Ile Ser Lys Ala Asn Ala Tyr Val Ala Ala Ile Asp Gln Gly
1               5                   10                  15 acc act tcc act cgg tgc atc ttc att gat gcc caa gga aaa gtg gtg    96
```

```
                Thr Thr Ser Thr Arg Cys Ile Phe Ile Asp Ala Gln Gly Lys Val Val
                        20                  25                  30 tct tct gct tcc aag gag cac cgc caa atc ttc cca caa cag ggc tgg        144
Ser Ser Ala Ser Lys Glu His Arg Gln Ile Phe Pro Gln Gln Gly Trp
            35                  40                  45 gta gag cac gat cct gaa gaa att tgg gac aac atc cga tct gtc gtc        192
Val Glu His Asp Pro Glu Glu Ile Trp Asp Asn Ile Arg Ser Val Val
        50                  55                  60 agc cag gcg atg gtc tcc att gac atc acc cca cac gag gtt gca tcg        240
Ser Gln Ala Met Val Ser Ile Asp Ile Thr Pro His Glu Val Ala Ser
65                  70                  75                  80 ctg gga gtc acc aac cag cgc gaa acc acc gtg gtg tgg gac aag cac        288
Leu Gly Val Thr Asn Gln Arg Glu Thr Thr Val Val Trp Asp Lys His
                85                  90                  95 acc ggc gaa cct gtc tac aac gca atc gtg tgg caa gac acc cgc acc        336
Thr Gly Glu Pro Val Tyr Asn Ala Ile Val Trp Gln Asp Thr Arg Thr
            100                 105                 110 tct gac att tgc cta gag atc gcg ggc gaa gaa ggc cag gaa aag tgg        384
Ser Asp Ile Cys Leu Glu Ile Ala Gly Glu Glu Gly Gln Glu Lys Trp
        115                 120                 125 ctt gac cgc acc ggc ctg ctg atc aac tcc tac cca tcg ggg ccc aaa        432
Leu Asp Arg Thr Gly Leu Leu Ile Asn Ser Tyr Pro Ser Gly Pro Lys
130                 135                 140 atc aag tgg att ctc gac aac gtt gag gga gct cgc gaa cgc gcc gaa        480
Ile Lys Trp Ile Leu Asp Asn Val Glu Gly Ala Arg Glu Arg Ala Glu
145                 150                 155                 160 aag ggc gac ctt ttg ttt ggc acc atg gat acc tgg gtg ctg tgg aac        528
Lys Gly Asp Leu Leu Phe Gly Thr Met Asp Thr Trp Val Leu Trp Asn
                165                 170                 175 ctg acc ggc ggt gtc cgc ggc gac gac ggt gat gat gcc atc cac gtc        576
Leu Thr Gly Gly Val Arg Gly Asp Asp Gly Asp Asp Ala Ile His Val
            180                 185                 190 acc gat gtc acc aac gca tcc cgc aca cta ttg atg gat ctc cgc acg        624
Thr Asp Val Thr Asn Ala Ser Arg Thr Leu Leu Met Asp Leu Arg Thr
        195                 200                 205 caa cag tgg gat cca gaa cta tgc gaa gcc cta gac att ccg atg tcc        672
Gln Gln Trp Asp Pro Glu Leu Cys Glu Ala Leu Asp Ile Pro Met Ser
210                 215                 220 atg ctc cct gag att cgt ccc tcc gtc gga gaa ttc cgc tcc gtg cgc        720
Met Leu Pro Glu Ile Arg Pro Ser Val Gly Glu Phe Arg Ser Val Arg
225                 230                 235                 240 cac cgc gga acc cta gcc gac gtc ccg att act ggc gtg ctc ggc gac        768
His Arg Gly Thr Leu Ala Asp Val Pro Ile Thr Gly Val Leu Gly Asp
                245                 250                 255 cag caa gcg gcc ctt ttt ggt cag ggc gga ttc cac gaa ggt gct gct        816
Gln Gln Ala Ala Leu Phe Gly Gln Gly Gly Phe His Glu Gly Ala Ala
            260                 265                 270 aaa aat acc tac ggc acc ggc ctc ttc ctg ctg atg aac acc ggc acc        864
Lys Asn Thr Tyr Gly Thr Gly Leu Phe Leu Leu Met Asn Thr Gly Thr
        275                 280                 285 tcg ttg aag att tcc gag cac ggc ctg ctg tcc acc atc gcc tat caa        912
Ser Leu Lys Ile Ser Glu His Gly Leu Leu Ser Thr Ile Ala Tyr Gln
290                 295                 300 cgg gaa gga tcc gct ccg gtc tac gcg ctg gaa ggt tcc gta tcc atg        960
Arg Glu Gly Ser Ala Pro Val Tyr Ala Leu Glu Gly Ser Val Ser Met
305                 310                 315                 320 ggc ggt tcc ttg gtg cag tgg ctg cgc gac aac cta cag cta atc ccc       1008
Gly Gly Ser Leu Val Gln Trp Leu Arg Asp Asn Leu Gln Leu Ile Pro
                325                 330                 335
```

-continued

```
aac gca cca gcg att gaa aac ctc gcc cga gaa gtc gaa gac aac ggt    1056
Asn Ala Pro Ala Ile Glu Asn Leu Ala Arg Glu Val Glu Asp Asn Gly
        340                 345                 350 ggc gtt cat gtt gtc cca gca ttc acc gga ctg ttc gca cca cgt tgg    1104
Gly Val His Val Val Pro Ala Phe Thr Gly Leu Phe Ala Pro Arg Trp
    355                 360                 365 cgc ccc gat gct cgt ggc gtc att aca ggc ctc acc cgt ttt gcc aac    1152
Arg Pro Asp Ala Arg Gly Val Ile Thr Gly Leu Thr Arg Phe Ala Asn
370                 375                 380 cgc aaa cac atc gcc cgc gca gtc ctt gaa gcc aac gcc ttc caa acc    1200
Arg Lys His Ile Ala Arg Ala Val Leu Glu Ala Asn Ala Phe Gln Thr
385                 390                 395                 400 cgc gaa gtt gtg gac gcc atg gcc aaa gac gca ggc aaa gcc ctc gaa    1248
Arg Glu Val Val Asp Ala Met Ala Lys Asp Ala Gly Lys Ala Leu Glu
                405                 410                 415 tcc ctc cgc gtc gac ggt gcg atg gtg gaa aat gac ctc ctc atg caa    1296
Ser Leu Arg Val Asp Gly Ala Met Val Glu Asn Asp Leu Leu Met Gln
            420                 425                 430 atg caa gcc gac ttc ctc ggc atc gac gtc caa cgt ctc gag gac gta    1344
Met Gln Ala Asp Phe Leu Gly Ile Asp Val Gln Arg Leu Glu Asp Val
        435                 440                 445 gaa acc acc gcc gtc ggc gtc gca ttc gct gca ggt ctc ggc tct gga    1392
Glu Thr Thr Ala Val Gly Val Ala Phe Ala Ala Gly Leu Gly Ser Gly
    450                 455                 460 ttc ttc aaa aca act gac gag atc gaa aaa ctt att gca gtg aag aaa    1440
Phe Phe Lys Thr Thr Asp Glu Ile Glu Lys Leu Ile Ala Val Lys Lys
465                 470                 475                 480 gtc tgg aac cct gac atg agc gaa gaa gag cgc gaa cgt cgc tat gcc    1488
Val Trp Asn Pro Asp Met Ser Glu Glu Glu Arg Glu Arg Arg Tyr Ala
                485                 490                 495 gaa tgg aat agg gca gtg gag cat tct tat gac cag gcc tag            1530
Glu Trp Asn Arg Ala Val Glu His Ser Tyr Asp Gln Ala
            500                 505

<210> SEQ ID NO 38
<211> LENGTH: 509
<212> TYPE: PRT
<213> ORGANISM: Corynebacterium glutamicum

<400> SEQUENCE: 38

Met Arg Ile Ser Lys Ala Asn Ala Tyr Val Ala Ala Ile Asp Gln Gly
1               5                   10                  15

Thr Thr Ser Thr Arg Cys Ile Phe Ile Asp Ala Gln Gly Lys Val Val
                20                  25                  30

Ser Ser Ala Ser Lys Glu His Arg Gln Ile Phe Pro Gln Gln Gly Trp
        35                  40                  45

Val Glu His Asp Pro Glu Glu Ile Trp Asp Asn Ile Arg Ser Val Val
    50                  55                  60

Ser Gln Ala Met Val Ser Ile Asp Ile Thr Pro His Glu Val Ala Ser
65                  70                  75                  80

Leu Gly Val Thr Asn Gln Arg Glu Thr Thr Val Val Trp Asp Lys His
                85                  90                  95

Thr Gly Glu Pro Val Tyr Asn Ala Ile Val Trp Gln Asp Thr Arg Thr
            100                 105                 110

Ser Asp Ile Cys Leu Glu Ile Ala Gly Glu Glu Gly Gln Glu Lys Trp
        115                 120                 125

Leu Asp Arg Thr Gly Leu Leu Ile Asn Ser Tyr Pro Ser Gly Pro Lys
    130                 135                 140
```

```
Ile Lys Trp Ile Leu Asp Asn Val Glu Gly Ala Arg Glu Arg Ala Glu
145                 150                 155                 160

Lys Gly Asp Leu Leu Phe Gly Thr Met Asp Thr Trp Val Leu Trp Asn
            165                 170                 175

Leu Thr Gly Gly Val Arg Gly Asp Asp Gly Asp Asp Ala Ile His Val
        180                 185                 190

Thr Asp Val Thr Asn Ala Ser Arg Thr Leu Leu Met Asp Leu Arg Thr
    195                 200                 205

Gln Gln Trp Asp Pro Glu Leu Cys Glu Ala Leu Asp Ile Pro Met Ser
210                 215                 220

Met Leu Pro Glu Ile Arg Pro Ser Val Gly Glu Phe Arg Ser Val Arg
225                 230                 235                 240

His Arg Gly Thr Leu Ala Asp Val Pro Ile Thr Gly Val Leu Gly Asp
            245                 250                 255

Gln Gln Ala Ala Leu Phe Gly Gln Gly Phe His Glu Gly Ala Ala
        260                 265                 270

Lys Asn Thr Tyr Gly Thr Gly Leu Phe Leu Leu Met Asn Thr Gly Thr
    275                 280                 285

Ser Leu Lys Ile Ser Glu His Gly Leu Leu Ser Thr Ile Ala Tyr Gln
290                 295                 300

Arg Glu Gly Ser Ala Pro Val Tyr Ala Leu Glu Gly Ser Val Ser Met
305                 310                 315                 320

Gly Gly Ser Leu Val Gln Trp Leu Arg Asp Asn Leu Gln Leu Ile Pro
            325                 330                 335

Asn Ala Pro Ala Ile Glu Asn Leu Ala Arg Glu Val Glu Asp Asn Gly
        340                 345                 350

Gly Val His Val Val Pro Ala Phe Thr Gly Leu Phe Ala Pro Arg Trp
    355                 360                 365

Arg Pro Asp Ala Arg Gly Val Ile Thr Gly Leu Thr Arg Phe Ala Asn
370                 375                 380

Arg Lys His Ile Ala Arg Ala Val Leu Glu Ala Asn Ala Phe Gln Thr
385                 390                 395                 400

Arg Glu Val Val Asp Ala Met Ala Lys Asp Ala Gly Lys Ala Leu Glu
            405                 410                 415

Ser Leu Arg Val Asp Gly Ala Met Val Glu Asn Asp Leu Leu Met Gln
        420                 425                 430

Met Gln Ala Asp Phe Leu Gly Ile Asp Val Gln Arg Leu Glu Asp Val
    435                 440                 445

Glu Thr Thr Ala Val Gly Val Ala Phe Ala Gly Leu Gly Ser Gly
450                 455                 460

Phe Phe Lys Thr Thr Asp Glu Ile Glu Lys Leu Ile Ala Val Lys Lys
465                 470                 475                 480

Val Trp Asn Pro Asp Met Ser Glu Glu Glu Arg Arg Tyr Ala
            485                 490                 495

Glu Trp Asn Arg Ala Val Glu His Ser Tyr Asp Gln Ala
                500                 505

<210> SEQ ID NO 39
<211> LENGTH: 1725
<212> TYPE: DNA
<213> ORGANISM: Corynebacterium glutamicum
<220> FEATURE:
<221> NAME/KEY: CDS
<222> LOCATION: (1)..(1725)
<223> OTHER INFORMATION: glpD coding region
```

-continued

<400> SEQUENCE: 39

| | | | | | | | | | | | | | | | | |
|---|---|---|---|---|---|---|---|---|---|---|---|---|---|---|---|---|
| atg | tgg | gtt | ggc | ggt | ttt | cct | att | agg | ctc | act | ttt | atg | acg | agc | gca | 48 |
| Met | Trp | Val | Gly | Gly | Phe | Pro | Ile | Arg | Leu | Thr | Phe | Met | Thr | Ser | Ala | |
| 1 | | | | 5 | | | | | 10 | | | | | 15 | | |
| cac | ttt | gaa | tcc | cgc | cgg | att | ggc | cct | ccg | ctt | cgc | gat | aat | tat | gac | 96 |
| His | Phe | Glu | Ser | Arg | Arg | Ile | Gly | Pro | Pro | Leu | Arg | Asp | Asn | Tyr | Asp | |
| | | | 20 | | | | | 25 | | | | | 30 | | | |
| gtc | att | gtg | att | ggc | ggt | ggt | atc | tca | ggt | gta | cag | att | gcg | cga | cat | 144 |
| Val | Ile | Val | Ile | Gly | Gly | Gly | Ile | Ser | Gly | Val | Gln | Ile | Ala | Arg | His | |
| | 35 | | | | | 40 | | | | | 45 | | | | | |
| gct | caa | ggc | cgc | ggt | tta | cgc | act | gtg | atg | ttt | gag | gcc | aga | gat | tat | 192 |
| Ala | Gln | Gly | Arg | Gly | Leu | Arg | Thr | Val | Met | Phe | Glu | Ala | Arg | Asp | Tyr | |
| 50 | | | | | 55 | | | | | 60 | | | | | | |
| tct | tct | gga | aca | tca | tcg | aca | acc | tcc | aag | atg | att | cat | ggt | ggt | ttg | 240 |
| Ser | Ser | Gly | Thr | Ser | Ser | Thr | Thr | Ser | Lys | Met | Ile | His | Gly | Gly | Leu | |
| 65 | | | | | 70 | | | | | 75 | | | | | 80 | |
| cgc | tat | ttg | gag | cag | tac | gat | ttc | ggc | gtg | gtc | cag | gaa | gcc | gtg | aag | 288 |
| Arg | Tyr | Leu | Glu | Gln | Tyr | Asp | Phe | Gly | Val | Val | Gln | Glu | Ala | Val | Lys | |
| | | | | 85 | | | | | 90 | | | | | 95 | | |
| gaa | cgc | cgg | tac | cta | ggt | atc | gcc | gct | ccg | cat | ttg | gtg | gct | cca | cgc | 336 |
| Glu | Arg | Arg | Tyr | Leu | Gly | Ile | Ala | Ala | Pro | His | Leu | Val | Ala | Pro | Arg | |
| | | | 100 | | | | | 105 | | | | | 110 | | | |
| agt | ttc | atg | ctc | acg | gcg | ttt | gat | tgg | tca | gag | ccg | aaa | gcc | cct | atg | 384 |
| Ser | Phe | Met | Leu | Thr | Ala | Phe | Asp | Trp | Ser | Glu | Pro | Lys | Ala | Pro | Met | |
| | | 115 | | | | | 120 | | | | | 125 | | | | |
| ttg | ggt | gct | ggt | gtg | gcg | ttg | tat | gaa | acg | atg | gcg | tgg | cag | cgt | aac | 432 |
| Leu | Gly | Ala | Gly | Val | Ala | Leu | Tyr | Glu | Thr | Met | Ala | Trp | Gln | Arg | Asn | |
| | 130 | | | | | 135 | | | | | 140 | | | | | |
| cag | ggg | caa | tcg | aag | gaa | aac | cac | tcg | ccg | cgt | ttc | cgg | tgg | att | cct | 480 |
| Gln | Gly | Gln | Ser | Lys | Glu | Asn | His | Ser | Pro | Arg | Phe | Arg | Trp | Ile | Pro | |
| 145 | | | | | 150 | | | | | 155 | | | | | 160 | |
| aaa | aat | gca | ctg | ctc | aag | gaa | gtc | ccg | tgg | ctt | gac | ccg | gag | ggc | ttg | 528 |
| Lys | Asn | Ala | Leu | Leu | Lys | Glu | Val | Pro | Trp | Leu | Asp | Pro | Glu | Gly | Leu | |
| | | | | 165 | | | | | 170 | | | | | 175 | | |
| aag | gga | gcg | tgg | cgc | cac | gat | gat | acg | ttg | aat | ctc | cat | gca | gaa | cga | 576 |
| Lys | Gly | Ala | Trp | Arg | His | Asp | Asp | Thr | Leu | Asn | Leu | His | Ala | Glu | Arg | |
| | | | 180 | | | | | 185 | | | | | 190 | | | |
| ctc | ctc | ctc | gcg | gtg | att | aaa | gct | ttt | gcg | gca | gat | ggc | gga | acg | gcg | 624 |
| Leu | Leu | Leu | Ala | Val | Ile | Lys | Ala | Phe | Ala | Ala | Asp | Gly | Gly | Thr | Ala | |
| | | 195 | | | | | 200 | | | | | 205 | | | | |
| atc | aac | cac | gcc | aaa | gtc | act | cgc | att | ctc | cgg | aac | gtg | gaa | gaa | ggc | 672 |
| Ile | Asn | His | Ala | Lys | Val | Thr | Arg | Ile | Leu | Arg | Asn | Val | Glu | Glu | Gly | |
| | 210 | | | | | 215 | | | | | 220 | | | | | |
| cgc | gtc | aag | ggt | gta | gaa | gtg | act | gat | cag | gtc | acc | aac | acc | acg | cat | 720 |
| Arg | Val | Lys | Gly | Val | Glu | Val | Thr | Asp | Gln | Val | Thr | Asn | Thr | Thr | His | |
| 225 | | | | | 230 | | | | | 235 | | | | | 240 | |
| gag | gtg | aat | gcc | cct | gtg | gtg | atc | aac | gct | gcg | ggt | ccg | tgg | gtt | gcg | 768 |
| Glu | Val | Asn | Ala | Pro | Val | Val | Ile | Asn | Ala | Ala | Gly | Pro | Trp | Val | Ala | |
| | | | | 245 | | | | | 250 | | | | | 255 | | |
| cag | gcg | ttg | ggt | gat | ttg | gcg | gag | gta | acc | aag | ttg | aag | gtg | cgc | caa | 816 |
| Gln | Ala | Leu | Gly | Asp | Leu | Ala | Glu | Val | Thr | Lys | Leu | Lys | Val | Arg | Gln | |
| | | | 260 | | | | | 265 | | | | | 270 | | | |
| tcc | aag | gga | gtg | cat | ttg | ctc | act | ggt | gat | ttg | ggc | agc | cag | agt | ggc | 864 |
| Ser | Lys | Gly | Val | His | Leu | Leu | Thr | Gly | Asp | Leu | Gly | Ser | Gln | Ser | Gly | |
| | | 275 | | | | | 280 | | | | | 285 | | | | |
| gtg | ttt | gtg | cgt | ggc | aaa | aac | ggc | aag | cat | gtg | atc | gtg | aat | ccg | tgg | 912 |
| Val | Phe | Val | Arg | Gly | Lys | Asn | Gly | Lys | His | Val | Ile | Val | Asn | Pro | Trp | |
| | 290 | | | | | 295 | | | | | 300 | | | | | |
| atg | ggg | cgc | acc | ctt | att | ggt | cca | acc | gac | acc | atg | att | gac | ggt | gac | 960 |

```
Met Gly Arg Thr Leu Ile Gly Pro Thr Asp Thr Met Ile Asp Gly Asp
305                 310                 315                 320 gct gat gat gcg gct gca gat gaa agc gat atc gat ttg ctg ctt gag    1008
Ala Asp Asp Ala Ala Ala Asp Glu Ser Asp Ile Asp Leu Leu Leu Glu
                    325                 330                 335 acc atc gat tcg gta cgc gct aca ccg ctt gat cgc aaa gag atc atc    1056
Thr Ile Asp Ser Val Arg Ala Thr Pro Leu Asp Arg Lys Glu Ile Ile
                340                 345                 350 tcc acg ctg gtg ggt gtg cgc ccg ctt gtt gat gac ggc acc gac acc    1104
Ser Thr Leu Val Gly Val Arg Pro Leu Val Asp Asp Gly Thr Asp Thr
            355                 360                 365 tac acg tcc tct cgc cgt ttc gat att tcc gat cac gcc aac gtc ggc    1152
Tyr Thr Ser Ser Arg Arg Phe Asp Ile Ser Asp His Ala Asn Val Gly
        370                 375                 380 att gat ggt ttg gtg tct gtc tct ggc ggc aag tgg acc act tcg cgc    1200
Ile Asp Gly Leu Val Ser Val Ser Gly Gly Lys Trp Thr Thr Ser Arg
385                 390                 395                 400 gtg atg ggg tac aag gtg att gag cat gtg gtg gag cac caa gct gcg    1248
Val Met Gly Tyr Lys Val Ile Glu His Val Val Glu His Gln Ala Ala
                    405                 410                 415 gtg tta cct ccg ctg cgc cac ttt gac tcc agg cag atg ccg ttg agt    1296
Val Leu Pro Pro Leu Arg His Phe Asp Ser Arg Gln Met Pro Leu Ser
                420                 425                 430 act tct ttt ggc gcg tat gag tcc gtg gct gat tcc ttt gag tca gcg    1344
Thr Ser Phe Gly Ala Tyr Glu Ser Val Ala Asp Ser Phe Glu Ser Ala
            435                 440                 445 ctt cgc agc cac ccc gag ctg gat gtg gat gat gaa atc cgc gtg cat    1392
Leu Arg Ser His Pro Glu Leu Asp Val Asp Asp Glu Ile Arg Val His
        450                 455                 460 ctg gcc aga ctg tat gga act gag cat gaa aaa gtg ctg gat ctc gtc    1440
Leu Ala Arg Leu Tyr Gly Thr Glu His Glu Lys Val Leu Asp Leu Val
465                 470                 475                 480 gca aag caa ccc gac ctg ggg cgc cga ctt gac cca gac aac ctt gat    1488
Ala Lys Gln Pro Asp Leu Gly Arg Arg Leu Asp Pro Asp Asn Leu Asp
                    485                 490                 495 atc gcg gcg cag gcc gtt ttt gct gtc gcc gag gag gcg gcc gtc gac    1536
Ile Ala Ala Gln Ala Val Phe Ala Val Ala Glu Glu Ala Ala Val Asp
                500                 505                 510 ctg gcg gac gtg ctg gat cgt cgc atc gtg ctc ggc acg ctg ggt tat    1584
Leu Ala Asp Val Leu Asp Arg Arg Ile Val Leu Gly Thr Leu Gly Tyr
            515                 520                 525 gtg caa ccg gct gcc gtg cgt gcg acg gcc gaa gca atg gcg cag gtc    1632
Val Gln Pro Ala Ala Val Arg Ala Thr Ala Glu Ala Met Ala Gln Val
        530                 535                 540 acc ggg tgg tca gct gag ctt atc gac gcc cag tgc cag tcc tac ctc    1680
Thr Gly Trp Ser Ala Glu Leu Ile Asp Ala Gln Cys Gln Ser Tyr Leu
545                 550                 555                 560 gcc aag caa gac aaa atc caa gcc gtg tta aag ccg tac cgc taa        1725
Ala Lys Gln Asp Lys Ile Gln Ala Val Leu Lys Pro Tyr Arg
                    565                 570
```

<210> SEQ ID NO 40
<211> LENGTH: 574
<212> TYPE: PRT
<213> ORGANISM: Corynebacterium glutamicum

<400> SEQUENCE: 40

```
Met Trp Val Gly Gly Phe Pro Ile Arg Leu Thr Phe Met Thr Ser Ala
1               5                   10                  15

His Phe Glu Ser Arg Arg Ile Gly Pro Pro Leu Arg Asp Asn Tyr Asp
```

```
                 20                  25                  30
Val Ile Val Ile Gly Gly Gly Ile Ser Gly Val Gln Ile Ala Arg His
             35                  40                  45
Ala Gln Gly Arg Gly Leu Arg Thr Val Met Phe Glu Ala Arg Asp Tyr
         50                  55                  60
Ser Ser Gly Thr Ser Thr Thr Ser Lys Met Ile His Gly Gly Leu
 65                  70                  75                  80
Arg Tyr Leu Glu Gln Tyr Asp Phe Gly Val Val Gln Glu Ala Val Lys
                 85                  90                  95
Glu Arg Arg Tyr Leu Gly Ile Ala Ala Pro His Leu Val Ala Pro Arg
            100                 105                 110
Ser Phe Met Leu Thr Ala Phe Asp Trp Ser Glu Pro Lys Ala Pro Met
            115                 120                 125
Leu Gly Ala Gly Val Ala Leu Tyr Glu Thr Met Ala Trp Gln Arg Asn
            130                 135                 140
Gln Gly Gln Ser Lys Glu Asn His Ser Pro Arg Phe Arg Trp Ile Pro
145                 150                 155                 160
Lys Asn Ala Leu Leu Lys Glu Val Pro Trp Leu Asp Pro Glu Gly Leu
                165                 170                 175
Lys Gly Ala Trp Arg His Asp Asp Thr Leu Asn Leu His Ala Glu Arg
            180                 185                 190
Leu Leu Leu Ala Val Ile Lys Ala Phe Ala Ala Asp Gly Gly Thr Ala
            195                 200                 205
Ile Asn His Ala Lys Val Thr Arg Ile Leu Arg Asn Val Glu Glu Gly
            210                 215                 220
Arg Val Lys Gly Val Glu Val Thr Asp Gln Val Thr Asn Thr Thr His
225                 230                 235                 240
Glu Val Asn Ala Pro Val Val Ile Asn Ala Ala Gly Pro Trp Val Ala
                245                 250                 255
Gln Ala Leu Gly Asp Leu Ala Glu Val Thr Lys Leu Lys Val Arg Gln
            260                 265                 270
Ser Lys Gly Val His Leu Leu Thr Gly Asp Leu Gly Ser Gln Ser Gly
            275                 280                 285
Val Phe Val Arg Gly Lys Asn Gly Lys His Val Ile Val Asn Pro Trp
            290                 295                 300
Met Gly Arg Thr Leu Ile Gly Pro Thr Asp Thr Met Ile Asp Gly Asp
305                 310                 315                 320
Ala Asp Asp Ala Ala Ala Asp Glu Ser Asp Ile Asp Leu Leu Leu Glu
                325                 330                 335
Thr Ile Asp Ser Val Arg Ala Thr Pro Leu Asp Arg Lys Glu Ile Ile
            340                 345                 350
Ser Thr Leu Val Gly Val Arg Pro Leu Val Asp Gly Thr Asp Thr
            355                 360                 365
Tyr Thr Ser Ser Arg Arg Phe Asp Ile Ser Asp His Ala Asn Val Gly
            370                 375                 380
Ile Asp Gly Leu Val Ser Val Ser Gly Gly Lys Trp Thr Thr Ser Arg
385                 390                 395                 400
Val Met Gly Tyr Lys Val Ile Glu His Val Glu His Gln Ala Ala
                405                 410                 415
Val Leu Pro Pro Leu Arg His Phe Asp Ser Arg Gln Met Pro Leu Ser
            420                 425                 430
Thr Ser Phe Gly Ala Tyr Glu Ser Val Ala Asp Ser Phe Glu Ser Ala
            435                 440                 445
```

```
Leu Arg Ser His Pro Glu Leu Asp Val Asp Asp Glu Ile Arg Val His
        450                 455                 460

Leu Ala Arg Leu Tyr Gly Thr Glu His Glu Lys Val Leu Asp Leu Val
465                     470                 475                 480

Ala Lys Gln Pro Asp Leu Gly Arg Arg Leu Asp Pro Asp Asn Leu Asp
                485                     490                 495

Ile Ala Ala Gln Ala Val Phe Ala Val Ala Glu Glu Ala Ala Val Asp
                500                 505                 510

Leu Ala Asp Val Leu Asp Arg Arg Ile Val Leu Gly Thr Leu Gly Tyr
            515                 520                 525

Val Gln Pro Ala Ala Val Arg Ala Thr Ala Glu Ala Met Ala Gln Val
        530                 535                 540

Thr Gly Trp Ser Ala Glu Leu Ile Asp Ala Gln Cys Gln Ser Tyr Leu
545                 550                 555                 560

Ala Lys Gln Asp Lys Ile Gln Ala Val Leu Lys Pro Tyr Arg
                565                 570
```

METHOD FOR THE FERMENTATIVE PRODUCTION OF L-AMINO ACIDS WITH THE AID OF CORYNEFORM BACTERIA CAPABLE OF USING GLYCERIN AS THE ONLY CARBON SOURCE

The invention relates to recombinant coryneform bacteria in which is (are) expressed at least one or more of the heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC, and also to a method for the fermentative production of L-amino acids, in particular L-lysine and L-tryptophan, with the medium containing glycerol as carbon source, employing these bacteria. These bacteria exhibit the ability for utilization of glycerol and thereby for effective formation and accumulation of L-amino acids.

PRIOR ART

Chemical compounds, which are taken to mean, in particular, L-amino acids, vitamins, nucleosides and nucleotides and D-amino acids, are employed in human medicine, in the pharmaceutical industry, in cosmetics, in the food industry and in animal nutrition.

Many of these compounds are produced by fermentation of strains of coryneform bacteria, in particular *Corynebacterium glutamicum*. Because of the great importance, efforts are continuously being made to improve the production methods. Method improvements can relate to fermentation-related measures such as, for example, stirring and supply with oxygen, or the composition of the nutrient media such as, for example, the sugar concentration during fermentation, or workup to give the product form by, for example, ion-exchange chromatography, or the intrinsic performance characteristics of the microorganism itself.

To improve the performance characteristics of these bacteria, methods of mutagenesis, selection and mutant isolation are employed. In this manner strains are obtained which are resistant to antimetabolites such as the lysine analog 5-(2-aminoethyl)cysteine or the tryptophan analog 5-fluorotryptophan, for example, or are auxotrophic for metabolites of regulatory importance and produce L-amino acids.

For some years, methods of recombinant DNA technology have likewise been used for strain improvement of L-amino acid-producing strains of *Corynebacterium glutamicum*, by amplifying individual amino acid biosynthesis genes and studying the effect on L-amino acid production. A summarizing survey of very varied aspects of the genetics, metabolism and biotechnology of *Corynebacterium glutamicum* may be found in Pühler ((chief ed.) Journal of Biotechnology 104 (1-3), 1-338 (2003)) and Eggeling and Bott ((editors) Handbook of *Corynebacterium glutamicum*, CRC Press, Taylor & Francis Group, Boca Raton (2005)).

The entire fermentation industry for producing L-amino acids currently employs chiefly glucose or sucrose as carbon source, which sugars are obtained in the methoding of agricultural products. However, since the price of these carbon sources is increasing, an alternative which can be carried out by technological means for producing the L-amino acids, preferably L-lysine and L-tryptophan, the utilization of an inexpensive material as an alternative raw material for fermentation, is desirable.

Glycerol (propanetriol) is a natural component of oils and fats and, as a "bridge", binds the fatty acid molecules in the triglycerides. The glycerol molecule is highly polar and therefore readily water soluble. As a coupling product, this valuable raw material is formed in biodiesel production (for example for rapeseed oil methyl ester, RME) and is used in cosmetics, pharmaceutical products, foods and for technical applications. A critical factor for the use of glycerol as a raw material for producing feedstuff components is its cheapness. It may be assumed that with increasing biodiesel production, glycerol will become of greater interest for production of feedstuff additives.

*Corynebacterium glutamicum* wild type uses a multiplicity of monomeric and oligomeric sugars such as glucose, sucrose or maltose as carbon source (Vahjen et al., FEMS Microbiology Ecology 18: 317-328 (1995)), but does not grow on glycerol as sole carbon source.

*Corynebacterium glutamicum* wild type possesses some genes having homology to known genes of glycerol metabolism, but it has not yet been possible to date to explain why growth on glycerol is nevertheless not possible.

OBJECT OF THE INVENTION

The inventors have set themselves the object of providing novel coryneform bacteria which are able to use glycerol as far as possible as sole carbon source. A further object in immediate conjunction therewith was to provide an improved method for fermentative production of L-amino acids, in particular L-lysine and L-tryptophan with the aid of such coryneform bacteria. In particular, glycerol should be made usable thereby for fermentative production of L-amino acids in the most economical manner possible.

DESCRIPTION OF THE INVENTION

This object and also other objects which are not explicitly mentioned but which can be derived or concluded without problems from the facts discussed herein are achieved by provision of coryneform bacteria according to embodiment 1 and also a method according to embodiment 19.

Embodiment 1

A recombinant coryneform bacterium in which is (are) expressed at least one or more of the heterologous polynucleotides of glycerol metabolism selected from the group glpA, glpB, glpC, glpD, glpE, glpF, glpG, glpK, glpQ, glpT, glpX, gldA, dhaK, dhal, dhaM, dhaR, fsa and talC.

Embodiment 19

A method for the fermentative production of L-amino acids, characterized in that the following steps are carried out:
  a) culturing the recombinant coryneform bacteria producing the desired L-amino acid as described in embodiments 1 to 18 in a medium containing glycerol or, if appropriate, in addition one or more further carbon sources under conditions in which the desired L-amino acid accumulates in the medium or in the cells, and, if appropriate,
  b) isolating the desired L-amino acid, in which if appropriate components of the fermentation broth and/or biomass remain in the end product in their totality or in fractions (>0 to 100%).

Expedient modifications and developments of the invention are protected in the subclaims which refer back to embodiment 1 or embodiment 19, respectively.

The invention relates to recombinant coryneform bacteria which, in particular, already excrete L-amino acids and in which is (are) expressed at least one or more of the nucleotide sequence(s) encoding the heterologous gene products of glycerol metabolism selected from the group glpA, glpB, glpC, glpD, glpE, glpF, glpG, glpK, glpQ, glpT, glpX, gldA, dhaK, dhaL, dhaM, dhaR, fsa and talC. These bacteria exhibit the ability to utilize glycerol.

The bacteria employed include, in particular, coryneform bacteria in which at least one heterologous polynucleotide is expressed which encodes a polypeptide the amino acid sequence of which is at least 80% identical, or at least 90%, in particular at least 95%, preferably at least 98%, particularly preferably at least 99%, and very particularly preferably 100% identical, with an amino acid sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16, SEQ ID No. 18, SEQ ID No. 20, SEQ ID No. 22, SEQ ID No. 24, SEQ ID No. 26, SEQ ID No. 28, SEQ ID No. 30, SEQ ID No. 32, SEQ ID No. 34 and SEQ ID No. 36.

Said bacteria preferably contain at least one heterologous polynucleotide selected from the group consisting of:
a) polynucleotide having the nucleotide sequence SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35 and nucleotide sequences complementary thereto
b) polynucleotide having a nucleotide sequence which, in the context of degeneracy of the genetic code, corresponds to SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35;
c) polynucleotide sequence having a sequence which hybridizes under stringent conditions to the sequence complementary to sequence SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35, in which the stringent conditions are preferably achieved by a wash step, in which the temperature varies over a range from 64° C. to 68° C. and the salt concentration of the buffer varies over a range from 2×SSC to 0.1×SSC;
d) polynucleotide having a sequence SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35, which contains functionally neutral sense mutations,
the polynucleotides encoding enzymes of glycerol metabolism.

The invention likewise relates to a method for the fermentative production of L-amino acids, in particular L-lysine and L-tryptophan with the medium containing glycerol as carbon source, with employment of recombinant coryneform bacteria which in particular already produce L-amino acids and in which at least one or more of the heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC or nucleotide sequences encoding their gene products is or are expressed.

Preferably, use is made of the bacteria according to the invention.

When hereinafter L-amino acids or amino acids are mentioned, they are to be taken to mean one or more of the proteinogenic amino acids including salts thereof selected from the group L-aspartic acid, L-asparagine, L-threonin, L-serine, L-glutamic acid, L-glutamine, L-glycine, L-alanine, L-cysteine, L-valine, L-methionin, L-isoleucine, L-leucine, L-tyrosine, L-phenylalanine, L-histidine, L-lysine, L-tryptophan, L-arginine and L-proline. Particular preference is given to L-lysine and L-tryptophan. The L-amino acids also include L-homoserine.

Proteinogenic amino acids are taken to mean the amino acids which occur in natural proteins, that is to say in proteins from microorganisms, plants, animals and humans.

Where amino acids are mentioned hereinafter, the term also comprises salts thereof such as, for example, lysine monohydrochloride or lysine sulfate, in the case of the amino acids L-lysine.

"Heterologous genes" or "heterologous nucleotide sequences" according to the invention can originate from any prokaryotic donor organism apart from representatives of the genus *Corynebacterium*. Preferably, use is made of the genes from *Escherichia coli*.

The phrase "expression of heterologous genes" in this context describes the cloning of corresponding genes and their expression in the heterologous system which leads to establishment of intracellular activity or concentration of one or more enzymes or proteins in a microorganism which are encoded by the corresponding DNA, by, for example, generating a vector which contains the desired gene or an allele of this gene and a promoter making possible the expression of the gene and transfers it into the microorganism by transformation, transduction or conjugation and, if appropriate, combines these measures.

Alleles are taken to mean alternative forms of a given gene. The forms are distinguished by differences in the nucleotide sequence.

The protein or the ribonucleic acid encoded by a nucleotide sequence, that is to say a gene or an allele, is termed gene product.

This invention also relates to a method for the fermentative production of L-amino acids, characterized in that the following steps are carried out:
a) culturing the recombinant coryneform bacteria producing the desired L-amino acid in which at least one or more of the heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC or nucleotide sequences or alleles encoding their gene products is or are expressed in a medium containing glycerol or, if appropriate, in addition one or more further carbon sources under conditions in which the desired L-amino acid accumulates in the medium or in the cells, and if appropriate,
b) isolating the desired L-amino acid, in which if appropriate components of the fermentation broth and/or biomass remain in the end product in their totality or in fractions (>0 to 100%).

The coryneform bacteria used preferably already produce L-amino acids, in particular L-lysine and L-tryptophan, on conventional carbon sources such as, for example, glucose or sucrose, before the expression of one or more of the genes of glycerol metabolism. The glycerol used can be used individually or as a mixture, wherein the fraction of the glycerol should preferably be >10 to 100%.

It has been found that coryneform bacteria after heterologous expression of one or more of the genes of glycerol metabolism produce L-amino acids, in particular L-lysine and L-tryptophan, from glycerol as sole carbon source.

Recombinant bacteria of the invention are generated, for example, by transformation, transduction or conjugation, or a combination of these methods using a vector which contains the desired gene, an allele of this gene or parts thereof and a promoter making possible the expression of the gene. The heterologous expression is achieved, in particular, by integration of the gene or of the alleles into the chromosome of the microorganisms or an extrachromosomally replicating vector.

The promoter can be the inherent regulatory sequence situated upstream of the gene, or a promoter from coryneform bacteria is fused with the gene. An overview of known promoters from *Corynebacterium glutamicum* is described by Pátek et al. (Journal of Biotechnology 104, 311-323 (2003)).

The bacteria on which the measures of the invention are carried out and which are thereby starting point of the present invention can produce amino acids from glucose, sucrose, lactose, fructose, maltose, molasses, starch, cellulose, or from ethanol. These are representative of coryneform bacteria.

Among the coryneform bacteria, preference is given to the genus *Corynebacterium*. Particular preference is given to amino acid-excreting strains which are based on the following species:
  *Corynebacterium* efficiens, such as, for example, strain DSM44549,
  *Corynebacterium glutamicum*, such as, for example, strain ATCC13032,
  *Corynebacterium thermoaminogenes*, such as, for example, strain FERM BP-1539, and
  *Corynebacterium* ammoniagenes, such as, for example, strain ATCC6871,
very particular preference being given to the species *Corynebacterium glutamicum*.

Some representatives of the species *Corynebacterium glutamicum* are also known under other species names in the prior art. These include, for example:
  *Corynebacterium acetoacidophilum* ATCC13870
  *Corynebacterium lilium* DSM20137
  *Corynebacterium melassecola* ATCC17965
  *Brevibacterium flavum* ATCC14067
  *Brevibacterium lactofermentum* ATCC13869 and
  *Brevibacterium divaricatum* ATCC14020
Known representatives of amino acid-excreting strains of coryneform bacteria are, for example
the L-lysine-producing strains
  *Corynebacterium glutamicum* DM58-1/pDM6 (=DSM4697) described in EP 0 358 940
  *Corynebacterium glutamicum* MH20 (=DSM5714) described in EP 0 435 132
  *Corynebacterium glutamicum* AHP-3 (=FermBP-7382) described in EP 1 108 790
  *Corynebacterium thermoaminogenes* AJ12521 (=FERM BP-3304) described in U.S. Pat. No. 5,250,423
or the L-tryptophan-producing strains
  *Corynebacterium glutamicum* K76 (=FermBP-1847) described in U.S. Pat. No. 5,563,052
  *Corynebacterium glutamicum* BPS13 (=FermBP-1777) described in U.S. Pat. No. 5,605,818
  *Corynebacterium glutamicum* FermBP-3055 described in U.S. Pat. No. 5,235,940
Information on taxonomic classification of strains of this group of bacteria may be found, inter alia, in Seiler (Journal of General Microbiology 129, 1433-1477 (1983)), Kämpfer and Kroppenstedt (Canadian Journal of Microbiology 42, 989-1005 (1996)), Liebl et al (International Journal of Systematic Bacteriology 41, 255-260 (1991)) and in U.S. Pat. No. 5,250,434.

Strains having the designation "ATCC" can be obtained from the American Type Culture Collection (Manassas, Va., USA). Strains having the designation "DSM" can be obtained from the German Collection of Microorganisms and Cell Cultures (DSMZ, Brunswick, Germany). Strains having the designation "FERM" can be obtained from the National Institute of Advanced Industrial Science and Technology (AIST Tsukuba Central 6, 1-1-1 Higashi, Tsukuba Ibaraki, Japan). Said strain of *Corynebacterium thermoaminogenes* (FERM BP-1539) is described in U.S. Pat. No. 5,250,434.

The nucleotide sequences of the genes or open reading frames (ORF) of *Escherichia coli* are part of the prior art and can be taken from the genome sequence of *Escherichia coli* published by Blattner et al. (Science 277: 1453-1462 (1997)).

The nucleotide sequence for the genes glpA, glpB, glpC, glpD, glpE, glpF, glpG, glpK, glpQ, glpT and glpX, for example, are likewise known from *Shigella flexneri* (Accession No.: NC 004337 (sequence of the entire genome)) and *Salmonella typhimurium* (Accession No.: NC 003197 (sequence of the entire genome)) likewise belonging to the family Enterobacteriaceae. In addition, from *Salmonella typhimurium* (Accession No.: NC 003197 (sequence of the entire genome)) the nucleotide sequence for the genes gldA and talC, and from *Shigella flexneri* (Accession No.: NC 004337 (sequence of the entire genome)) the nucleotide sequence for the genes dhaK, dhaL, dham, dhaR and fsa is known.

The genes and activities of glycerol metabolism are also described as a summary in Lin (in: Neidhardt (ed), *Escherichia coli* and *Salmonella*, American Society for Microbiology, Washington, D.C., USA: 307-342 (1996)).

The glycerophosphate regulon (glp) containing the genes of glycerol transport and metabolism consists of five operons which lie on three different gene sites on the *E. coli* chromosome (Cozzarelli et al., Journal of Molecular Biology 31: 371-387 (1968)).

A regulon is a unit of genes which, although they are localized at various sites of a genome, their expression is controlled by the same regulator proteins. An operon is a unit of jointly regulated genes at one gene site.

The operon glpFKX (Cozzarelli and Lin, Journal of Bacteriology 91: 1763-1766 (1966); Weissenborn et al., Journal of Biological Chemistry 267: 6122-6131 (1992)), which encodes the glycerol facilitator GlpF and the glycerol kinase GlpK and a fructose-1,6-bisphosphatase II GlpX (Donahue et al., Journal of Bacteriology 182 (19): 5624-5627 (2000)) is situated at 88 min. In the operon mapped at 49 min, the genes glpT (glycerol-3-phosphate permease) and glpQ (periplasmic glycerol phosphodiesterase) are associated which are transcribed in the counterclockwise direction. The glpABC operon is arranged in the opposite direction and its genes encode the three subunits of the heterotrimer sn-glycerol-3-phosphate-dehydrogenase, active in the absence of atmospheric oxygen (anaerobic) (Cole et al., Journal of Bacteriology 170: 2448-2456 (1988); Ehrmann et al., Journal of Bacteriology 169: 526-532 (1987)). The glpDEG operon is situated at 75 min on the chromosome and encodes the glycerol-3-phosphate-dehydrogenase GlpD active in the presence of atmospheric oxygen (aerobic) (Cozzarelli et al., Journal of Molecular Biology 31: 371-387 (1968)), the sulfur transferase GlpE (Cozzarelli et al., Journal of Molecular Biology 31: 371-387 (1968)) and the glpG gene having an unknown function (Zeng et al., Journal of Bacteriology 178: 7080-7089 (1996)).

A short summary of the genes and activities of glycerol metabolism is given by the following listing:

glpA Gene:
Description: large subunit of the sn-glycerol-3-phosphate dehydrogenase (anaerobic)
Function: In an anaerobic environment, glycerol-3-phosphate, for energy production, is oxidized by an FAD-dependent glycerol-3-phosphate dehydrogenase (GlpABC) to dihydroxyacetone phosphate which can take part in glycolysis as an intermediate. The reduction equivalents released in this oxidation reaction are transferred by the flavoenzyme to a membrane-associated cytochrome complex, wherein fumarate or nitrate acts as terminal electron acceptor (Lin, in: Neidhardt (ed), *Escherichia coli* and *Salmonella*, American Society for Microbiology, Washington, D.C., USA: 307-342 (1996)). While the electrons are passed through the cytochrome complex, the energy being released is utilized for pumping protons through the membrane from the cytoplasmic side to the periplasmic side. With the proton gradient generated at the membrane, both the electrical and chemical potential change, which drives the membrane-bound ATPase and as a result ATP can be generated.
EC No.: 1.1.99.5
Reference: Blattner et al.; Science 277(5331): 1453-1474 (1997)
SEQ ID No.: 1
Accession No.: U00096 (region: 2350669-2352297)
Alternative gene name: b2241 glpB Gene:
Description: subunit for the membrane anchor of sn-glycerol-3-phosphate dehydrogenase (anaerobic)
Function: see glpA
EC No.: 1.1.99.5
Reference: Blattner et al.; Science 277(5331): 1453-1474 (1997)
SEQ ID No.: 3
Accession No.: U00096 (region: 2352287-2353546)
Alternative gene name: b2242 glpC Gene:
Description: small subunit of sn-glycerol-3-phosphate dehydrogenase (anaerobic)
Function: see glpA
EC No.: 1.1.99.5
Reference: Blattner et al.; Science 277(5331): 1453-1474 (1997)
SEQ ID No.: 5
Accession No.: U00096 (region: 2353543-2354733)
Alternative gene name: b2243 glpD Gene:
Description: glycerol-3-phosphate dehydrogenase (aerobic)
Function: GlpD was identified as an aerobic glycerol-3-phosphate dehydrogenase (Cozzarelli et al., Journal of Molecular Biology 31: 371-387 (1968)). In an aerobic environment, glycerol-3-phosphate, for energy production, is oxidized by this FAD-dependent glycerol-3-phosphate dehydrogenase (GlpD) to dihydroxyacetone phosphate which can participate in glycolysis as an intermediate. The reduction equivalents released in this oxidation reaction are transferred by the flavoenzyme to a membrane-associated cytochrome complex, wherein molecular oxygen or nitrate acts as terminal electron acceptor (Lin, in: Neidhardt (ed), *Escherichia coli* and *Salmonella*, American Society for Microbiology, Washington, D.C., USA: 307-342 (1996)) While the electrons are passed through the cytochrome complex, the energy being released is used for pumping protons through the membrane from the cytoplasmic side to the periplasmic side. With the proton gradient generated at the membrane both the electrical and also the chemical potential change, which drives the membrane-bound ATPase and as a result ATP can be generated. The open reading frame of the glpD gene consists of 501 codons and the translated sequence encodes a protein having a molecular weight of 57 kDa (Austin and Larson, Journal of Bacteriology 173: 101-107 (1991)).
EC No.: 1.1.99.5
Reference: Blattner et al.; Science 277(5331): 1453-1474 (1997)
SEQ ID No.: 7
Accession No.: U00096 (region: 3560036-3561541)
Alternative gene name: b3426, glyD glpE Gene:
Description: sulfur transferase; acidic, cytoplasmic rhodanese
Function: GlpE was identified as a sulfur transferase (Cozzarelli et al., Journal of Molecular Biology 31: 371-387 (1968)). The acidic cytoplasmic rhodanese encoded by the glpE gene having a molecular weight of 12 kDa catalyzes as dimer the transfer of sulfur to the sulfur acceptor thioredoxin 1 (Ray et al., Journal of Bacteriology 182: 2277-2284 (2000)).
EC No.: 2.8.1.1
Reference: Blattner et al.; Science 277(5331): 1453-1474 (1997)
SEQ ID No.: 9
Accession No.: U00096 (region: 3559520-3559846)
Alternative gene name: b3425 glpF Gene:
Description: glycerol facilitator GlpF
Function: The facilitated diffusion of glycerol from the nutrient medium is catalyzed by the glycerol facilitator GlpF (Borgnia and Agre, Proc. Natl. Acad. Sci. U.S.A. 98: 2888-2893 (2001)) which forms a substrate-specific channel having a pore size of 0.4 nm (Heller et al., Journal of Bacteriology 144: 274-278 (1980)).
EC No.: —
Reference: Blattner et al.; Science 277(5331): 1453-1474 (1997)
SEQ ID No.: 11
Accession No.: U00096 (region: 4115268-4116113)
Alternative gene name: b3927 glpG Gene:
Description: gene of the glp regulon
Function: The physiological function of glpG is still unknown. The glpG gene product is a basic cytoplasmic or membrane-associated protein having a molecular weight of 28 kDa (Zeng et al., Journal of Bacteriology 178: 7080-7089 (1996)).
EC No.: —
Reference: Blattner et al.; Science 277(5331): 1453-1474 (1997)
SEQ ID No.: 13
Accession No.: U00096 (region: 3558645-3559475)
Alternative gene name: b3424 glpK Gene:
Description: glycerol kinase GlpK (ATP-dependent)
Function: Cytoplasmic glycerol is immediately phosphorylated by the ATP-dependent glycerol kinase K which in its enzymatically active form is present associated with the glycerol facilitator GlpF (Voegele et al., Journal of Bacteriology 175: 1087-1094 (1993)).
EC No.: 2.7.1.30
Reference: Blattner et al.; Science 277(5331): 1453-1474 (1997)

SEQ ID No.: 15
Accession No.: U00096 (region: 4113737-4115245)
Alternative gene name: b3926
glpQ Gene:
Description: Glycerol phosphodiesterase
Function: Glycerophosphate diesters, the deacetylated breakdown product of phospholipids (Lin, in: Neidhardt (ed), *Escherichia coli* and *Salmonella*, American Society for Microbiology, Washington, D.C., USA: 307-342 (1996)), are hydrolyzed in the periplasma by the phosphodiesterase GlpQ localized there to form alcohol and glycerol-3-phosphate (Larson et al., Journal of Biological Chemistry 258: 5428-5432 (1983)). Since the glycerol phosphodiesterase is thus ascribed an extracytoplasmic action the gene product derived from the heterologous glpQ gene in the claimed bacteria must comprise a leader peptide, as is typical of excreted proteins of Gram-positive bacteria (Nielsen et al., Protein Engineering Design and Selection 10:1-6 (1997)). This characteristic signal sequence enables export of the GlpQ protein mediated by the general secretion system (Sec system) via the cytoplasmic membrane (Kell and Young, Current opinion in microbiology 3:238-243 (2000); Mukamolova et al., Molecular Microbiology 46:611-621 (2002a); Molecular Microbiology 46:613-635 (2002b)).
EC No.: 3.1.4.46
Reference: Blattner et al.; Science 277(5331): 1453-1474 (1997)
SEQ ID No.: 17
Accession No.: U00096 (region: 2347957-2349033)
Alternative gene name: b2239
glpT Gene:
Description: Glycerol-3-phosphate permease
Function: Glycerol-3-phosphate is transported by the permease GlpT (Eiglmeier et al., Molecular Microbiology 1: 251-258 (1987); Larson et al., Journal of Bacteriology 152: 1008-1021 (1982)) into the cell interior in an exchange for inorganic phosphate (Auer et al., Biochemistry 40: 6628-6635 (2001)) The energy required for the transport is provided by this antiport and at the same time accumulation of the toxic phosphate is prevented (Xavier et al., Journal of Bacteriology 177: 699-704 (1995)).
EC No.: —
Reference: Blattner et al.; Science 277(5331): 1453-1474 (1997)
SEQ ID No.: 19
Accession No.: U00096 (region: 2349038-2350396)
Alternative gene name: b2240
glpX Gene:
Description: Fructose-1,6-bisphosphatase II
Function: To date, no physiological role of the enzyme GlpX has been found. A mutation in fbp, the gene for fructose-1,6-bisphosphatase I, was not complemented by GlpX. However, a functional importance nevertheless appears certain, since mutants which have a fault in glycolysis owing to a pfka (phosphofructokinase A) mutation grow much more slowly without GlpX (Donahue et al.; Journal of Bacteriology 182(19): 5624-5627 (2000)).
EC No.: 3.1.3.11
Reference: Blattner et al.; Science 277(5331): 1453-1474 (1997)
SEQ ID No.: 21
Accession No.: U00096 (region: 4112592-4113602)
Alternative gene name: 3925

In addition to the genes of glycerol transport and metabolism, the following genes of the breakdown of various intermediates and end products of said metabolism can be expressed heterologously:
gldA Gene:
Description: Glycerol dehydrogenase (NAD)
Function: Glycerol dehydrogenase catalyzes the reversible NAD-dependent reaction of glycerol to form dihydroxyacetone (Truniger and Boos, Journal of Bacteriology 176 (6): 1796-1800 (1994)).
EC No.: 1.1.1.6
Reference: Blattner et al.; Science 277(5331): 1453-1474 (1997)
SEQ ID No.: 23
Accession No.: U00096 (region: 4135955-4137097)
Alternative gene name: b3945
dhaK Gene:
Description: Subunit of dihydroxyacetone kinase, N-terminal domain
Function: Dihydroxyacetone kinase, in its function as phosphoenolpyruvate (PEP)-dependent dihydroxyacetone phosphotransferase, catalyzes the reaction of dihydroxyacetone to form dihydroxyacetone phosphate (Gutknecht et al., The EMBO Journal 20(10): 2480-2486 (2001)). DhaK carries the dihydroxyacetone binding site.
EC No.: 2.7.1.29
Reference: Blattner et al.; Science 277(5331): 1453-1474 (1997)
SEQ ID No.: 25
Accession No.: U00096 (region: 1248991-1250091)
Alternative gene name: dhaK1, ycgT, b1200
dhaL Gene:
Description: Subunit of dihydroxyacetone kinase, C-terminal domain
Function: Dihydroxyacetone kinase, in its function as a PEP-dependent dihydroxyacetone phosphotransferase, catalyzes the reaction of dihydroxyacetone to form dihydroxyacetone phosphate (Gutknecht et al., The EMBO Journal 20(10): 2480-2486 (2001)). DhaL carries ADP as cofactor for the transfer of phosphate from DhaM to dihydroxyacetone.
EC No.: 2.7.1.29
Reference: Blattner et al.; Science 277(5331): 1453-1474 (1997)
SEQ ID No.: 27
Accession No.: U00096 (region: 1248348-1248980)
Alternative gene name: dhaK2, ycgS, b1199
dhaM Gene:
Description: PTS protein subunit of dihydroxyacetone kinase, multiphosphoryl transfer protein
Function: Dihydroxyacetone kinase, in its function as a PEP-dependent dihydroxyacetone phosphotransferase, catalyzes the reaction of dihydroxyacetone to form dihydroxyacetone phosphate (Gutknecht et al., The EMBO Journal 20(10): 2480-2486 (2001)). DhaM consists of three domains having a similarity to the three domains of the phosphoenolpyruvate-dependent phosphotransferase system. Phosphorylated DhaM transfers the phosphate to the DhaL-bound ADP.
EC No.: 2.7.1.29
Reference: Blattner et al.; Science 277(5331): 1453-1474 (1997)
SEQ ID No.: 29
Accession No.: U00096 (region: 1246919-1248340)
Alternative gene name: dhaH, ycgC, b1198
dhaR Gene:
Description: Activator of the dha operon (dhaKLM)

Function: Transcriptional activator, stimulates the transcription of the dha operon from a sigma70 promoter (Bachler et al., The EMBO Journal 24(2): 283-293 (2005))
EC No.: —
Reference: Blattner et al.; Science 277(5331): 1453-1474 (1997)
SEQ ID No.: 31
Accession No.: U00096 (region: 1250280-1252208)
Alternative gene name: ycgU, b1201
fsa Gene:
Description: Fructose-6-phosphate aldolase I
Function: Fructose-6-phosphate aldolase I catalyzes an aldol cleavage of fructose-6-phosphate, substrates of the enzyme are dihydroxyacetone and also fructose-6-phosphate and glyceraldehyde-3-phosphate, and does not utilize fructose, fructose-1-phosphate, fructose-1,6-bisphosphate or dihydroxy-acetone phosphate (Schurmann and Sprenger, Journal of Biological Chemistry 276(14): 11055-11061 (2001))
EC No.: 4.1.2.—
Reference: Blattner et al.; Science 277(5331): 1453-1474 (1997)
SEQ ID No.: 33
Accession No.: U00096 (region: 862793-863527)
Alternative gene name: mipB, ybiZ, B0825
talC Gene:
Description: Fructose-6-phosphate aldolase II
Function: Fructose-6-phosphate aldolase II catalyzes an aldol cleavage of fructose-6-phosphate (Schurmann and Sprenger, Journal of Biological Chemistry 276(14): 11055-11061 (2001)). The talC gene is situated directly next to the gldA gene.
EC No.: 4.1.2.—
Reference: Blattner et al.; Science 277(5331): 1453-1474 (1997)
SEQ ID No.: 35
Accession No.: U00096 (region: 4137069-4137731)
Alternative gene name: fsaB, yijG, b3946

The nucleic acid sequences can be taken from the databases of the National Center for Biotechnology Information (NCBI) of the National Library of Medicine, (Bethesda, Md., USA), the nucleotide sequence database of the European Molecular Biologies Laboratories (EMBL, Heidelberg, Germany and Cambridge, UK) or the DNA database of Japan (DDBJ, Mishima, Japan).

For the sake of better clarity, the known sequences for the genes in question of *Escherichia coli* are described SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 and SEQ ID No. 35.

The open reading frames described in the text positions cited can be used according to the invention. In addition, use can be made of alleles of the genes or open reading frames which result from the degeneracy of the genetic code or owing to functionally neutral sense mutations.

Alleles of the treated genes which contain functionally neutral sense mutations include, inter alia, those which lead to at most 13, or at most 10, preferably at most 7, or at most 5, very particularly preferably at most 3 or at most 2, or to at least one conservative amino acid replacement in the protein encoded by them.

Among the aromatic amino acids, conservative replacements are considered to be when phenylalanine, tryptophan and tyrosine are exchanged for one another. Among the hydrophobic amino acids, conservative replacements are considered to be when leucine, isoleucine and valine are exchanged for one another. Among the polar amino acids, conservative replacements are considered to be when glutamine and asparagine are exchanged for one another. Among the basic amino acids, conservative replacements are considered to be when arginine, lysine and histidine are exchanged for one another. Among the acidic amino acids, conservative replacements are considered to be when aspartic acid and glutamic acid are exchanged for one another. Among the hydroxyl-containing amino acids, conservative replacements are considered to be when serine and threonine are exchanged for one another.

In the same manner, use can also be made of those nucleotide sequences which encode variants of said proteins which, in addition at the N or C terminus have an extension or shortening by at least one (1) amino acid. This extension or shortening is no more than 13, 10, 7, 5, 3 or 2 amino acids or amino acid radicals.

It is known that host-specific enzymes, what are termed aminopeptidases, remove the terminal methionine in protein synthesis.

The suitable alleles also include those which encode proteins in which at least one (1) amino acid is inserted or deleted. The maximum number of such changes termed indels can be 2, 3, 4, 5, but in no case more than 6 amino acids.

The suitable alleles include, in addition, those which are obtainable by hybridization, in particular under stringent conditions or use of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35 or parts thereof, in particular the coding regions, or of the sequences complementary thereto.

Instructions for identifying DNA sequences by means of hybridization may be found by those skilled in the art, inter alia, in the handbook "The DIG System Users Guide for Filter Hybridisation" from Boehringer Mannheim GmbH (Mannheim, Germany, 1993) and in Liebl et al. (International Journal of Systematic Bacteriology 41: 255-260 (1991)). Hybridization takes place under stringent conditions, that is to say hybrids are formed only for which probe and target sequence, that is to say the polynucleotides treated with the probe, are at least 70% identical. It is known that the stringency of hybridization including the wash steps is affected or determined by varying the buffer composition, the temperature and the salt concentration. The hybridization reaction is generally carried out at relatively low stringency compared with the wash steps (Hybaid Hybridisation Guide, Hybaid Limited, Teddington, UK, 1996).

For the hybridization reaction, for example use can be made of a buffer equivalent to 5×SSC buffer at a temperature of approximately 50° C.-68° C. In this case probes can also hybridize with polynucleotides which have less than 70% identity to the sequence of the probe. Such hybrids are less stable and are removed by washing under stringent conditions. This can be achieved, for example, by lowering the salt concentration to 2×SSC and if appropriate subsequently 0.5× SSC (The DIG System User's Guide for Filter Hybridisation, Boehringer Mannheim, Mannheim, Germany, 1995), a temperature of approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. being set. Temperature ranges of approximately 64° C.-68° C. or approximately 66° C.-68° C. are preferred. It is if appropriate possible to lower the salt concentration to a concentration equivalent to 0.2×SSC or 0.1×SSC. By stepwise elevation of the hybridization temperature in steps of approximately 1-2° C. from 50° C. to 68° C., polynucleotide fragments can be obtained which have, for example, at least 70%, or at least 80% or at least 90%, at least 91%, at least 92%, at least 93%, at least 94%, at least 95%, at least 96%, at least 97%, at least 98%, or at least 99% identity to the sequence of the probe used or to the nucleotide sequences represented in SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35. Further guidance on hybridization is obtainable on the market in the form called kits (for example DIG Easy Hyb from Roche Diagnostics GmbH, Mannheim, Germany, Catalog No. 1603558).

Use can also be made of polynucleotides from *Bacillus subtilis* (Accession No.: NC 000964 (sequence of the entire genome)) and *Streptomyces coelicolor* (Accession No.: NC 003888 (sequence of the entire genome)) which have, for example, at least 70%, or at least 80%, or at least 90%, at least 91%, at least 92%, at least 93%, at least 94%, at least 95%, at least 96%, at least 97%, at least 98%, or at least 99% identity to the nucleotide sequences represented in SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35 and have the functions described. The nucleotide sequences of the genes and ORFs known from the genome projects are part of the prior art and can be taken from various publications, patent applications and also the database of the National Center for Biotechnology Information (NCBI) of the National Library of Medicine (Bethesda, Md., USA).

Expression of the genes of glycerol metabolism can be detected with the aid of 1- and 2-dimensional protein gel separation and subsequent optical identification of the protein concentration in the gel using corresponding evaluation software. A customary method for preparation of the protein gels in the case of coryneform bacteria and for identification of the proteins is the procedure described by Hermann et al. (Electrophoresis, 22:1712-23 (2001)). The protein concentration can likewise be analyzed by Western blot hybridization using an antibody specific for the protein to be detected (Sambrook et al., Molecular cloning: a laboratory manual. 2nd Ed. Cold Spring Harbor Laboratory Press, Cold Spring Harbor, N.Y., 1989) and subsequent optical evaluation using corresponding software for determination of concentration (Lohaus and Meyer (1998) Biospectrum 5:32-39; Lottspeich (1999) Angewandte Chemie 111:2630-2647). The activity of DNA-binding proteins can be measured by means of DNA band shift assays (also termed gel retardation) (Wilson et al. (2001) Journal of Bacteriology 183:2151-2155). The effect of DNA-binding proteins on the expression of other genes can be detected by various well described methods of the reporter gene assay (Sambrook et al., Molecular cloning: a laboratory manual. 2nd Ed. Cold Spring Harbor Laboratory Press, Cold Spring Harbor, N.Y., 1989). The intracellular enzymatic activities can be determined by various described methods (Donahue et al. (2000) Journal of Bacteriology 182(19): 5624-5627; Ray et al. (2000) Journal of Bacteriology 182(8): 2277-2284; Freedberg et al. (1973) Journal of Bacteriology 115(3): 816-823).

The heterologous genes are expressed, for example, with the aid of episomal plasmids. Suitable plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene 107:69-74 (1991)) are based on the cryptic plasmids pHM1519, pBL1 or pGA1. Other plasmid vectors such as, for example, those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891) can be used in the same manner. A survey of native plasmids from amino acid-producing coryneform bacteria is available in the Handbook of *Corynebacterium glutamicum* (Tauch, Chapter 4, 57-80, editors: Eggeling and Bott, CRC Press, Taylor & Francis Group, Boca Raton (2005)).

In addition, suitable plasmid vectors are those with the aid of which the method of gene amplification by integration into the chromosome can be employed, for instance as has been described, for example, by Reinscheid et al. (Applied and Environmental Microbiology 60, 126-132 (1994)) for duplication or amplification of the hom-thrb operon in WO03/040373. In this method the gene is cloned into a plasmid vector which can replicate in a host (typically *E. coli*), but not in *C. glutamicum*. Vectors which come into consideration are, for example, pSUP301 (Simon et al., Bio/Technology 1, 784-791 (1983)), pK18mob or pK19mob (Schäfer et al., Gene 145, 69-73 (1994)), PGEM-T (Promega corporation, Madison, Wis., USA), pCR2.1-TOPO (Shuman (1994), Journal of Biological Chemistry 269: 32678-84; U.S. Pat. No. 5,487, 993), pCR®Blunt (from Invitrogen, Groningen, Netherlands; Bernard et al., Journal of Molecular Biology, 234: 534-541 (1993)), pEM1 (Schrumpf et al, 1991, Journal of Bacteriology 173:4510-4516) or pBGS8 (Spratt et al., 1986, Gene 41: 337-342). The plasmid vector which contains the heterologous gene to be amplified, if appropriate including the expression and/or regulation signals, and the edge regions of a non-essential homologous gene, is subsequently transferred into the desired strain of *C. glutamicum* by conjugation or transformation. The conjugation method is described, for example, in Schäfer et al. (Applied and Environmental Microbiology 60, 756-759 (1994)). Methods for transformation are described, for example, in Thierbach et al. (Applied Microbiology and Biotechnology 29, 356-362 (1988)), Dunican and Shivnan (Bio/Technology 7, 1067-1070 (1989)) and Tauch et al. (FEMS Microbiology Letters 123, 343-347 (1994)). After homologous recombination by means of a crossover event, the resultant strain contains a copy of the heterologous gene including the plasmid vector at the desired gene site of the *C. glutamicum* chromosome which was predetermined via the homologous nucleotide sequences on the plasmid. By means of a suitable second, excision-causing cross-over event in the target gene or in the target sequence, incorporation of only the heterologous gene is achieved. In this case, at the respective natural gene site, no nucleotide sequence capable of episomal replication in the microorganisms remains, no nucleotide sequence capable of transposition and no nucleotide sequence conferring resistance to antibiotics.

In addition, it can be advantageous for the production of L-amino acids, in addition to the functional expression of one or more of the heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC, to amplify, in particular overexpress, or attenuate, in particular reduce the expression, of one or more enzymes of the metabolic pathways which increase or decrease the formation of the desired amino acid, such as, for example, the biosynthetic pathway, glycolysis, anaplerosis, the citric acid cycle, the pentosphosphate cycle, amino acid export and if appropriate regulatory proteins.

The expression "amplification" or "amplify" describes in this context the increase in intracellular activity or concentration of one or more enzymes or proteins in a microorganism which are encoded by the corresponding DNA by, for example, increasing the number of copies of the gene or genes, using a strong promoter or a gene or allele which encodes a corresponding enzyme or protein having a high activity and if appropriate combining these measures.

By the measures of amplification, in particular overexpression, the activity or concentration of the corresponding protein is generally increased by at least 10%, 25%, 50%, 75%, 100%, 150%, 200%, 300%, 400% or 500%, at most to 1000% or 2000%, based on that of the wild type protein or the activity or concentration of the protein in the starting microorganism.

To achieve an overexpression, the copy number of the corresponding genes can be increased, or the promoter and regulation region or the ribosome binding site which is situated upstream of the structural gene can be mutated. Expression cassettes which are incorporated upstream of the structural gene act in the same manner. By inducible promoters it is, in addition, possible to increase the expression in the course of the fermentative amino acid production. By measures for extending the life of m-RNA, likewise expression is improved. In addition, by hindering the breakdown of the enzyme protein, likewise the enzyme activity is amplified. The genes or gene constructs can be present either in plasmids with different copy numbers or be integrated in the chromosome and amplified. Alternatively, in addition, overexpression of the genes in question can be achieved by altering the media composition and culture procedure.

Instructions in this respect can be found by those skilled in the art, inter alia, in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European patent 0 472 869, in U.S. Pat. No. 4,601,893, in Schwarzer and Pühler (Bio/Technology 9, 84-87 (1991), in Reinscheid et al. (Applied and Environmental Microbiology 60, 126-132 (1994)), in LaBarre et al. (Journal of Bacteriology 175, 1001-1007 (1993)), in the patent application WO 96/15246, in Malumbres et al. (Gene 134, 15-24 (1993)), in the Japanese laid-open publication JP-A-10-229891, in Jensen and Hammer (Biotechnology and Bioengineering 58, 191-195 (1998)), in Makrides (Microbiological Reviews 60:512-538 (1996)) and in known textbooks of genetics and molecular biology.

For amplification, genes are overexpressed, for example, with the aid of episomal plasmids. Suitable plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene 107:69-74 (1991)) are based on the cryptic plasmids pHM1519, pBL1 or pGA1. Other plasmid vectors such as, for example, those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891), can be used in the same manner.

In addition, suitable plasmid vectors are those with the aid of which the method of gene amplification by integration into the chromosome can be employed, for instance as has been described, for example, by Reinscheid et al. (Applied and Environmental Microbiology 60, 126-132 (1994) for the duplication or amplification of the hom-thrB operon. In this method the complete gene is cloned into a plasmid vector which can replicate in a host (typically E. coli), but not in C. glutamicum. Vectors which come into consideration are, for example, pSUP301 (Simon et al., Bio/Technology 1, 784-791 (1983)), pK18mob or pK19mob (Schäfer et al., Gene 145, 69-73 (1994)), pGEM-T (Promega corporation, Madison, Wis., USA), pCR2.1-TOPO (Shuman (1994), Journal of Biological Chemistry 269: 32678-84; U.S. Pat. No. 5,487,993), pCR®Blunt (from Invitrogen, Groningen, Netherlands; Bernard et al., Journal of Molecular Biology, 234: 534-541 (1993)), pEM1 (Schrumpf et al, 1991, Journal of Bacteriology 173:4510-4516) or pBGS8 (Spratt et al., 1986, Gene 41: 337-342). The plasmid vector which contains the gene to be amplified is subsequently transferred into the desired strain of C. Glutamicum by conjugation or transformation. The method of conjugation is described, for example, in Schäfer et al. (Applied and Environmental Microbiology 60, 756-759 (1994)). Methods for transformation are described, for example, in Thierbach et al. (Applied Microbiology and Biotechnology 29, 356-362 (1988)), Dunican and Shivnan (Bio/Technology 7, 1067-1070 (1989)) and Tauch et al. (FEMS Microbiology Letters 123, 343-347 (1994). After homologous recombination by means of a crossover event, the resultant strain contains at least two copies of the gene in question.

A customary method of incorporating one or more additional copies of a gene of C. glutamicum into the chromosome of the desired coryneform bacterium is the method of gene doubling described in WO03/014330 and WO03/040373. For this, in WO03/040373 the nucleotide sequence of the desired ORF, gene or allele, if appropriate including the expression and/or regulation signals is isolated and two copies, preferably in tandem arrangement, are cloned into a vector which is not replicative for C. glutamicum such as, for example, pK18mobsacB or pK19mobsacB (Jäger et al., Journal of Bacteriology 174: 5462-65 (1992)). The vector is subsequently transferred to the desired coryneform bacterium by transformation or conjugation. After homologous recombination by means of a first crossover event causing integration and a suitable second excision-causing cross-over event in the target gene or in the target sequence, incorporation of the additional gene copy is achieved. Thereafter, those bacteria are isolated in which there are two copies of the ORF, gene or allele at the respective natural site instead of the original singular copy present. In this case, at the respective natural gene site, there remains no nucleotide sequence which is capable of/enables episomal replication in microorganisms, no nucleotide sequence which is capable of, enables transposition and no nucleotide sequence which imparts resistance to antibiotics.

The expression "attenuation" in this context describes the reduction or switching off of the intracellular activity of one or more enzymes (proteins) in a microorganism which are encoded by the corresponding DNA by, for example, using a weak promoter or a gene or allele which encodes a corresponding enzyme or protein having a low activity or which inactivates the corresponding gene or enzyme (protein) and if appropriate combining these measures.

By the attenuation measures, the activity or concentration of the corresponding protein is generally lowered to 0 to 75%, 0 to 50%, 0 to 25%, 0 to 10%, or 0 to 5% of the activity or concentration of the wild type protein, or of the activity or concentration of the protein in the starting microorganism.

The elevation or lowering of the protein concentration is detectable via the methods already mentioned hereinbefore (Hermann et al., Electrophoresis, 22:1712-23 (2001); Lohaus and Meyer, Biospektrum 5:32-39 (1998); Lottspeich, Angewandte Chemie 111:2630-2647 (1999); Wilson et al., Journal of Bacteriology 183:2151-2155 (2001)).

The use of endogenous genes is generally preferred. "Endogenous genes" or "endogenous nucleotide sequences" is taken to mean genes or nucleotide sequences present in the population of a species.

Thus, for example for the production of L-lysine, in addition to the expression of one or more heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC, one or more of the genes selected from the group of the genes or alleles of lysine production are amplified, in particular overexpressed. "Genes or alleles of lysine production" are taken to mean all, preferably endogenous, open reading frames, genes or alleles, the amplification/overexpression of which can cause an improvement in lysine production.

The following genes or alleles, inter alia, can be used for this:
accBC, accDA, cstA, cysD, cysE, cysH, cysK, cysN, cysQ, dapA, dapB, dapC, dapD, dapE, dapF, ddh, dps, eno, gap, gap2, gdh, gnd, lysC, lySCFBR, lysE, msiK, opcA, oxyR, ppc, ppcFBR, pgk, pknA, pknB, pknD, pknG, ppsA, ptsH, ptsI, ptsM, pyc, pyc P458S, sigC, sigD, sigE, sigH, sigM, tal, thyA, tkt, tpi, zwa1, zwf and zwf A243T. These are summarized and explained in Table 1.

TABLE 1

Genes and alleles of lysine production

| Name | Description of the coded enzyme or protein | Reference | Accession number |
|---|---|---|---|
| accBC | Acyl-CoA Carboxylase EC 6.3.4.14 (acyl-CoA carboxylase) | Jäger et al. Archives of Microbiology (1996) 166: 76-82 EP1108790; WO0100805 | U35023 AX123524 AX066441 |
| accDA | Acetyl-CoA Carboxylase EC 6.4.1.2 (acetyl-CoA carboxylase) | EP1055725 EP1108790 WO0100805 | AX121013 AX066443 |
| cstA | Carbon Starvation Protein A (carbon starvation protein A) | EP1108790 WO0100804 | AX120811 AX066109 |
| cysD | Sulfate adenylyltransferase subunit II EC 2.7.7.4 (sulfate adenylyltransferase small chain) | EP1108790 | AX123177 |
| cysE | Serine acetyltransferase EC 2.3.1.30 (serine acetyltransferase) | EP1108790 WO0100843 | AX122902 AX063961 |
| cysH | 3'-Phosphoadenylsulfate reductase EC 1.8.99.4 (3'-phosphoadenosine 5'-phosphosulfate reductase) | EP1108790 WO0100842 | AX123178 AX066001 |
| cysK | Cysteine synthase EC 4.2.99.8 (cysteine synthase) | EP1108790 WO0100843 | AX122901 AX063963 |
| cysN | Sulfate adenylyltransferase subunit I EC 2.7.7.4 (sulfate adenylyltransferase) | EP1108790 | AX123176 AX127152 |
| cysQ | Transport protein CysQ (transporter cysQ) | EP1108790 WO0100805 | AX127145 AX066423 |
| dapA | Dihydrodipicolinate synthase EC 4.2.1.52 (dihydrodipicolinate synthase) | Bonnassie et al. Nucleic Acids Research 18: 6421 (1990) Pisabarro et al., Journal of Bacteriology 175: 2743-2749 (1993) EP1108790 WO0100805 EP0435132 EP1067192 EP1067193 | X53993 Z21502 AX123560 AX063773 |
| dapB | Dihydrodipicolinate reductase EC 1.3.1.26 (dihydrodipicolinate reductase) | EP1108790 WO0100843 EP1067192 EP1067193 Pisabarro et al., Journal of Bacteriology 175: 2743-2749 (1993) JP1998215883 JP1997322774 JP1997070291 JP1995075578 | AX127149 AX063753 AX137723 AX137602 X67737 Z21502 E16749 E14520 E12773 E08900 |

TABLE 1-continued

Genes and alleles of lysine production

| Name | Description of the coded enzyme or protein | Reference | Accession number |
|---|---|---|---|
| dapC | N-Succinylaminoketopimelate transaminase<br>EC 2.6.1.17<br>(N-succinyl-diaminopimelate transaminase) | EP1108790<br>WO0100843<br>EP1136559 | AX127146<br>AX064219 |
| dapD | Tetrahydrodipicolinate succinylase<br>EC 2.3.1.117<br>(tetrahydrodipicolinate succinylase) | EP1108790<br>WO0100843<br>Wehrmann et al.<br>Journal of Bacteriology<br>180: 3159-3165 (1998) | AX127146<br>AX063757<br>AJ004934 |
| dapE | N-Succinyldiaminopimelate desuccinylase<br>EC 3.5.1.18<br>(N-succinyl-diaminopimelate desuccinylase) | EP1108790<br>WO0100843<br>Wehrmann et al.<br>Microbiology<br>140: 3349-3356 (1994) | AX127146<br>AX063749<br>X81379 |
| dapF | Diaminopimelate epimerase<br>EC 5.1.1.7<br>(diaminopimelate epimerase) | EP1108790<br>WO0100843<br>EP1085094 | AX127149<br>AX063719<br>AX137620 |
| ddh | Diaminopimelate dehydrogenase<br>EC 1.4.1.16<br>(diaminopimelate dehydrogenase) | EP1108790<br>WO0100843<br>Ishino et al.,<br>Nucleic Acids Research<br>15: 3917-3917 (1987)<br>JP1997322774<br>JP1993284970<br>Kim et al.,<br>Journal of Microbiology and Biotechnology<br>5: 250-256 (1995) | AX127152<br>AX063759<br>Y00151<br><br><br>E14511<br>E05776<br>D87976 |
| dps | DNA protection protein<br>(protection during starvation protein) | EP1108790 | AX127153 |
| eno | Enolase<br>EC 4.2.1.11<br>(enolase) | EP1108790<br>WO0100844<br>EP1090998<br>Hermann et al.,<br>Electrophoresis<br>19: 3217-3221 (1998) | AX127146<br>AX064945<br>AX136862 |
| gap | Glyceraldehyde-3-phosphate dehydrogenase<br>EC 1.2.1.12<br>(glyceraldehyde-3-phosphate dehydrogenase) | EP1108790<br>WO0100844<br>Eikmanns et al.,<br>Journal of Bacteriology<br>174: 6076-6086 (1992) | AX127148<br>AX064941<br>X59403 |
| gap2 | Glyceraldehyde-3-phosphate dehydrogenase<br>EC 1.2.1.12<br>(glyceraldehyde-3-phosphate dehydrogenase 2) | EP1108790<br>WO0100844 | AX127146<br>AX064939 |
| gdh | Glutamate dehydrogenase<br>EC 1.4.1.4<br>(glutamate dehydrogenase) | EP1108790<br>WO0100844<br>Boermann et al.,<br>Molecular Microbiology<br>6: 317-326 (1992) | AX127150<br>AX063811<br>X59404<br>X72855 |
| gnd | 6-Phosphogluconate dehydrogenase<br>EC 1.1.1.44<br>(6-phosphogluconate dehydrogenase) | EP1108790<br><br>WO0100844 | AX127147<br>AX121689<br>AX065125 |
| lysC | Aspartate kinase<br>EC 2.7.2.4<br>(aspartate kinase) | EP1108790<br>WO0100844<br>Kalinowski et al., Molecular Microbiology<br>5: 1197-204 (1991) | AX120365<br>AX063743<br>X57226 |
| lysE | Lysine exporter<br>(lysine exporter protein) | EP1108790<br>WO0100843<br>Vrljić et al., | AX123539<br>AX123539<br>X96471 |

TABLE 1-continued

Genes and alleles of lysine production

| Name | Description of the coded enzyme or protein | Reference | Accession number |
|---|---|---|---|
| | | Molecular Microbiology 22: 815-826 (1996) | |
| msiK | Sugar importer (multiple sugar import protein) | EP1108790 | AX120892 |
| opcA | Glucose-6-phosphate dehydrogenase (subunit of glucose-6-phosphate dehydrogenase) | WO0104325 | AX076272 |
| oxyR | Transcription regulator (transcriptional regulator) | EP1108790 | AX122198 AX127149 |
| ppc$^{FBR}$ | Phosphoenolpyruvate carboxylase feedback resistant EC 4.1.1.31 (phosphoenolpyruvate carboxylase feedback resistant) | EP0723011 WO0100852 | |
| ppc | Phosphoenolpyruvate carboxylase EC 4.1.1.31 (phosphoenolpyruvate carboxylase) | EP1108790 O'Reagan et al., Gene 77(2): 237-251 (1989) | AX127148 AX123554 M25819 |
| pgk | Phosphoglycerate kinase EC 2.7.2.3 (phosphoglycerate kinase) | EP1108790 WO0100844 Eikmanns, Journal of Bacteriology 174: 6076-6086 (1992) | AX121838 AX127148 AX064943 X59403 |
| pknA | Protein kinase A (protein kinase A) | EP1108790 | AX120131 AX120085 |
| pknB | Protein kinase B (protein kinase B) | EP1108790 | AX120130 AX120085 |
| pknD | Protein kinase D (protein kinase D) | EP1108790 | AX127150 AX122469 AX122468 |
| pknG | Protein kinase G (protein kinase G) | EP1108790 | AX127152 AX123109 |
| ppsA | Phosphoenolpyruvate synthase EC 2.7.9.2 (phosphoenolpyruvate synthase) | EP1108790 | AX127144 AX120700 AX122469 |
| ptsH | Phosphotransferase system protein H EC 2.7.1.69 (phosphotransferase system component H) | EP1108790 WO0100844 | AX122210 AX127149 AX069154 |
| ptsI | Phosphotransferase system enzyme I EC 2.7.3.9 (phosphotransferase system enzyme I) | EP1108790 | AX122206 AX127149 |
| ptsM | Glucose-specific phosphotransferase system enzyme II EC 2.7.1.69 (glucose-phosphotransferase-system enzyme II) | Lee et al., FEMS Microbiology Letters 119(1-2): 137-145 (1994) | L18874 |
| pyc | Pyruvate carboxylase EC 6.4.1.1 (pyruvate carboxylase) | WO9918228 Peters-Wendisch et al., Microbiology 144: 915-927 (1998) | A97276 Y09548 |
| pyc P458S | Pyruvate carboxylase EC 6.4.1.1 (pyruvate carboxylase) Amino acid exchange P458S | EP1108790 | |
| sigC | Sigma factor C EC 2.7.7.6 (extracytoplasmic function alternative sigma factor C) | EP1108790 | AX120368 AX120085 |
| sigD | RNA polymerase sigma factor D EC 2.7.7.6 (RNA polymerase sigma factor) | EP1108790 | AX120753 AX127144 |
| sigE | Sigma factor E EC 2.7.7.6 (extracytoplasmic function alternative sigma factor E) | EP1108790 | AX127146 AX121325 |

TABLE 1-continued

Genes and alleles of lysine production

| Name | Description of the coded enzyme or protein | Reference | Accession number |
|---|---|---|---|
| sigH | Sigma factor H<br>EC 2.7.7.6<br>(sigma factor SigH) | EP1108790 | AX127145<br>AX120939 |
| SigM | Sigma factor M<br>EC 2.7.7.6<br>(sigma factor SigM) | EP1108790 | AX123500<br>AX127153 |
| tal | Transaldolase<br>EC 2.2.1.2<br>(transaldolase) | WO0104325 | AX076272 |
| thyA | Thymidylate synthase<br>EC 2.1.1.45<br>(thymidylate synthase) | EP1108790 | AX121026<br>AX127145 |
| tkt | Transketolase<br>EC 2.2.1.1<br>(transketolase) | Ikeda et al.,<br>NCBI | AB023377 |
| tpi | Triose-phosphate isomerase<br>EC 5.3.1.1<br>(triose-phosphate isomerase) | Eikmanns,<br>Journal of<br>Bacteriology<br>174: 6076-6086<br>(1992) | X59403 |
| zwa1 | Cell growth factor 1<br>(growth factor 1) | EP1111062 | AX133781 |
| zwf | Glucose-6-phosphate-1-dehydrogenase<br>EC 1.1.1.49<br>(glucose-6-phosphate-1-dehydrogenase) | EP1108790<br>WO0104325 | AX127148<br>AX121827<br>AX076272 |
| zwf A213T | Glucose-6-phosphate-1-dehydrogenase<br>EC 1.1.1.49<br>(glucose-6-phosphate-1-dehydrogenase)<br>Amino acid exchange A213T | EP1108790 | |

In addition, it can be advantageous for production of L-lysine when, in addition to the functional expression of one or more of the heterologous genes of glycerol metabolism selected from the group glpA, glpB, glpC, glpD, glpE, glpF, glpG, glpK, glpQ, glpT, glpX, gldA, dhaK, dhaL, dhaM, dhaR, fsa and talC, at the same time one or more of the genes selected from the group of genes or alleles which are not essential for growth or lysine production is or are attenuated, in particular switched off, or their expression decreased.

The following open reading frames, genes or alleles, inter alia, can be used for this: aecD, ccpA1, ccpA2, citA, citB, cite, fda, glua, gluB, gluC, gluD, luxR, luxS, lysR1, lysR2, lysR3, menE, mqo, pck, pgi, poxB and zwa2, which are summarized and explained in Table 2.

TABLE 2

Genes and alleles which are not essential for lysine production

| Gene name | Description of the coded enzyme or protein | Reference | Accession number |
|---|---|---|---|
| aecD | beta C-S Lyase<br>EC 2.6.1.1<br>(beta C-S lyase) | Rossol et al., Journal of Bacteriology 174(9): 2968-77 (1992) | M89931 |
| ccpA1 | Catabolite control protein<br>(catabolite control protein A1) | WO0100844<br>EP1108790<br>WO 02/18419 | AX065267<br>AX127147 |
| ccpA2 | Catabolite control protein<br>(catabolite control protein A2) | WO0100844<br>EP1108790 | AX065267<br>AX121594 |
| citA | Sensor kinase CitA<br>(sensor kinase CitA) | EP1108790 | AX120161 |
| citB | Transcription regulator CitB<br>(transcription regulator CitB) | EP1108790 | AX120163 |
| citE | Citrate lyase<br>EC 4.1.3.6<br>(citrate lyase) | WO0100844<br>EP1108790 | AX065421<br>AX127146 |
| fda | Fructose bisphosphate aldolase<br>EC 4.1.2.13<br>(fructose-1,6-bisphosphate aldolase | von der Osten et al., Molecular Microbiology 3(11): 1625-37 (1989) | X17313 |
| gluA | Glutamate transport ATP-binding protein<br>(glutamate transport ATP-binding protein) | Kronemeyer et al., Journal of Bacteriology 177(5): 1152-8 (1995) | X81191 |
| gluB | glutamate binding protein<br>(glutamate binding protein) | Kronemeyer et al., Journal of Bacteriology 177(5): 1152-8 (1995) | X81191 |

TABLE 2-continued

Genes and alleles which are not essential for lysine production

| Gene name | Description of the coded enzyme or protein | Reference | Accession number |
|---|---|---|---|
| gluC | Glutamate transport permease (glutamate transport system permease) | Kronemeyer et al., Journal of Bacteriology 177(5): 1152-8 (1995) | X81191 |
| gluD | Glutamate transport permease (glutamate transport system permease) | Kronemeyer et al., Journal of Bacteriology 177(5): 1152-8 (1995) | X81191 |
| luxR | Transcription regulator LuxR (transcription regulator LuxR) | WO0100842 EP1108790 | AX065953 AX123320 |
| luxS | Histidine kinase LuxS (histidine kinase LuxS) | EP1108790 | AX123323 AX127153 |
| lysR1 | Transcription regulator lysR1 (transcription regulator LysR1) | EP1108790 | AX064673 AX127144 |
| lysR2 | Transcription activator LysR2 (transcription regulator LysR2) | EP1108790 | AX123312 |
| lysR3 | Transcription regulator LysR3 (transcription regulator LysR3) | WO0100842 EP1108790 | AX065957 AX127150 |
| menE | O-Succinylbenzoate-CoA-ligase EC 6.2.1.26 (O-succinylbenzoate-CoA-ligase) | WO0100843 EP1108790 | AX064599 AX064193 AX127144 |
| mqo | Malate-quinone-oxidoreductase (malate-quinone-oxidoreductase) | Molenaar et al., Eur. Journal of Biochemistry 1; 254(2): 395-403 (1998) | AJ224946 |
| pck | Phosphoenolpyruvate carboxykinase (phosphoenolpyruvate carboxykinase) | WO0100844 EP-A-1094111 | AJ269506 AX065053 |
| pgi | Glucose-6-phosphate isomerase EC 5.3.1.9 (glucose-6-phosphate isomerase) | EP1087015 EP1108790 WO01/07626 | AX136015 AX127146 |
| poxB | Pyruvate oxidase EC 1.2.3.3 (pyruvate oxidase) | WO0100844 EP1096013 | AX064959 AX137665 |
| zwa2 | Cell growth factor 2 (growth factor 2) | EP1106693 EP1108790 | AX113822 AX127146 |

It is also possible to amplify endogenous polynucleotides from *Corynebacterium glutamicum* (Accession No.: NC 006958 and NC 003450 (sequence of the entire genome)), which have, for example, at least 45%, or at least 50%, or at least 60%, or at least 70%, or at least 80%, or at least 90%, at least 91%, at least 92%, at least 93%, at least 94%, at least 95%, at least 96%, at least 97%, at least 98% or at least 99% identity with the nucleotide sequences described in SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33 or SEQ ID No. 35 and which have the functions described. The nucleotide sequences of the genes and ORFs known from the genome projects are part of the prior art and can be taken from various publications, patent applications and also the database of the National Center for Biotechnology Information (NCBI) of the National Library of Medicine (Bethesda, Md., USA).

It has been found that coryneform bacteria, also after shared overexpression of the endogenous polynucleotides glpK (58% identity with SEQ ID No. 15), encoding the ATP-dependent glycerol kinase K, and glpD (47% identity with SEQ ID No. 7), encoding the glycerol-3-phosphate dehydrogenase of glycerol metabolism produce L-amino acids, in particular L-lysine and L-tryptophan, from glycerol as sole carbon source.

For the sake of better clarity, the known sequences of the treated genes of *Corynebacterium glutamicum* are described under SEQ ID No. 37 and SEQ ID No. 39.

The bacteria of the invention can be cultured continuously, such as, for example, in the method described in PCT/EP2004/008882, or discontinuously in the batch method or in the fed batch method or repeated fed batch method for the purposes of production of L-amino acids. A summary of known culture methods is available in the textbook by Chmiel (Bioprozesstechnik 1. Einfuhrung in die Bioverfahrenstechnik [Biomethod technology 1. Introduction to biomethod engineering] (Gustav Fischer Verlag, Stuttgart, 1991)) or in the textbook by Storhas (Bioreaktoren und periphere Einrichtungen [Bioreactors and peripheral equipment] (Vieweg Verlag, Brunswick/Wiesbaden, 1994)).

The culture medium to be used must meet the requirements of the respective strains in a suitable manner. Descriptions of culture media for various microorganisms are contained in the handbook "Manual of Methods for General Bacteriology" of the American Society for Bacteriology (Washington D.C., USA, 1981).

The carbon source used is glycerol. This can be used individually or as a mixture. Sugars and carbohydrates such as, for example, glucose, sucrose, lactose, fructose, maltose, molasses, starch and if appropriate cellulose, oils and fats such as, for example, soybean oil, sunflower seed oil, peanut oil and coconut fat, fatty acids such as, for example, palmitic acid, stearic acid and linoleic acid, alcohols such as, for example, ethanol and methanol, and organic acids such as, for example, acetic acid, can be added, in which case the fraction of glycerol is at least greater than or equal to ($\geq$) 10%, or at least $\geq$25%, or at least $\geq$50%, or at least $\geq$75%, or at least $\geq$90%, or at least $\geq$95%, at least greater $\geq$99%, preferably 100%.

As nitrogen source, use can be made of organic nitrogenous compounds such as peptones, yeast extract, meat extract, malt extract, corn steep water, soybean meal and urea, or inorganic compounds such as ammonium sulfate, ammonium chloride, ammonium phosphate, ammonium carbonate and ammonium nitrate. The nitrogen sources can be used individually or as a mixture.

As phosphorus source, use can be made of phosphoric acid, potassium dihydrogenphosphate or dipotassium hydrogenphosphate or the corresponding sodium-containing salts. The culture medium must in addition contain salts of metals such as, for example, magnesium sulfate or iron sulfate, which are necessary for growth. Finally, in addition to the above-mentioned substances, use can be made of essential growth substances such as amino acids and vitamins. In addition, suitable precursors can be added to the culture medium. Said feed materials can be added to the culture in the form of a single batch or can be fed in during the culture in a suitable manner.

For pH control of the culture, use is made, in a suitable manner, of basic compounds such as sodium hydroxide, potassium hydroxide, ammonia or ammonia water or acidic compounds such as phosphoric acid or sulfuric acid. For control of foam development, use can be made of antifoams such as, for example, fatty acid polyglycol esters. To maintain the stability of plasmids, suitable selectively acting substances such as, for example, antibiotics can be added to the medium. To maintain aerobic conditions, oxygen or oxygen-containing gas mixtures such as, for example, air, are introduced into the culture. The temperature of the culture is usually 20° C. to 45° C. and preferably 25° C. to 40° C. The culture is continued until a maximum of the desired product has formed. This target is usually achieved within 10 hours to 160 hours. In continuous methods, longer culture times are possible.

Methods of determining L-amino acids are known from the prior art. The analysis can proceed as described in Spackman et al. (Analytical Chemistry, 30, (1958), 1190) by anion-exchange chromatography with subsequent ninhydrin derivatization, or it can proceed by reversed-phase HPLC, as described in Lindroth et al. (Analytical Chemistry (1979) 51: 1167-1174).

The invention claimed is:

1. A method for producing an L-amino acid comprising:
   a) culturing a recombinant *Corynebacterium glutamicum* bacterium producing an L-amino acid in culture medium containing glycerol as a carbon source, and
   b) recovering the L-amino acid;
   wherein said recombinant *Corynebacterium glutamicum* bacterium is transformed with a heterologous nucleic acid encoding:
   a GlpK polypeptide comprising an amino acid sequence that is at least 95% identical to the amino acid sequence of SEQ ID NO: 16, wherein the GlpK polypeptide has glycerol kinase activity, and
   a GlpD polypeptide comprising an amino acid sequence that is at least 95% identical to the amino acid sequence of SEQ ID NO: 8, wherein the GlpD polypeptide has glycerol-3-phosphate dehydrogenase activity;
   and wherein said recombinant *Corynebacterium glutamicum* bacterium utilizes metabolizes said glycerol as a carbon source to produce said L-amino acid.

2. The method of claim 1, wherein the glycerol constitutes 10% to 25% of the carbon source in said medium.

3. The method of claim 1, wherein the glycerol constitutes 25% to 50% of the carbon source in said medium.

4. The method of claim 1, wherein the glycerol constitutes 50% to 90% of the carbon source in said medium.

5. The method of claim 1, wherein the glycerol constitutes at least 90% of the carbon source in said medium.

6. The method of claim 1, wherein the amino acid is recovered from the culture medium.

7. The method of claim 1, wherein the amino acid is recovered from the recombinant *Corynebacterium glutamicum* bacterium.

8. The method of claim 1, wherein said L-amino acid is L-lysine.

9. The method of claim 1, wherein said L-amino acid is L-tryptophan.

10. The method of claim 1, wherein the GlpK polypeptide comprises an amino acid sequence that is at least 99% identical to the amino acid sequence of SEQ ID NO: 16, wherein the GlpK polypeptide has glycerol kinase activity.

11. The method of claim 1, wherein the GlpD polypeptide comprises an amino acid sequence that is at least 99% identical to the amino acid sequence of SEQ ID NO: 8, wherein the GlpD polypeptide has glycerol-3-phosphate dehydrogenase activity.

12. The method of claim 1, wherein said recombinant *Corynebacterium glutamicum* bacterium is further transformed with a heterologous nucleic acid encoding a GlpF polypeptide comprising an amino acid sequence that is at least 95% identical to the amino acid sequence of SEQ ID NO: 12, wherein the GlpF polypeptide facilitates diffusion of glycerol.

13. The method of claim 1, wherein said recombinant *Corynebacterium glutamicum* bacterium is further transformed with a heterologous nucleic acid encoding a GlpF polypeptide comprising an amino acid sequence that is at least 99% identical to the amino acid sequence of SEQ ID NO: 12, wherein the GlpF polypeptide facilitates diffusion of glycerol.

14. The method of claim 1, wherein said recombinant *Corynebacterium glutamicum* bacterium is further transformed with at least one heterologous nucleic acid encoding:
   a GlpA polypeptide comprising an amino acid sequence that is at least 95% identical to the amino acid sequence of SEQ ID NO: 2, wherein the GlpA polypeptide has sn-glycerol-3-phosphate dehydrogenase activity,
   a GlpB polypeptide comprising an amino acid sequence that is at least 95% identical to the amino acid sequence of SEQ ID NO: 4, wherein the GlpB polypeptide has sn-glycerol-3-phosphate dehydrogenase activity,
   a GlpC polypeptide comprising an amino acid sequence that is at least 95% identical to the amino acid sequence of SEQ ID NO: 6, wherein the GlpC polypeptide has sn-glycerol-3-phosphate dehydrogenase activity,
   a GlpE polypeptide comprising an amino acid sequence that is at least 95% identical to the amino acid sequence of SEQ ID NO: 10, wherein the GlpE polypeptide has sulfur transferase activity,
   a GlpG polypeptide comprising the amino acid sequence of SEQ ID NO: 14,
   a GlpQ polypeptide comprising an amino acid sequence that is at least 95% identical to the amino acid sequence of SEQ ID NO: 18, wherein the GlpQ polypeptide has glycerol phosphodiesterase activity, a GlpT polypeptide comprising an amino acid sequence that is at least 95% identical to the amino acid sequence of SEQ ID NO: 20, wherein the GlpT polypeptide has glycerol-3-phosphate permease activity, a GlpX polypeptide comprising an amino acid sequence that is at least 95% identical to the amino acid sequence of SEQ ID NO: 22, wherein the GlpX polypeptide has fructose-1,6-bisphosphatase II activity, a GldA polypeptide comprising an amino acid sequence that is at least 95% identical to the amino acid sequence of SEQ ID NO: 24, wherein the GldA polypeptide has glycerol dehydrogenase activity, a DhaK polypeptide comprising an amino acid sequence that is at least 95% identical to the amino acid sequence of SEQ ID NO: 26, wherein the DhaK polypeptide has dihydroxyacetone kinase activity, a DhaL polypeptide comprising an amino acid sequence that is at least 95% identical to the amino acid sequence of SEQ ID NO: 28, wherein the DhaL polypeptide has dihydroxyacetone kinase activity, a DhaM polypeptide comprising an amino acid sequence that is at least 95% identical to the amino acid sequence of SEQ ID NO: 30, wherein the DhaM polypeptide has dihydroxyacetone kinase activity, a DhaR polypeptide comprising an amino acid sequence that is at least 95% identical to the amino acid sequence of SEQ ID NO: 32, wherein the DhaR polypeptide is a transcriptional activator of a dhaKLM operon, a Fsa polypeptide comprising an amino acid sequence that is at least 95% identical to the amino acid sequence of SEQ ID NO: 34, wherein the Fsa polypeptide has fructose-6-phosphate aldolase I activity, or a Talc polypeptide comprising an amino acid sequence that is at least 95% identical to the amino acid sequence of SEQ ID NO: 36, wherein the Talc polypeptide has fructose-6-phosphate aldolase II activity.

15. A recombinant *Corynebacterium glutamicum* bacterium that has been transformed with a heterologous nucleic acid encoding:

a GlpK polypeptide comprising an amino acid sequence that is at least 95% identical to the amino acid sequence of SEQ ID NO: 16, wherein the GlpK polypeptide has glycerol kinase activity, and a GlpD polypeptide comprising an amino acid sequence that is at least 95% identical to the amino acid sequence of SEQ ID NO: 8, wherein the GlpD polypeptide has glycerol-3-phosphate dehydrogenase activity;

wherein said recombinant *Corynebacterium glutamicum* bacterium metabolizes glycerol as a carbon source to produce an L-amino acid in a culture medium containing glycerol.

16. The recombinant *Corynebacterium glutamicum* bacterium of claim 15 that has been further transformed with a heterologous nucleic acid encoding a GlpF polypeptide comprising an amino acid sequence that is at least 95% identical to the amino acid sequence of SEQ ID NO: 12, wherein the GlpF polypeptide facilitates diffusion of glycerol.

17. The recombinant *Corynebacterium glutamicum* bacterium of claim 15 that has been further transformed with at least one heterologous nucleic acid encoding:

a GlpA polypeptide comprising an amino acid sequence that is at least 95% identical to the amino acid sequence of SEQ ID NO: 2, wherein the GlpA polypeptide has sn-glycerol-3-phosphate dehydrogenase activity, a GlpB polypeptide comprising an amino acid sequence that is at least 95% identical to the amino acid sequence of SEQ ID NO: 4, wherein the GlpB polypeptide has sn-glycerol-3-phosphate dehydrogenase activity, a GlpC polypeptide comprising an amino acid sequence that is at least 95% identical to the amino acid sequence of SEQ ID NO: 6, wherein the GlpC polypeptide has sn-glycerol-3-phosphate dehydrogenase activity, a GlpE polypeptide comprising an amino acid sequence that is at least 95% identical to the amino acid sequence of SEQ ID NO: 10, wherein the GlpE polypeptide has sulfur transferase activity, a GlpG polypeptide comprising the amino acid sequence of SEQ ID NO: 14, a GlpQ polypeptide comprising an amino acid sequence that is at least 95% identical to the amino acid sequence of SEQ ID NO: 18, wherein the GlpQ polypeptide has glycerol phosphodiesterase activity, a GlpT polypeptide comprising an amino acid sequence that is at least 95% identical to the amino acid sequence of SEQ ID NO: 20, wherein the GlpT polypeptide has glycerol-3-phosphate permease activity, a GlpX polypeptide comprising an amino acid sequence that is at least 95% identical to the amino acid sequence of SEQ ID NO: 22, wherein the GlpX polypeptide has fructose-1,6-bisphosphatase II activity, a GldA polypeptide comprising an amino acid sequence that is at least 95% identical to the amino acid sequence of SEQ ID NO: 24, wherein the GldA polypeptide has glycerol dehydrogenase activity, a DhaK polypeptide comprising an amino acid sequence that is at least 95% identical to the amino acid sequence of SEQ ID NO: 26, wherein the DhaK polypeptide has dihydroxyacetone kinase activity, a DhaL polypeptide comprising an amino acid sequence that is at least 95% identical to the amino acid sequence of SEQ ID NO: 28, wherein the DhaL polypeptide has dihydroxyacetone kinase activity, a DhaM polypeptide comprising an amino acid sequence that is at least 95% identical to the amino acid sequence of SEQ ID NO: 30, wherein the DhaM polypeptide has dihydroxyacetone kinase activity, a DhaR polypeptide comprising an amino acid sequence that is at least 95% identical to the amino acid sequence of SEQ ID NO: 32, wherein the DhaR polypeptide is a transcriptional activator of a dhaKLM operon, a Fsa polypeptide comprising an amino acid sequence that is at least 95% identical to the amino acid sequence of SEQ ID NO: 34, wherein the Fsa polypeptide has fructose-6-phosphate aldolase I activity, or a Talc polypeptide comprising an amino acid sequence that is at least 95% identical to the amino acid sequence of SEQ ID NO: 36, wherein the Talc polypeptide has fructose-6-phosphate aldolase II activity.

18. The recombinant *Corynebacterium glutamicum* bacterium of claim 15, wherein said L-amino acid is L-lysine.

19. The recombinant *Corynebacterium glutamicum* bacterium of claim 15, wherein said L-amino acid is L-tryptophan.

* * * * *